United States Patent [19]
Al-Obeidi et al.

[11] Patent Number: 5,849,510
[45] Date of Patent: Dec. 15, 1998

[54] FACTOR XA INHIBITORS

[75] Inventors: Fahad Al-Obeidi; Michal Lebl; James A. Ostrem; Pavel Safar; Alena Stierandova; Peter Strop; Armin Walser, all of Tucson, Ariz.

[73] Assignee: Selectide Corporation, Tucson, Ariz.

[21] Appl. No.: 947,794

[22] Filed: Oct. 8, 1997

Related U.S. Application Data

[63] Continuation of Ser. No. 428,404, Apr. 25, 1995, abandoned, which is a continuation-in-part of Ser. No. 233,054, Apr. 26, 1994, abandoned.

[51] Int. Cl.$^6$ .............................. C12Q 1/56; C12Q 1/00; G01N 33/53; A61K 38/00
[52] U.S. Cl. .............................. 435/13; 435/7.25; 435/4; 435/2; 436/520; 436/521; 436/522; 436/15; 436/63; 436/68; 436/69; 436/74; 530/300; 530/380; 530/381; 530/384; 530/385
[58] Field of Search .............................. 435/13, 7.25, 4, 435/2; 436/520, 521, 522, 15, 63, 68, 69, 74; 530/300, 380, 381, 384, 385

[56] References Cited

U.S. PATENT DOCUMENTS

| | | | |
|---|---|---|---|
| 4,428,874 | 1/1984 | Svendsen et al. | 260/112.5 R |
| 4,605,614 | 8/1986 | Nagasawa et al. | 435/13 |
| 4,772,553 | 9/1988 | Fujii et al. | 435/13 |
| 5,023,236 | 6/1991 | Edgington et al. | 530/325 |
| 5,189,019 | 2/1993 | Palladino et al. | 530/325 |
| 5,239,058 | 8/1993 | Vlasuk et al. | 530/325 |
| 5,240,913 | 8/1993 | Maraganore et al. | 530/325 |
| 5,328,997 | 7/1994 | Vlasuk et al. | 536/23.5 |
| 5,439,888 | 8/1995 | Shuman et al. | 514/2 |

FOREIGN PATENT DOCUMENTS

| | | |
|---|---|---|
| 0 119 705 | 2/1984 | European Pat. Off. . |
| 0 171 270 | 8/1985 | European Pat. Off. . |
| WO 80/00351 | 3/1980 | WIPO . |
| WO 93/15756 | 8/1993 | WIPO . |

OTHER PUBLICATIONS

Claeson and Aurell, "Small Synthetic Peptides with Affinity for Proteases in Coagulation and Fibrinolysis," *Ann. N.Y. Acad. Sci. (USA)* 370:798–811 (1981).

Jorgenson et al., Angiotensin II Analogs. 6.$^1$ Stereochemical Factors in the 5 Position Influencing Pressor Activity. 1, *J. Med. Chem.* 14:899–903 (1971).

Maule et al., "RYIRFamide: a Turbellarian FMRFamide–related peptide (FaRI)," *Regulatory Peptides* 50:37–43 (1994).

Messmore et al., "Coagulant Enzymes and Synthetic Inhibitors," *Thromb. Haemostasis* 42:952 (1979).

Ponsati et al., "A Synthetic Strategy for Simultaneous Purification–Conjugation of Antigenic Peptides," *Analytical Biochemistry* 181:889–395 (1989).

(List continued on next page.)

*Primary Examiner*—Louise N. Leary
*Attorney, Agent, or Firm*—Campbell & Flores LLP

[57] ABSTRACT

The invention provides compounds which specifically inhibit factor Xa activity. The compounds consist of the structure $X_1$-YIR-$X_2$, wherein $X_1$ is H, acyl, alkyl, acylalkyl, arylalkyl or one or more amino acids, and $X_2$ is a modified C-terminal group, one or more carboxy-protecting groups or one or more amino acids or other substituent, and Y, I and R are tyrosine, isoleucine and arginine, respectively, or peptidomimetic or organic structures that possess the same functional activity as Y, I and R, respectively. In addition, the present invention provides a compound having the structure A1-A2-(A3)$_m$—B, where m is 0 or 1. A compound of the invention can be linear or cyclic and can be about 2 and 43 residues in length. A compound of the invention is characterized, in part, in that it exhibits a specific inhibition of factor Xa activity with a $K_i$ of $\leq 100$ μM, preferably $\leq 2$ nM, and does not substantially inhibit the activity of other proteases involved in the coagulation cascade. The invention further provides methods of specifically inhibiting the activity of factor Xa and of inhibiting blood clotting in vitro and in an individual and methods of detecting factor Xa levels or activity.

43 Claims, 4 Drawing Sheets

BLOOD COAGULATION CASCADE

OTHER PUBLICATIONS

Shaw, "Synthetic Irreversible of Coagulation Enzymes," *Folia Haematol.* 109:33–42 (1982).

Choay, et al., "Structure–Activity Relationship in Heparin: A Synthetic Pentasaccharide with High Affinity for Antithrombin III and Eliciting High Anti–Factor Xa Activity," *Bioch. Biophys. Res. Com.* 116:492–499 (1983).

de Feyer, et al., "Acute Coronary Artery Occlusion During and After Percutaneous Transluminal Coronary Angioplasty," *Circulation* 83:927–936 (1991).

Detre, et al., "Incidence and Consequences of Periprocedural Occlusion," *Circulation* 82:739–750 (1991).

Dunwiddle, et al., "Antistasin, a Leech–derived Inhibitor of Factor Xa," *J. Biol. Chem.* 264:16694–16696 (1989).

Harenberg, "Relation of Antifactor Xa Activity of Heparins and Antithrombotic Efficacy," *Haemostasis* 18:16–19 (1988).

Hauptmann, et al., "Comparison of the Anticoagulant and Antithrombotic Effects of Synthetic Thrombin and Factor Xa Inhibitors," *Thromb. Haemost.* 63:220–223 (1990).

Hogg, et al., "Fibrin Monomer Protects Thrombin from Inactivation by Heparin–Antithrombin III: Implications for Heparin Efficacy," *PNAS* 86:3619–3623 (1989).

Lincoff, et al., "Abrupt Vessel Closure Complicating Coronary Angioplasty: Clinical, Angiographic and Therapeutic Profile," *J. Am. Coll. Cardiol.* 19:926–935 (1992).

Mann and Lorand, "Introduction: Blood Coagulation," *Methods in Enzymology* 222:1–10 (1993).

Maraganore, "Design and Characterization of Hirulogs: A Novel Class of Bivalent Peptide Inhibitors of Thrombin," *Biochemistry* 29:7095–7101 (1990).

Meuleman, "Orgaran (Org 10172): Its Pharmacological Profile in Experimental Models," *Haemostasis* 22:58–65 (1992).

Nutt, et al., "The Amino Acid Sequence of Antistasin," *J. Biol. Chem.* 263:10162–10167 (1988).

Ofosu, et al., "An Approach to Assigning In Vitro Potency to Unfractioned and Low Molecular Weight Heparins Based on the Inhibition of Prothrombin Activation and Catalysis of Thrombin Inhibition," *Thromb. Haemost.* 60:193–198 (1988).

Schaffer, et al., "Antithrombotic Efficacy of Recombinant Tick Anticoagulant Peptide, A Potent Inhibitor of Coagulation Factor Xa in a Primate Model of Arterial Thrombosis," *Circulation* 84:1741–1747 (1991).

Swayze, et al., "Deep Venous Thrombosis in Total Hip Arthroplasty," *Orthop. Clin. North. Am.*, 23:359–364 (1992).

Teitel and Rosenberg, "Protection of Factor Xa from Neutralization by the Heparin–Antithrombin Complex," *J. Clin. Invest.* 71:1383–1391 (1983).

Tidwell, et al., "Strategies for Anticoagulation with Synthetic Protease Inhibitors. Xa Inhibitors Versus Thrombin Inhibitors," *Thromb. Res.* 19:339–349 (1980).

Topol, et al., "Use of a Direct Antithrombin, Hirulog, in Place of Heparin During Coronary Angioplasty," *Circulation* 87:1622–1629 (1993).

Turpie, et al., "A Randomized Controlled Trial of a Low–Molecular Weight Heparin (Enoxaparin) to Prevent Deep–Vein Thrombosis in Patients Undergoing Elective Hip Surgery," *New Eng. J. Med.* 315:925–929 (1986).

Vlasuk, "Comparison of the In Vivo Anticoagulant Properties of Standard Heparin and the Highly Selective Factor Xa Inhibitors Antistasin and Tick Anticoagulant Peptide (TAP) in a Rabbit Model of Venous Thrombosis," *Thromb. Haemost.* 65:257–262 (1991).

Waxman, et al., "Tick Anticoagulant Peptide (TAP) Is a Novel Inhbitor of Blood Coagulation Factor Xa," *Science* 248:593–596 (1990).

Wessler "Mini–Dose Heparin," *Thrombos. Diathes. Hemorrh.* 34:718–726 (1978).

Yin "Heparin–Accelerated Inhibition of Activated Factor Xa by its Natural Plasma Inhibitor," *Bioch. Biophys. Acta.* 201:387–390 (1970).

SEQUENCE LISTING ( 1 ) GENERAL INFORMATION:

( i i i ) NUMBER OF SEQUENCES: 290

( 2 ) INFORMATION FOR SEQ ID NO:1:

( i ) SEQUENCE CHARACTERISTICS:

( x i ) SEQUENCE DESCRIPTION:SEQ ID NO:1:
        This sequence has been omitted ( 2 ) INFORMATION FOR SEQ ID NO:2:

( i ) SEQUENCE CHARACTERISTICS:
        ( A ) LENGTH: 5 amino acids (B) TYPE: amino acid
                (D) TOPOLOGY: linear (ix) FEATURE:
                (A) NAME/KEY: Peptide
                (B) LOCATION: 1
                (D) OTHER INFORMATION: /note= "Amino acid is acetylated at
                        the N- terminal."

(ix) FEATURE:
                (A) NAME/KEY: Peptide
                (B) LOCATION: 5
                (D) OTHER INFORMATION: /note= "Amino acid is amidated at
                        the C- terminal."

(xi) SEQUENCE DESCRIPTION: SEQ ID NO:2:

Tyr  Ile  Arg  Leu  Ala
        1                   5

(2) INFORMATION FOR SEQ ID NO:3:

(xi) SEQUENCE DESCRIPTION: SEQ ID NO:2:

Tyr  Ile  Arg  Leu  Ala
        1                   5

(ix) FEATURE:
                        (A) NAME/KEY: Peptide
                        (B) LOCATION: 1
                        (D) OTHER INFORMATION: /note= "Amino acid is acetylated at
                                the N-terminal."

(ix) FEATURE:
                        (A) NAME/KEY: Peptide
                        (B) LOCATION: 5
                        (D) OTHER INFORMATION: /note= "Amino acid is amidated at
                                the C-terminal."

(xi) SEQUENCE DESCRIPTION: SEQ ID NO:3:

Tyr  Ile  Arg  Leu  Pro
        1                   5

(2) INFORMATION FOR SEQ ID NO:4:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note= "Amino acid is acetylated at
                        the N- terminal."

(ix) FEATURE:
                (A) NAME/KEY: Peptide
                (B) LOCATION: 1
                (D) OTHER INFORMATION: /note= "Tyr has an iBu group."

(ix) FEATURE:
                (A) NAME/KEY: Peptide
                (B) LOCATION: 5
                (D) OTHER INFORMATION: /note= "Amino acid is amidated at
                        the C- terminal."

(xi) SEQUENCE DESCRIPTION: SEQ ID NO:4:

Tyr  Ile  Arg  Leu  Pro
        1                   5

(2) INFORMATION FOR SEQ ID NO:5:

(i) SEQUENCE CHARACTERISTICS:

(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 1..2
(D) OTHER INFORMATION: /note= "There is a pseudo peptide bond (CH- 2NH) at the Tyr-Ile site."

(ix) FEATURE:
(A) NAME/KEY: Peptide
(B) LOCATION: 5
(D) OTHER INFORMATION: /note= "Amino acid is amidated at the C- terminal."

(xi) SEQUENCE DESCRIPTION: SEQ ID NO:5:

Tyr Ile Arg Leu Pro
1               5

(2) INFORMATION FOR SEQ ID NO:6:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 2..3
(D) OTHER INFORMATION: /note= "There is a pseudo peptide bond (CH- 2NH) at the Ile-Arg site."

(ix) FEATURE:
(A) NAME/KEY: Peptide
(B) LOCATION: 5
(D) OTHER INFORMATION: /note= "Amino acid is amidated at the C- terminal."

(xi) SEQUENCE DESCRIPTION: SEQ ID NO:6:

Tyr Ile Arg Leu Pro
1               5

(2) INFORMATION FOR SEQ ID NO:7:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 2
(D) OTHER INFORMATION: /note= "Xaa is Chg."

(ix) FEATURE:
(A) NAME/KEY: Peptide
(B) LOCATION: 3

( D ) OTHER INFORMATION: /note = "Arg has an NO-2 group."

( i x ) FEATURE:
    ( A ) NAME/KEY: Peptide
    ( B ) LOCATION: 3..4
    ( D ) OTHER INFORMATION: /note = "There is a pseudo peptide bond (CH-2NH) at the Arg(NO-2)-Leu site."

( i x ) FEATURE:
    ( A ) NAME/KEY: Peptide
    ( B ) LOCATION: 4
    ( D ) OTHER INFORMATION: /note = "Amino acid is amidated at the C-terminal."

( x i ) SEQUENCE DESCRIPTION: SEQ ID NO:7:

Tyr Xaa Arg Leu
1

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N-terminal."

( i x ) FEATURE:
        ( A ) NAME/KEY: Peptide
        ( B ) LOCATION: 3..4
        ( D ) OTHER INFORMATION: /note = "There is a pseudo peptide bond (CO-CH-2) at the Arg-Gly site."

( i x ) FEATURE:
        ( A ) NAME/KEY: Peptide
        ( B ) LOCATION: 5
        ( D ) OTHER INFORMATION: /note = "Amino acid is amidated at the C-terminal."

( x i ) SEQUENCE DESCRIPTION: SEQ ID NO:8:

Tyr Ile Arg Gly Pro
1                 5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N-terminal."

( i x ) FEATURE:
        ( A ) NAME/KEY: Peptide
        ( B ) LOCATION: 3
        ( D ) OTHER INFORMATION: /note = "Xaa is a Dab-derived dimethylamidinium."

( i x ) FEATURE:
        ( A ) NAME/KEY: Peptide
        ( B ) LOCATION: 5
        ( D ) OTHER INFORMATION: /note = "Amino acid is amidated at the C-terminal."

( x i ) SEQUENCE DESCRIPTION: SEQ ID NO:9:

Tyr Ile Xaa Leu Ala
1                 5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: circular ( x i ) SEQUENCE DESCRIPTION: SEQ ID NO:10:

Gly Tyr Ile Arg Gly
    1                  5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is
            trifluoroacetylated at the N-terminal."

( i x ) FEATURE:
        ( A ) NAME/KEY: Peptide
        ( B ) LOCATION: 1
        ( D ) OTHER INFORMATION: /note = "Tyr has an isobutyl group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:11:

Tyr Xaa Arg Leu Pro
    1                  5

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide
        ( B ) LOCATION: 1
        ( D ) OTHER INFORMATION: /note = "Phe has a p-amidino bond."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:12:

```
Phe  Xaa  Arg  Leu  Pro
1                   5
```

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 1
        ( D ) OTHER INFORMATION: /note = "Xaa is Nal(2)."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:13:

```
Xaa  Xaa  Arg  Leu  Pro
1                   5
```

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( D ) TOPOLOGY: unknown ( i x ) FEATURE:
        ( A ) NAME/KEY: Peptide
        ( B ) LOCATION: 1
        ( D ) OTHER INFORMATION: /note = "Xaa is A1 which is R1-R2-R3."

( i x ) FEATURE:
        ( A ) NAME/KEY: Peptide
        ( B ) LOCATION: 2
        ( D ) OTHER INFORMATION: /note = "Xaa is A2, which is R4-R5-R6."

( i x ) FEATURE:
        ( A ) NAME/KEY: Peptide
        ( B ) LOCATION: 3
        ( D ) OTHER INFORMATION: /note = "Xaa is (A3)m, wherein m is 0 or 1 and A3 is R7-R8-R9."

( i x ) FEATURE:
        ( A ) NAME/KEY: Peptide
        ( B ) LOCATION: 4
        ( D ) OTHER INFORMATION: /note = "Xaa is B."

( x i ) SEQUENCE DESCRIPTION: SEQ ID NO:14:

```
Xaa  Xaa  Xaa  Xaa
1
```

( 2 ) INFORMATION FOR SEQ ID NO:15:

( i ) SEQUENCE CHARACTERISTICS:
        ( A ) LENGTH: 5 amino acids (B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at
the N- terminal."

(ix) FEATURE:
(A) NAME/KEY: Peptide
(B) LOCATION: 1
(D) OTHER INFORMATION: /note = "Phe has a p-amidino bond."

(ix) FEATURE:
(A) NAME/KEY: Peptide
(B) LOCATION: 2
(D) OTHER INFORMATION: /note = "Xaa is Chg."

(ix) FEATURE:
(A) NAME/KEY: Peptide
(B) LOCATION: 3
(D) OTHER INFORMATION: /note = "Xaa is PalMe(3)."

(ix) FEATURE:
(A) NAME/KEY: Peptide
(B) LOCATION: 5
(D) OTHER INFORMATION: /note = "Amino acid is amidated at
the C- terminal."

(xi) SEQUENCE DESCRIPTION: SEQ ID NO:15:

Phe Xaa Xaa Leu Pro
1               5

(2) INFORMATION FOR SEQ ID NO:16:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is
trifluoracetylated at the N-terminal."

(ix) FEATURE:
(A) NAME/KEY: Peptide
(B) LOCATION: 1
(D) OTHER INFORMATION: /note = "Tyr has in iBu group."

(ix) FEATURE:
(A) NAME/KEY: Peptide
(B) LOCATION: 5
(D) OTHER INFORMATION: /note = "Amino acid is amidated at
the C- terminal."

(xi) SEQUENCE DESCRIPTION: SEQ ID NO:16:

Tyr Ile Arg Leu Pro
1               5

(2) INFORMATION FOR SEQ ID NO:17:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Tyr has an iBu group."

(ix) FEATURE:
(A) NAME/KEY: Peptide (B) LOCATION: 6
(D) OTHER INFORMATION: /note = "Xaa is Rink resin."

(xi) SEQUENCE DESCRIPTION: SEQ ID NO:17:

Tyr Ile Arg Leu Pro Xaa
1               5

(2) INFORMATION FOR SEQ ID NO:18:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "There is a Boc group at the N- terminal."

(ix) FEATURE:
(A) NAME/KEY: Peptide
(B) LOCATION: 1..2
(D) OTHER INFORMATION: /note = "There is a pseudo peptide bond (CH-2- NH) at the Ile-Arg(Tos) site."

(ix) FEATURE:
(A) NAME/KEY: Peptide
(B) LOCATION: 2
(D) OTHER INFORMATION: /note = "Arg has a tosyl group."

(ix) FEATURE:
(A) NAME/KEY: Peptide
(B) LOCATION: 5
(D) OTHER INFORMATION: /note = "Xaa is MBHA."

(xi) SEQUENCE DESCRIPTION: SEQ ID NO:18:

Ile Arg Leu Pro Xaa
1               5

(2) INFORMATION FOR SEQ ID NO:19:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 3
(D) OTHER INFORMATION: /note = "Xaa is Dab."

(ix) FEATURE:
(A) NAME/KEY: Peptide
(B) LOCATION: 6
(D) OTHER INFORMATION: /note = "Xaa is SCAL-TG."

(xi) SEQUENCE DESCRIPTION: SEQ ID NO:19:

Tyr Ile Xaa Leu Ala Xaa
1               5

(2) INFORMATION FOR SEQ ID NO:20:

(i) SEQUENCE CHARACTERISTICS:
(A) LENGTH: 6 amino acids
(B) TYPE: amino acid
(D) TOPOLOGY: circular ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 6
    ( D ) OTHER INFORMATION: /note = "Amino acid is amidated at the C- terminal."

( x i ) SEQUENCE DESCRIPTION: SEQ ID NO:20:

Glu Tyr Ile Arg Leu Lys
1               5

( 2 ) INFORMATION FOR SEQ ID NO:21:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Glu has an OtBu group."

( i x ) FEATURE:
    ( A ) NAME/KEY: Peptide
    ( B ) LOCATION: 2
    ( D ) OTHER INFORMATION: /note = "Tyr has a Butyl group."

( i x ) FEATURE:
    ( A ) NAME/KEY: Peptide
    ( B ) LOCATION: 4
    ( D ) OTHER INFORMATION: /note = "Arg has a Pmc group."

( i x ) FEATURE:
    ( A ) NAME/KEY: Peptide
    ( B ) LOCATION: 6
    ( D ) OTHER INFORMATION: /note = "Lys has a Boc group."

( i x ) FEATURE:
    ( A ) NAME/KEY: Peptide
    ( B ) LOCATION: 7
    ( D ) OTHER INFORMATION: /note = "Xaa is SCAL-TG."

( x i ) SEQUENCE DESCRIPTION: SEQ ID NO:21:

Glu Tyr Ile Arg Leu Lys Xaa
1               5

( 2 ) INFORMATION FOR SEQ ID NO:22:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "There is a Boc group at the N- terminal."

( i x ) FEATURE:
    ( A ) NAME/KEY: Peptide
    ( B ) LOCATION: 1
    ( D ) OTHER INFORMATION: /note = "Tyr has a 2-BrZ group."

-continued ( i x ) FEATURE:
    ( A ) NAME/KEY: Peptide
    ( B ) LOCATION: 3
    ( D ) OTHER INFORMATION: /note = "Arg has a Tos group."

( i x ) FEATURE:
    ( A ) NAME/KEY: Peptide
    ( B ) LOCATION: 5
    ( D ) OTHER INFORMATION: /note = "Xaa is an Oxime resin."

( x i ) SEQUENCE DESCRIPTION: SEQ ID NO:22:

```
Tyr  Ile  Arg  Gly  Xaa
1                   5
```

( 2 ) INFORMATION FOR SEQ ID NO:23:

( i ) SEQUENCE CHARACTERISTICS:
    ( A ) LENGTH: 6 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note = "Xaa is Ida."

( i x ) FEATURE:
    ( A ) NAME/KEY: Peptide
    ( B ) LOCATION: 6
    ( D ) OTHER INFORMATION: /note = "Amino acid is amidated at
      the C- terminal."

( x i ) SEQUENCE DESCRIPTION: SEQ ID NO:23:

```
Ser  Xaa  Ile  Arg  Leu  Ala
1                   5
```

( 2 ) INFORMATION FOR SEQ ID NO:24:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "There is an Fmoc group at
      the N- terminal."

( i x ) FEATURE:
    ( A ) NAME/KEY: Peptide
    ( B ) LOCATION: 2
    ( D ) OTHER INFORMATION: /note = "Arg has a Pmc group."

( i x ) FEATURE:
    ( A ) NAME/KEY: Peptide
    ( B ) LOCATION: 5
    ( D ) OTHER INFORMATION: /note = "Xaa is Rink."

( x i ) SEQUENCE DESCRIPTION: SEQ ID NO:24:

```
Ile  Arg  Leu  Ala  Xaa
1                   5
```

( 2 ) INFORMATION FOR SEQ ID NO:25:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

(ix) FEATURE:
    (A) NAME/KEY: Peptide
    (B) LOCATION: 1
    (D) OTHER INFORMATION: /note = "Phe has a p-amidino bond."

(ix) FEATURE:
    (A) NAME/KEY: Peptide
    (B) LOCATION: 5
    (D) OTHER INFORMATION: /note = "Amino acid is amidated at the C- terminal."

(xi) SEQUENCE DESCRIPTION: SEQ ID NO:25:

Phe Ile Arg Leu Pro
1                 5

(2) INFORMATION FOR SEQ ID NO:26:

(i) SEQUENCE CHARACTERISTICS:
        (A) LENGTH: 5 amino acids
        (B) TYPE: amino acid
        (D) TOPOLOGY: linear (ix) FEATURE:
    (A) NAME/KEY: Peptide
    (B) LOCATION: 1
    (D) OTHER INFORMATION: /note = "Amino acid is acetylated at the N- terminal."

(ix) FEATURE:
    (A) NAME/KEY: Peptide
    (B) LOCATION: 1
    (D) OTHER INFORMATION: /note = "Phe has a pNH-2 group."

(ix) FEATURE:
    (A) NAME/KEY: Peptide
    (B) LOCATION: 2
    (D) OTHER INFORMATION: /note = "Xaa is Chg."

(ix) FEATURE:
    (A) NAME/KEY: Peptide
    (B) LOCATION: 3
    (D) OTHER INFORMATION: /note = "Xaa is Orn(C(NH)CH-3)."

(ix) FEATURE:
    (A) NAME/KEY: Peptide
    (B) LOCATION: 5
    (D) OTHER INFORMATION: /note = "Amino acid is amidated at the C- terminal."

(xi) SEQUENCE DESCRIPTION: SEQ ID NO:26:

Phe Xaa Xaa Leu Pro
1                 5

(2) INFORMATION FOR SEQ ID NO:27:

(i) SEQUENCE CHARACTERISTICS:
        (A) LENGTH: 5 amino acids
        (B) TYPE: amino acid
        (D) TOPOLOGY: linear (ix) FEATURE:
    (A) NAME/KEY: Peptide
    (B) LOCATION: 1
    (D) OTHER INFORMATION: /note = "There is an Fmoc group at the N- terminal."

(ix) FEATURE:
    (A) NAME/KEY: Peptide
    (B) LOCATION: 1
    (D) OTHER INFORMATION: /note = "Xaa is Chg."

(ix) FEATURE:
    (A) NAME/KEY: Peptide
    (B) LOCATION: 2

( D ) OTHER INFORMATION: /note = "Xaa is Orn(Boc)."

( i x ) FEATURE:
    ( A ) NAME/KEY: Peptide
    ( B ) LOCATION: 5
    ( D ) OTHER INFORMATION: /note = "Xaa is SCAL-TG."

( x i ) SEQUENCE DESCRIPTION: SEQ ID NO:27:

Xaa Xaa Leu Pro Xaa
1                        5

( 2 ) INFORMATION FOR SEQ ID NO:28:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "There is an Fmoc group at
                the N- terminal."

( i x ) FEATURE:
        ( A ) NAME/KEY: Peptide
        ( B ) LOCATION: 1
        ( D ) OTHER INFORMATION: /note = "Xaa is Chg."

( i x ) FEATURE:
        ( A ) NAME/KEY: Peptide
        ( B ) LOCATION: 2
        ( D ) OTHER INFORMATION: /note = "Xaa is Orn(C(NH)CH-3)."

( i x ) FEATURE:
        ( A ) NAME/KEY: Peptide
        ( B ) LOCATION: 5
        ( D ) OTHER INFORMATION: /note = "Xaa is SCAL-TG."

( x i ) SEQUENCE DESCRIPTION: SEQ ID NO:28:

Xaa Xaa Leu Pro Xaa
1                        5

( 2 ) INFORMATION FOR SEQ ID NO:29:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
                the N- terminal."

( i x ) FEATURE:
        ( A ) NAME/KEY: Peptide
        ( B ) LOCATION: 1
        ( D ) OTHER INFORMATION: /note = "Phe has a pNH-BOC group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 3
        ( D ) OTHER INFORMATION: /note = "Xaa is Orn(C(NH)CH-3)"

( i x ) FEATURE:
        ( A ) NAME/KEY: Peptide
        ( B ) LOCATION: 6
        ( D ) OTHER INFORMATION: /note = "Xaa is SCAL-TG."

( x i ) SEQUENCE DESCRIPTION: SEQ ID NO:29:

Phe Xaa Xaa Leu Pro Xaa
1               5

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 1
        ( D ) OTHER INFORMATION: /note = "Phe has a pNH-2 group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 3
        ( D ) OTHER INFORMATION: /note = "Xaa is Dap-derived dimethylamidinium."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:30:

Phe Xaa Xaa Leu Pro
1               5

( 2 ) INFORMATION FOR SEQ ID NO:31:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 3
        ( D ) OTHER INFORMATION: /note = "Phe has a p-amidino bond."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:31:

Tyr Xaa Phe Leu Pro
1               5

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 1
        ( D ) OTHER INFORMATION: /note = "Tyr has a But group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 3
        ( D ) OTHER INFORMATION: /note = "Phe has a pCN group."

( i x ) FEATURE:
        ( A ) NAME/KEY: Peptide
        ( B ) LOCATION: 6
        ( D ) OTHER INFORMATION: /note = "Xaa is Knorr-TG."

( x i ) SEQUENCE DESCRIPTION: SEQ ID NO:32:

Tyr  Xaa  Phe  Leu  Pro  Xaa
    1                          5

( 2 ) INFORMATION FOR SEQ ID NO:33:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 1
        ( D ) OTHER INFORMATION: /note = "Phe has a pCH-2NH-2 group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:33:

Phe  Xaa  Arg  Leu  Pro
    1                        5

( 2 ) INFORMATION FOR SEQ ID NO:34:

( i ) SEQUENCE CHARACTERISTICS:
        ( A ) LENGTH: 5 amino acids (B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Phe has a pCN group."

(ix) FEATURE:
(A) NAME/KEY: Peptide
(B) LOCATION: 2
(D) OTHER INFORMATION: /note = "Xaa is Chg."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:34:

Phe Xaa Arg Leu Pro
1               5

(2) INFORMATION FOR SEQ ID NO:35:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Phe has a pC(NOH)NH-2 group."

(ix) FEATURE:
(A) NAME/KEY: Peptide
(B) LOCATION: 2
(D) OTHER INFORMATION: /note = "Xaa is Chg."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:35:

Phe Xaa Arg Leu Pro
1               5

(2) INFORMATION FOR SEQ ID NO:36:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Phe has a p-amidino bond and a DIPA bond."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:36:

Phe Xaa Arg Leu Pro
1               5

( 2 ) INFORMATION FOR SEQ ID NO:37:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Phe has a p-amidino bond and a DIPA bond."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 3
    ( D ) OTHER INFORMATION: /note = "Arg has a Pmc group."

( i x ) FEATURE:
    ( A ) NAME/KEY: Peptide
    ( B ) LOCATION: 6
    ( D ) OTHER INFORMATION: /note = "Xaa is Rink."

( x i ) SEQUENCE DESCRIPTION: SEQ ID NO:37:

Phe Xaa Arg Leu Pro Xaa
1               5

( 2 ) INFORMATION FOR SEQ ID NO:38:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Phe has a p-(C(NOH)NH-2) bond and a DIPA bond."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 3
    ( D ) OTHER INFORMATION: /note = "Arg has a Pmc group."

( i x ) FEATURE:
    ( A ) NAME/KEY: Peptide
    ( B ) LOCATION: 6
    ( D ) OTHER INFORMATION: /note = "Xaa is Rink."

( x i ) SEQUENCE DESCRIPTION: SEQ ID NO:38:

Phe Xaa Arg Leu Pro Xaa
1               5

(2) INFORMATION FOR SEQ ID NO:39:

(i) SEQUENCE CHARACTERISTICS:
        (A) LENGTH: 5 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note = "Amino acid is acetylated at
            the N- terminal."

(ix) FEATURE:
        (A) NAME/KEY: Peptide
        (B) LOCATION: 1
        (D) OTHER INFORMATION: /note = "Tyr has a (2-CF-3 Bzl)
            group."

(ix) FEATURE:
        (A) NAME/KEY: Peptide
        (B) LOCATION: 5
        (D) OTHER INFORMATION: /note = "Amino acid is amidated at
            the C- terminal."

(xi) SEQUENCE DESCRIPTION: SEQ ID NO:39:

Tyr Ile Arg Leu Pro
1               5

(2) INFORMATION FOR SEQ ID NO:40:

(i) SEQUENCE CHARACTERISTICS:
        (A) LENGTH: 5 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note = "Amino acid is acetylated at
            the N- terminal."

(ix) FEATURE:
        (A) NAME/KEY: Peptide
        (B) LOCATION: 1
        (D) OTHER INFORMATION: /note = "Tyr has a
            (CH-3 CH- 2 CH- 2 CH ( CH-3)CH-2) group."

(ix) FEATURE:
        (A) NAME/KEY: Peptide
        (B) LOCATION: 5
        (D) OTHER INFORMATION: /note = "Amino acid is amidated at
            the C- terminal."

(xi) SEQUENCE DESCRIPTION: SEQ ID NO:40:

Tyr Ile Arg Leu Pro
1               5

(2) INFORMATION FOR SEQ ID NO:41:

(i) SEQUENCE CHARACTERISTICS:
        (A) LENGTH: 5 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note = "N-terminal is CH-3OCO."

(ix) FEATURE:

(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:41:

Tyr Ile Arg Leu Pro
1               5

(2) INFORMATION FOR SEQ ID NO:42:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Xaa is Nal(2)."

(ix) FEATURE:
(A) NAME/KEY: Peptide
(B) LOCATION: 2
(D) OTHER INFORMATION: /note = "Xaa is Cha."

(ix) FEATURE:
(A) NAME/KEY: Peptide
(B) LOCATION: 4
(D) OTHER INFORMATION: /note = "Asp has an O-Allyl group."

(ix) FEATURE:
(A) NAME/KEY: Peptide
(B) LOCATION: 4
(D) OTHER INFORMATION: /note = "Amino acid is amidated at the C- terminal."

(xi) SEQUENCE DESCRIPTION: SEQ ID NO:42:

Xaa Xaa Arg Asp
1

(2) INFORMATION FOR SEQ ID NO:43:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Phe has a (pF) group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:43:

Phe Ile Arg Leu Pro
1               5

(2) INFORMATION FOR SEQ ID NO:44:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Xaa is (D)Tic(OH)."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:44:

Xaa Ile Arg Leu Pro
1                 5

( 2 ) INFORMATION FOR SEQ ID NO:45:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has a pCN group."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:45:

Phe Ile Arg Leu Pro
1                 5

( 2 ) INFORMATION FOR SEQ ID NO:46:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has a pCONH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:46:

Phe Xaa Arg Leu Pro
1               5

( 2 ) INFORMATION FOR SEQ ID NO:47:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:47:

Trp Xaa Arg Leu Pro
1               5

( 2 ) INFORMATION FOR SEQ ID NO:48:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 2
        ( D ) OTHER INFORMATION: /note = "Xaa is Pgl."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:48:

Tyr Xaa Arg Leu Pro
1               5

( 2 ) INFORMATION FOR SEQ ID NO:49:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 2

( D ) OTHER INFORMATION: /note = "Xaa is Chg."

( i x ) FEATURE:
    ( A ) NAME/KEY: Peptide
    ( B ) LOCATION: 4
    ( D ) OTHER INFORMATION: /note = "Xaa is Ina."

( i x ) FEATURE:
    ( A ) NAME/KEY: Peptide
    ( B ) LOCATION: 4
    ( D ) OTHER INFORMATION: /note = "Amino acid is amidated at the C- terminal."

( x i ) SEQUENCE DESCRIPTION: SEQ ID NO:49:

Tyr Xaa Arg Xaa
1

( 2 ) INFORMATION FOR SEQ ID NO:50:

( i ) SEQUENCE CHARACTERISTICS:
    ( A ) LENGTH: 5 amino acids
    ( B ) TYPE: amino acid
    ( D ) TOPOLOGY: linear ( x i ) SEQUENCE DESCRIPTION: SEQ ID NO:50:

Tyr Ile Arg Leu Pro
1               5

( 2 ) INFORMATION FOR SEQ ID NO:51:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Tyr has a 2,2-DiMe-Propyl group."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:51:

Tyr Ile Arg Leu Pro
1               5

( 2 ) INFORMATION FOR SEQ ID NO:52:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Tyr has a 2-CF-3-Bzl group."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:52:

Tyr Ile Arg Leu Pro
1               5

( 2 ) INFORMATION FOR SEQ ID NO:53:

( i ) SEQUENCE CHARACTERISTICS:
       ( A ) LENGTH: 5 amino acids
       ( B ) TYPE: amino acid
       ( D ) TOPOLOGY: linear ( i x ) FEATURE:
       ( A ) NAME/KEY: Peptide
       ( B ) LOCATION: 1
       ( D ) OTHER INFORMATION: /note = "Tyr has a 2-Et-nBu group."

( i x ) FEATURE:
       ( A ) NAME/KEY: Peptide
       ( B ) LOCATION: 5
       ( D ) OTHER INFORMATION: /note = "Amino acid is amidated at
             the C- terminal."

( x i ) SEQUENCE DESCRIPTION: SEQ ID NO:53:

Tyr  Ile  Arg  Leu  Pro
   1                    5

( 2 ) INFORMATION FOR SEQ ID NO:54:

( i ) SEQUENCE CHARACTERISTICS:
       ( A ) LENGTH: 5 amino acids
       ( B ) TYPE: amino acid
       ( D ) TOPOLOGY: linear ( i x ) FEATURE:
       ( A ) NAME/KEY: Peptide
       ( B ) LOCATION: 1
       ( D ) OTHER INFORMATION: /note = "Tyr has a 2-Me-Bzl group."

( i x ) FEATURE:
       ( A ) NAME/KEY: Peptide
       ( B ) LOCATION: 5
       ( D ) OTHER INFORMATION: /note = "Amino acid is amidated at
             the C- terminal."

( x i ) SEQUENCE DESCRIPTION: SEQ ID NO:54:

Tyr  Ile  Arg  Leu  Pro
   1                    5

( 2 ) INFORMATION FOR SEQ ID NO:55:

( i ) SEQUENCE CHARACTERISTICS:
       ( A ) LENGTH: 5 amino acids
       ( B ) TYPE: amino acid
       ( D ) TOPOLOGY: linear ( i x ) FEATURE:
       ( A ) NAME/KEY: Peptide
       ( B ) LOCATION: 1
       ( D ) OTHER INFORMATION: /note = "Tyr has a 2-Me-nBu group."

( i x ) FEATURE:
       ( A ) NAME/KEY: Peptide
       ( B ) LOCATION: 5
       ( D ) OTHER INFORMATION: /note = "Amino acid is amidated at
             the C- terminal."

( x i ) SEQUENCE DESCRIPTION: SEQ ID NO:55:

Tyr  Ile  Arg  Leu  Pro
   1                    5

( 2 ) INFORMATION FOR SEQ ID NO:56:

( i ) SEQUENCE CHARACTERISTICS:
       ( A ) LENGTH: 5 amino acids
       ( B ) TYPE: amino acid
       ( D ) TOPOLOGY: linear ( i x ) FEATURE:
  ( A ) NAME/KEY: Peptide
  ( B ) LOCATION: 1
  ( D ) OTHER INFORMATION: /note = "Tyr has a 2-Me-nPentyl group."

( i x ) FEATURE:
  ( A ) NAME/KEY: Peptide
  ( B ) LOCATION: 5
  ( D ) OTHER INFORMATION: /note = "Amino acid is amidated at the C- terminal."

( x i ) SEQUENCE DESCRIPTION: SEQ ID NO:56:

Tyr Ile Arg Leu Pro
1               5

( 2 ) INFORMATION FOR SEQ ID NO:57:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Tyr has a 3,3-DiMe-nBu group."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:57:

Tyr Ile Arg Leu Pro
1               5

( 2 ) INFORMATION FOR SEQ ID NO:58:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "N-terminal is 5-Bzim-CO."

( i x ) FEATURE:
    ( A ) NAME/KEY: Peptide
    ( B ) LOCATION: 1
    ( D ) OTHER INFORMATION: /note = "Xaa is Chg."

( i x ) FEATURE:
    ( A ) NAME/KEY: Peptide
    ( B ) LOCATION: 4
    ( D ) OTHER INFORMATION: /note = "Amino acid is amidated at the C- terminal."

( x i ) SEQUENCE DESCRIPTION: SEQ ID NO:58:

Xaa Arg Leu Pro
1

( 2 ) INFORMATION FOR SEQ ID NO:59:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "N-terminal is 5-Bzim-CO."

( i x ) FEATURE:
    ( A ) NAME/KEY: Peptide
    ( B ) LOCATION: 1
    ( D ) OTHER INFORMATION: /note = "Phe has a pNH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:59:

Phe Xaa Arg Leu Pro
1                5

( 2 ) INFORMATION FOR SEQ ID NO:60:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
    ( A ) NAME/KEY: Peptide
    ( B ) LOCATION: 1
    ( D ) OTHER INFORMATION: /note = "Tyr has a 3,5-Br group."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:60:

Tyr Ile Arg Leu Pro
1                5

( 2 ) INFORMATION FOR SEQ ID NO:61:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
    ( A ) NAME/KEY: Peptide
    ( B ) LOCATION: 1
    ( D ) OTHER INFORMATION: /note = "Tyr has a 3,5-I group."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:61:

Tyr Ile Arg Leu Pro
1                5

( 2 ) INFORMATION FOR SEQ ID NO:62:

( i ) SEQUENCE CHARACTERISTICS:
        ( A ) LENGTH: 5 amino acids
        ( B ) TYPE: amino acid ( D ) TOPOLOGY: linear ( i x ) FEATURE:
    ( A ) NAME/KEY: Peptide
    ( B ) LOCATION: 1
    ( D ) OTHER INFORMATION: /note = "Tyr has a Chx-Ch-2 group."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:62:

Tyr Ile Arg Leu Pro
1                    5

( 2 ) INFORMATION FOR SEQ ID NO:63:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Tyr has a iBu group."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:63:

Tyr Ile Arg Leu Ala
1                    5

( 2 ) INFORMATION FOR SEQ ID NO:64:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Tyr has an iBu group."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:64:

Tyr Ile Arg Leu Pro
1                    5

( 2 ) INFORMATION FOR SEQ ID NO:65:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Tyr has a methyl group."

( i x ) FEATURE:

(A) NAME/KEY: Peptide
                (B) LOCATION: 5
                (D) OTHER INFORMATION: /note = "Amino acid is amidated at
                    the C- terminal."

(xi) SEQUENCE DESCRIPTION: SEQ ID NO:65:

Tyr  Ile  Arg  Leu  Ala
    1                   5

(2) INFORMATION FOR SEQ ID NO:66:

(i) SEQUENCE CHARACTERISTICS:
            (A) LENGTH: 5 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note = "Tyr has a methyl group."

(ix) FEATURE:
            (A) NAME/KEY: Peptide
            (B) LOCATION: 5
            (D) OTHER INFORMATION: /note = "Amino acid is amidated at
                the C- terminal."

(xi) SEQUENCE DESCRIPTION: SEQ ID NO:66:

Tyr  Ile  Arg  Leu  Pro
    1                   5

(2) INFORMATION FOR SEQ ID NO:67:

(i) SEQUENCE CHARACTERISTICS:
            (A) LENGTH: 5 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note = "Amino acid is acetylated at
                the N- terminal."

(ix) FEATURE:
            (A) NAME/KEY: Peptide
            (B) LOCATION: 1
            (D) OTHER INFORMATION: /note = "Tyr has a 1,2,3,6-4H-Bzl
                group and an SO-3H group."

(ix) FEATURE:
            (A) NAME/KEY: Peptide
            (B) LOCATION: 5
            (D) OTHER INFORMATION: /note = "Amino acid is amidated at
                the C- terminal."

(xi) SEQUENCE DESCRIPTION: SEQ ID NO:67:

Tyr  Ile  Arg  Leu  Pro
    1                   5

(2) INFORMATION FOR SEQ ID NO:68:

(i) SEQUENCE CHARACTERISTICS:
            (A) LENGTH: 5 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note = "Amino acid is acetylated at
                the N- terminal."

(ix) FEATURE:

(A) NAME/KEY: Peptide
                        (B) LOCATION: 1
                        (D) OTHER INFORMATION: /note = "Tyr has a 1,2,3,6-4H-Bzl
                            group."

(ix) FEATURE:
                        (A) NAME/KEY: Peptide
                        (B) LOCATION: 5
                        (D) OTHER INFORMATION: /note = "Amino acid is amidated at
                            the C- terminal."

(xi) SEQUENCE DESCRIPTION: SEQ ID NO:68:

Tyr  Ile  Arg  Leu  Pro
        1                    5

(2) INFORMATION FOR SEQ ID NO:69:

(i) SEQUENCE CHARACTERISTICS:
                        (A) LENGTH: 5 amino acids
                        (B) TYPE: amino acid
                        (D) TOPOLOGY: linear (ix) FEATURE:
                        (A) NAME/KEY: Peptide
                        (B) LOCATION: 1
                        (D) OTHER INFORMATION: /note = "Amino acid is acetylated at
                            the N- terminal."

(ix) FEATURE:
                        (A) NAME/KEY: Peptide
                        (B) LOCATION: 1
                        (D) OTHER INFORMATION: /note = "Tyr has a 2,3-DiMe-nPentyl
                            group and an SO-3H group."

(ix) FEATURE:
                        (A) NAME/KEY: Peptide
                        (B) LOCATION: 5
                        (D) OTHER INFORMATION: /note = "Amino acid is amidated at
                            the C- terminal."

(xi) SEQUENCE DESCRIPTION: SEQ ID NO:69:

Tyr  Ile  Arg  Leu  Pro
        1                    5

(2) INFORMATION FOR SEQ ID NO:70:

(i) SEQUENCE CHARACTERISTICS:
                        (A) LENGTH: 5 amino acids
                        (B) TYPE: amino acid
                        (D) TOPOLOGY: linear (ix) FEATURE:
                        (A) NAME/KEY: Peptide
                        (B) LOCATION: 1
                        (D) OTHER INFORMATION: /note = "Amino acid is acetylated at
                            the N- terminal."

(ix) FEATURE:
                        (A) NAME/KEY: Peptide
                        (B) LOCATION: 1
                        (D) OTHER INFORMATION: /note = "Tyr has a 2,3-DiMe-nPentyl
                            group."

(ix) FEATURE:
                        (A) NAME/KEY: Peptide
                        (B) LOCATION: 5
                        (D) OTHER INFORMATION: /note = "Amino acid is amidated at
                            the C- terminal."

(xi) SEQUENCE DESCRIPTION: SEQ ID NO:70:

Tyr  Ile  Arg  Leu  Pro
        1                    5

(2) INFORMATION FOR SEQ ID NO:71:

( i ) SEQUENCE CHARACTERISTICS:
: ( A ) LENGTH: 5 amino acids
: ( B ) TYPE: amino acid
: ( D ) TOPOLOGY: linear ( i x ) FEATURE:
: ( A ) NAME/KEY: Peptide
: ( B ) LOCATION: 1
: ( D ) OTHER INFORMATION: /note = "Amino acid is acetylated at the N- terminal."

( i x ) FEATURE:
: ( A ) NAME/KEY: Peptide
: ( B ) LOCATION: 1
: ( D ) OTHER INFORMATION: /note = "Tyr has a 2-CF-3-Bzl group and an SO-3H group."

( i x ) FEATURE:
: ( A ) NAME/KEY: Peptide
: ( B ) LOCATION: 5
: ( D ) OTHER INFORMATION: /note = "Amino acid is amidated at the C- terminal."

( x i ) SEQUENCE DESCRIPTION: SEQ ID NO:71:

Tyr Ile Arg Leu Pro
1               5

( 2 ) INFORMATION FOR SEQ ID NO:72:

( i ) SEQUENCE CHARACTERISTICS:
: ( A ) LENGTH: 5 amino acids
: ( B ) TYPE: amino acid
: ( D ) TOPOLOGY: linear ( i x ) FEATURE:
: ( A ) NAME/KEY: Peptide
: ( B ) LOCATION: 1
: ( D ) OTHER INFORMATION: /note = "Amino acid is acetylated at the N- terminal."

( i x ) FEATURE:
: ( A ) NAME/KEY: Peptide
: ( B ) LOCATION: 1
: ( D ) OTHER INFORMATION: /note = "Tyr has a 2-CF-3-Bzl group."

( i x ) FEATURE:
: ( A ) NAME/KEY: Peptide
: ( B ) LOCATION: 5
: ( D ) OTHER INFORMATION: /note = "Amino acid is amidated at the C- terminal."

( x i ) SEQUENCE DESCRIPTION: SEQ ID NO:72:

Tyr Ile Arg Leu Pro
1               5

( 2 ) INFORMATION FOR SEQ ID NO:73:

( i ) SEQUENCE CHARACTERISTICS:
: ( A ) LENGTH: 5 amino acids
: ( B ) TYPE: amino acid
: ( D ) TOPOLOGY: linear ( i x ) FEATURE:
: ( A ) NAME/KEY: Peptide
: ( B ) LOCATION: 1
: ( D ) OTHER INFORMATION: /note = "Amino acid is acetylated at the N- terminal."

( i x ) FEATURE:
: ( A ) NAME/KEY: Peptide
: ( B ) LOCATION: 1
: ( D ) OTHER INFORMATION: /note = "Tyr has a 2Et-nBu group."

( i x ) FEATURE:

(A) NAME/KEY: Peptide
                    (B) LOCATION: 5
                    (D) OTHER INFORMATION: /note = "Amino acid is amidated at
                        the C- terminal."

(xi) SEQUENCE DESCRIPTION: SEQ ID NO:73:

Tyr  Ile  Arg  Leu  Pro
        1                   5

(2) INFORMATION FOR SEQ ID NO:74:

(i) SEQUENCE CHARACTERISTICS:
                    (A) LENGTH: 5 amino acids
                    (B) TYPE: amino acid
                    (D) TOPOLOGY: linear (ix) FEATURE:
                    (A) NAME/KEY: Peptide
                    (B) LOCATION: 1
                    (D) OTHER INFORMATION: /note = "Amino acid is acetylated at
                        the N- terminal."

(ix) FEATURE:
                    (A) NAME/KEY: Peptide
                    (B) LOCATION: 1
                    (D) OTHER INFORMATION: /note = "Tyr has a 2-Me-Bzl group
                        and a SO-3H group."

(ix) FEATURE:
                    (A) NAME/KEY: Peptide
                    (B) LOCATION: 5
                    (D) OTHER INFORMATION: /note = "Amino acid is amidated at
                        the C- terminal."

(xi) SEQUENCE DESCRIPTION: SEQ ID NO:74:

Tyr  Ile  Arg  Leu  Pro
        1                   5

(2) INFORMATION FOR SEQ ID NO:75:

(i) SEQUENCE CHARACTERISTICS:
                    (A) LENGTH: 5 amino acids
                    (B) TYPE: amino acid
                    (D) TOPOLOGY: linear (ix) FEATURE:
                    (A) NAME/KEY: Peptide
                    (B) LOCATION: 1
                    (D) OTHER INFORMATION: /note = "Amino acid is acetylated at
                        the N- terminal."

(ix) FEATURE:
                    (A) NAME/KEY: Peptide
                    (B) LOCATION: 1
                    (D) OTHER INFORMATION: /note = "Tyr has a 2-Me-Bzl group."

(ix) FEATURE:
                    (A) NAME/KEY: Peptide
                    (B) LOCATION: 5
                    (D) OTHER INFORMATION: /note = "Amino acid is amidated at
                        the C- terminal."

(xi) SEQUENCE DESCRIPTION: SEQ ID NO:75:

Tyr  Ile  Arg  Leu  Pro
        1                   5

(2) INFORMATION FOR SEQ ID NO:76:

(i) SEQUENCE CHARACTERISTICS:
                    (A) LENGTH: 5 amino acids
                    (B) TYPE: amino acid
                    (D) TOPOLOGY: linear (ix) FEATURE:

( A ) NAME/KEY: Peptide
                ( B ) LOCATION: 1
                ( D ) OTHER INFORMATION: /note = "Amino acid is acetylated at
                    the N- terminal."

( i x ) FEATURE:
                ( A ) NAME/KEY: Peptide
                ( B ) LOCATION: 1
                ( D ) OTHER INFORMATION: /note = "Tyr has a 2-Me-nBu group
                    and an SO-3H group."

( i x ) FEATURE:
                ( A ) NAME/KEY: Peptide
                ( B ) LOCATION: 5
                ( D ) OTHER INFORMATION: /note = "Amino acid is amidated at
                    the C- terminal."

( x i ) SEQUENCE DESCRIPTION: SEQ ID NO:76:

Tyr  Ile  Arg  Leu  Pro
    1                   5

( 2 ) INFORMATION FOR SEQ ID NO:77:

( i ) SEQUENCE CHARACTERISTICS:
                ( A ) LENGTH: 5 amino acids
                ( B ) TYPE: amino acid
                ( D ) TOPOLOGY: linear ( i x ) FEATURE:
                ( A ) NAME/KEY: Peptide
                ( B ) LOCATION: 1
                ( D ) OTHER INFORMATION: /note = "Amino acid is acetylated at
                    the N- terminal."

( i x ) FEATURE:
                ( A ) NAME/KEY: Peptide
                ( B ) LOCATION: 1
                ( D ) OTHER INFORMATION: /note = "Tyr has a 2-Me-nBu group."

( i x ) FEATURE:
                ( A ) NAME/KEY: Peptide
                ( B ) LOCATION: 5
                ( D ) OTHER INFORMATION: /note = "Amino acid is amidated at
                    the C- terminal."

( x i ) SEQUENCE DESCRIPTION: SEQ ID NO:77:

Tyr  Ile  Arg  Leu  Pro
    1                   5

( 2 ) INFORMATION FOR SEQ ID NO:78:

( i ) SEQUENCE CHARACTERISTICS:
                ( A ) LENGTH: 5 amino acids
                ( B ) TYPE: amino acid
                ( D ) TOPOLOGY: linear ( i x ) FEATURE:
                ( A ) NAME/KEY: Peptide
                ( B ) LOCATION: 1
                ( D ) OTHER INFORMATION: /note = "Amino acid is acetylated at
                    the N- terminal."

( i x ) FEATURE:
                ( A ) NAME/KEY: Peptide
                ( B ) LOCATION: 1
                ( D ) OTHER INFORMATION: /note = "Tyr has a 2-Me-nPentyl
                    group and a SO-3H group."

( i x ) FEATURE:
                ( A ) NAME/KEY: Peptide
                ( B ) LOCATION: 5
                ( D ) OTHER INFORMATION: /note = "Amino acid is amidated at
                    the C- terminal."

( x i ) SEQUENCE DESCRIPTION: SEQ ID NO:78:

Tyr Ile Arg Leu Pro
1               5

( 2 ) INFORMATION FOR SEQ ID NO:79:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide
        ( B ) LOCATION: 1
        ( D ) OTHER INFORMATION: /note = "Tyr has a 2-Me-nPentyl
            group."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:79:

Tyr Ile Arg Leu Pro
1               5

( 2 ) INFORMATION FOR SEQ ID NO:80:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide
        ( B ) LOCATION: 1
        ( D ) OTHER INFORMATION: /note = "Tyr has a 3,3-DiMe-nBu
            group and a SO-3H group."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:80:

Tyr Ile Arg Leu Pro
1               5

( 2 ) INFORMATION FOR SEQ ID NO:81:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:

(A) NAME/KEY: Peptide
(B) LOCATION: 1
(D) OTHER INFORMATION: /note = "Tyr has a 3,3-DiMe-nBu group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:81:

Tyr Ile Arg Leu Pro
1               5

(2) INFORMATION FOR SEQ ID NO:82:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Tyr has a 3,3,-DiMe-nPentyl group and a SO-3H group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:82:

Tyr Ile Arg Leu Pro
1               5

(2) INFORMATION FOR SEQ ID NO:83:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Tyr has a 3,5,5-Me-3-nHexyl group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:83:

Tyr Ile Arg Leu Pro
1               5

(2) INFORMATION FOR SEQ ID NO:84:

( i ) SEQUENCE CHARACTERISTICS:
 ( A ) LENGTH: 5 amino acids
 ( B ) TYPE: amino acid
 ( D ) TOPOLOGY: linear ( i x ) FEATURE:
 ( A ) NAME/KEY: Peptide
 ( B ) LOCATION: 1
 ( D ) OTHER INFORMATION: /note = "Amino acid is acetylated at the N- terminal."

( i x ) FEATURE:
 ( A ) NAME/KEY: Peptide
 ( B ) LOCATION: 1
 ( D ) OTHER INFORMATION: /note = "Tyr has a Chx-CH-2 group."

( i x ) FEATURE:
 ( A ) NAME/KEY: Peptide
 ( B ) LOCATION: 5
 ( D ) OTHER INFORMATION: /note = "Amino acid is amidated at the C- terminal."

( x i ) SEQUENCE DESCRIPTION: SEQ ID NO:84:

Tyr Ile Arg Leu Pro
1      5

( 2 ) INFORMATION FOR SEQ ID NO:85:

( i ) SEQUENCE CHARACTERISTICS:
 ( A ) LENGTH: 5 amino acids
 ( B ) TYPE: amino acid
 ( D ) TOPOLOGY: linear ( i x ) FEATURE:
 ( A ) NAME/KEY: Peptide
 ( B ) LOCATION: 1
 ( D ) OTHER INFORMATION: /note = "Amino acid is acetylated at the N- terminal."

( i x ) FEATURE:
 ( A ) NAME/KEY: Peptide
 ( B ) LOCATION: 1
 ( D ) OTHER INFORMATION: /note = "Tyr has a Cyclopropyl-CH-2 group and an SO-3H group."

( i x ) FEATURE:
 ( A ) NAME/KEY: Peptide
 ( B ) LOCATION: 5
 ( D ) OTHER INFORMATION: /note = "Amino acid is amidated at the C- terminal."

( x i ) SEQUENCE DESCRIPTION: SEQ ID NO:85:

Tyr Ile Arg Leu Pro
1      5

( 2 ) INFORMATION FOR SEQ ID NO:86:

( i ) SEQUENCE CHARACTERISTICS:
 ( A ) LENGTH: 5 amino acids
 ( B ) TYPE: amino acid
 ( D ) TOPOLOGY: linear ( i x ) FEATURE:
 ( A ) NAME/KEY: Peptide
 ( B ) LOCATION: 1
 ( D ) OTHER INFORMATION: /note = "Amino acid is acetylated at the N- terminal."

( i x ) FEATURE:
 ( A ) NAME/KEY: Peptide
 ( B ) LOCATION: 1
 ( D ) OTHER INFORMATION: /note = "Tyr has a Cyclopropyl-CH-2 group."

( i x ) FEATURE:

(A) NAME/KEY: Peptide
(B) LOCATION: 5
(D) OTHER INFORMATION: /note = "Amino acid is amidated at
the C- terminal."

(x i) SEQUENCE DESCRIPTION: SEQ ID NO:86:

Tyr Ile Arg Leu Pro
1               5

(2) INFORMATION FOR SEQ ID NO:87:

(i) SEQUENCE CHARACTERISTICS:
(A) LENGTH: 5 amino acids
(B) TYPE: amino acid
(D) TOPOLOGY: linear (i x) FEATURE:
(A) NAME/KEY: Peptide
(B) LOCATION: 1
(D) OTHER INFORMATION: /note = "Amino acid is acetylated at
the N- terminal."

(i x) FEATURE:
(A) NAME/KEY: Peptide
(B) LOCATION: 1
(D) OTHER INFORMATION: /note = "Tyr has an
Et-CH=C(CH-3)-CH-2 group and an SO-3H group."

(i x) FEATURE:
(A) NAME/KEY: Peptide
(B) LOCATION: 5
(D) OTHER INFORMATION: /note = "Amino acid is amidated at
the C- terminal."

(x i) SEQUENCE DESCRIPTION: SEQ ID NO:87:

Tyr Ile Arg Leu Pro
1               5

(2) INFORMATION FOR SEQ ID NO:88:

(i) SEQUENCE CHARACTERISTICS:
(A) LENGTH: 5 amino acids
(B) TYPE: amino acid
(D) TOPOLOGY: linear (i x) FEATURE:
(A) NAME/KEY: Peptide
(B) LOCATION: 1
(D) OTHER INFORMATION: /note = "Amino acid is acetylated at
the N- terminal."

(i x) FEATURE:
(A) NAME/KEY: Peptide
(B) LOCATION: 1
(D) OTHER INFORMATION: /note = "Tyr has an
Et-CH=C(CH-3)-CH-2 group."

(i x) FEATURE:
(A) NAME/KEY: Peptide
(B) LOCATION: 5
(D) OTHER INFORMATION: /note = "Amino acid is amidated at
the C- terminal."

(x i) SEQUENCE DESCRIPTION: SEQ ID NO:88:

Tyr Ile Arg Leu Pro
1               5

(2) INFORMATION FOR SEQ ID NO:89:

(i) SEQUENCE CHARACTERISTICS:
(A) LENGTH: 5 amino acids
(B) TYPE: amino acid
(D) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has an iBu group and a pNH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:89:

Phe Xaa Arg Leu Pro
1               5

( 2 ) INFORMATION FOR SEQ ID NO:90:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 1
        ( D ) OTHER INFORMATION: /note = "Xaa is (iBu)Nal(2)."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:90:

Xaa Xaa Arg Leu Pro
1               5

( 2 ) INFORMATION FOR SEQ ID NO:91:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 1

(D) OTHER INFORMATION: /note = "Tyr has an iBu group."

(ix) FEATURE:
                (A) NAME/KEY: Peptide
                (B) LOCATION: 2
                (D) OTHER INFORMATION: /note = "Xaa is Chg."

(ix) FEATURE:
                (A) NAME/KEY: Peptide
                (B) LOCATION: 5
                (D) OTHER INFORMATION: /note = "Amino acid is amidated at
                        the C- terminal."

(xi) SEQUENCE DESCRIPTION: SEQ ID NO:91:

Tyr   Xaa   Arg   Leu   Pro
    1                       5

(2) INFORMATION FOR SEQ ID NO:92:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note = "Amino acid is acetylated at
                        the N- terminal."

(ix) FEATURE:
                (A) NAME/KEY: Peptide
                (B) LOCATION: 1
                (D) OTHER INFORMATION: /note = "Tyr has an iBu group."

(ix) FEATURE:
                (A) NAME/KEY: Peptide
                (B) LOCATION: 3
                (D) OTHER INFORMATION: /note = "Xaa is Dab-derived
                        dimethylamidinium."

(ix) FEATURE:
                (A) NAME/KEY: Peptide
                (B) LOCATION: 5
                (D) OTHER INFORMATION: /note = "Amino acid is amidated at
                        the C- terminal."

(xi) SEQUENCE DESCRIPTION: SEQ ID NO:92:

Tyr   Ile   Xaa   Leu   Pro
    1                       5

(2) INFORMATION FOR SEQ ID NO:93:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note = "Amino acid is acetylated at
                        the N- terminal."

(ix) FEATURE:
                (A) NAME/KEY: Peptide
                (B) LOCATION: 1
                (D) OTHER INFORMATION: /note = "Tyr has an iBu group."

(ix) FEATURE:
                (A) NAME/KEY: Peptide
                (B) LOCATION: 3
                (D) OTHER INFORMATION: /note = "Xaa is Ornithine-derived
                        dimethylamidinium."

(ix) FEATURE:

(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:93:

Tyr Ile Xaa Leu Pro
1               5

(2) INFORMATION FOR SEQ ID NO:94:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Tyr has an iBu group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:94:

Tyr Ile Arg Leu Pro
1               5

(2) INFORMATION FOR SEQ ID NO:95:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Tyr has an O-methyl group."

(ix) FEATURE:
(A) NAME/KEY: Peptide
(B) LOCATION: 2
(D) OTHER INFORMATION: /note = "Xaa is Chg."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:95:

Tyr Xaa Arg Leu Pro
1               5

(2) INFORMATION FOR SEQ ID NO:96:

(i) SEQUENCE CHARACTERISTICS:
(A) LENGTH: 5 amino acids (B) TYPE: amino acid
(D) TOPOLOGY: linear (ix) FEATURE:
 (A) NAME/KEY: Peptide
 (B) LOCATION: 1
 (D) OTHER INFORMATION: /note = "Amino acid is acetylated at the N- terminal."

(ix) FEATURE:
 (A) NAME/KEY: Peptide
 (B) LOCATION: 1
 (D) OTHER INFORMATION: /note = "Tyr has an O-methyl group."

(ix) FEATURE:
 (A) NAME/KEY: Peptide
 (B) LOCATION: 5
 (D) OTHER INFORMATION: /note = "Amino acid is amidated at the C- terminal."

(xi) SEQUENCE DESCRIPTION: SEQ ID NO:96:

```
Tyr  Ile  Arg  Leu  Ala
1                    5
```

(2) INFORMATION FOR SEQ ID NO:97:

(i) SEQUENCE CHARACTERISTICS:
  (A) LENGTH: 5 amino acids
  (B) TYPE: amino acid
  (D) TOPOLOGY: linear (ix) FEATURE:
 (A) NAME/KEY: Peptide
 (B) LOCATION: 1
 (D) OTHER INFORMATION: /note = "Amino acid is acetylated at the N- terminal."

(ix) FEATURE:
 (A) NAME/KEY: Peptide
 (B) LOCATION: 1
 (D) OTHER INFORMATION: /note = "Tyr has an O-methyl group."

(ix) FEATURE:
 (A) NAME/KEY: Peptide
 (B) LOCATION: 5
 (D) OTHER INFORMATION: /note = "Amino acid is amidated at the C- terminal."

(xi) SEQUENCE DESCRIPTION: SEQ ID NO:97:

```
Tyr  Ile  Arg  Leu  Pro
1                    5
```

(2) INFORMATION FOR SEQ ID NO:98:

(i) SEQUENCE CHARACTERISTICS:
  (A) LENGTH: 5 amino acids
  (B) TYPE: amino acid
  (D) TOPOLOGY: linear (ix) FEATURE:
 (A) NAME/KEY: Peptide
 (B) LOCATION: 1
 (D) OTHER INFORMATION: /note = "Amino acid is acetylated at the N- terminal."

(ix) FEATURE:
 (A) NAME/KEY: Peptide
 (B) LOCATION: 1
 (D) OTHER INFORMATION: /note = "Tyr has a trans-CH-3- CH=C(CH-3)-CH-2 group."

(ix) FEATURE:
 (A) NAME/KEY: Peptide
 (B) LOCATION: 5
 (D) OTHER INFORMATION: /note = "Amino acid is amidated at the C- terminal."

( x i ) SEQUENCE DESCRIPTION: SEQ ID NO:98:

Tyr Ile Arg Leu Pro
1               5

( 2 ) INFORMATION FOR SEQ ID NO:99:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 1
        ( D ) OTHER INFORMATION: /note = "Tyr has a 3,5-NO-2 group."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:99:

Tyr Ile Arg Leu Pro
1               5

( 2 ) INFORMATION FOR SEQ ID NO:100:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 1
        ( D ) OTHER INFORMATION: /note = "Xaa is beta-alanine."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:100:

Xaa Tyr Ile Arg Gly
1               5

( 2 ) INFORMATION FOR SEQ ID NO:101:

( i ) SEQUENCE CHARACTERISTICS:
        ( A ) LENGTH: 6 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
  ( A ) NAME/KEY: Peptide
  ( B ) LOCATION: 6
  ( D ) OTHER INFORMATION: /note = "Amino acid is amidated at the C- terminal."

( x i ) SEQUENCE DESCRIPTION: SEQ ID NO:101:

Glu Tyr Ile Arg Leu Lys
1               5

( 2 ) INFORMATION FOR SEQ ID NO:102:

( i ) SEQUENCE CHARACTERISTICS:
    ( A ) LENGTH: 7 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 7
    ( D ) OTHER INFORMATION: /note = "Amino acid is amidated at the C- terminal."

( x i ) SEQUENCE DESCRIPTION: SEQ ID NO:102:

Glu Tyr Ile Arg Leu Pro Lys
1               5

( 2 ) INFORMATION FOR SEQ ID NO:103:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has a pCONH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:103:

Phe Xaa Arg Leu Pro
1               5

( 2 ) INFORMATION FOR SEQ ID NO:104:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:

(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Phe has a pCONH-2 group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:104:

Phe Ile Arg Leu Pro
1               5

(2) INFORMATION FOR SEQ ID NO:105:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Phe has a pF group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:105:

Phe Ile Arg Leu Pro
1               5

(2) INFORMATION FOR SEQ ID NO:106:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Phe has a pCN group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:106:

Phe Ile Arg Leu Pro
1               5

( 2 ) INFORMATION FOR SEQ ID NO:107:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide
        ( B ) LOCATION: 1
        ( D ) OTHER INFORMATION: /note = "Phe has a pNH-2 group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:107:

Phe Xaa Arg Leu Pro
1               5

( 2 ) INFORMATION FOR SEQ ID NO:108:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide
        ( B ) LOCATION: 1
        ( D ) OTHER INFORMATION: /note = "Phe has a pNH-2 group."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:108:

Phe Ile Arg Leu Pro
1               5

( 2 ) INFORMATION FOR SEQ ID NO:109:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
    ( A ) NAME/KEY: Peptide
    ( B ) LOCATION: 1
    ( D ) OTHER INFORMATION: /note = "Phe has a pNH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 4
    ( D ) OTHER INFORMATION: /note = "Gly has a Bzl group."

( x i ) SEQUENCE DESCRIPTION: SEQ ID NO:109:

Phe Xaa Arg Gly Gly
1               5

( 2 ) INFORMATION FOR SEQ ID NO:110:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has a pNH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 4
    ( D ) OTHER INFORMATION: /note = "Gly has a Chx group."

( x i ) SEQUENCE DESCRIPTION: SEQ ID NO:110:

Phe Xaa Arg Gly Gly
1               5

( 2 ) INFORMATION FOR SEQ ID NO:111:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has a pNH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide ( B ) LOCATION: 4
                ( D ) OTHER INFORMATION: /note = "Gly has a
                        CH-3CH-2CH- 2(CH-3) group."

( x i ) SEQUENCE DESCRIPTION: SEQ ID NO:111:

Phe   Xaa   Arg   Gly   Gly
    1                       5

( 2 ) INFORMATION FOR SEQ ID NO:112:

( i ) SEQUENCE CHARACTERISTICS:
            ( A ) LENGTH: 6 amino acids
            ( B ) TYPE: amino acid
            ( D ) TOPOLOGY: linear ( i x ) FEATURE:
            ( A ) NAME/KEY: Peptide
            ( B ) LOCATION: 1
            ( D ) OTHER INFORMATION: /note = "Amino acid is acetylated at
                    the N- terminal."

( i x ) FEATURE:
            ( A ) NAME/KEY: Peptide
            ( B ) LOCATION: 6
            ( D ) OTHER INFORMATION: /note = "Amino acid is amidated at
                    the C- terminal."

( x i ) SEQUENCE DESCRIPTION: SEQ ID NO:112:

Gly   Gly   Tyr   Ile   Arg   Gly
    1                       5

( 2 ) INFORMATION FOR SEQ ID NO:113:

( i ) SEQUENCE CHARACTERISTICS:
            ( A ) LENGTH: 5 amino acids
            ( B ) TYPE: amino acid
            ( D ) TOPOLOGY: linear ( i x ) FEATURE:
            ( A ) NAME/KEY: Peptide
            ( B ) LOCATION: 1
            ( D ) OTHER INFORMATION: /note = "Amino acid is acetylated at
                    the N- terminal."

( i x ) FEATURE:
            ( A ) NAME/KEY: Peptide
            ( B ) LOCATION: 3
            ( D ) OTHER INFORMATION: /note = "Xaa is Nle."

( i x ) FEATURE:
            ( A ) NAME/KEY: Peptide
            ( B ) LOCATION: 5
            ( D ) OTHER INFORMATION: /note = "Amino acid is amidated at
                    the C- terminal."

( x i ) SEQUENCE DESCRIPTION: SEQ ID NO:113:

Gly   Tyr   Xaa   Arg   Leu
    1                       5

( 2 ) INFORMATION FOR SEQ ID NO:114:

( i ) SEQUENCE CHARACTERISTICS:
            ( A ) LENGTH: 5 amino acids
            ( B ) TYPE: amino acid
            ( D ) TOPOLOGY: linear ( i x ) FEATURE:
            ( A ) NAME/KEY: Peptide
            ( B ) LOCATION: 1
            ( D ) OTHER INFORMATION: /note = "Amino acid is acetylated at
                    the N- terminal."

( i x ) FEATURE:
            ( A ) NAME/KEY: Peptide ( B ) LOCATION: 5
        ( D ) OTHER INFORMATION: /note = "Amino acid is amidated at
            the C- terminal."

( x i ) SEQUENCE DESCRIPTION: SEQ ID NO:114:

Gly  Tyr  Ile  Arg  Gly
    1                    5

( 2 ) INFORMATION FOR SEQ ID NO:115:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:115:

Gly  Tyr  Ile  Arg  Leu
    1                    5

( 2 ) INFORMATION FOR SEQ ID NO:116:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide
        ( B ) LOCATION: 1
        ( D ) OTHER INFORMATION: /note = "Xaa is Nal(1)."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:116:

Xaa  Ile  Arg  Leu  Pro
    1                    5

( 2 ) INFORMATION FOR SEQ ID NO:117:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide (B) LOCATION: 1
(D) OTHER INFORMATION: /note = "Xaa is Nal(2)."

(ix) FEATURE:
(A) NAME/KEY: Peptide
(B) LOCATION: 2
(D) OTHER INFORMATION: /note = "Xaa is Cha."

(ix) FEATURE:
(A) NAME/KEY: Peptide
(B) LOCATION: 4
(D) OTHER INFORMATION: /note = "Asp has an O-allyl group."

(ix) FEATURE:
(A) NAME/KEY: Peptide
(B) LOCATION: 4
(D) OTHER INFORMATION: /note = "Amino acid is amidated at the C- terminal."

(xi) SEQUENCE DESCRIPTION: SEQ ID NO:117:

Xaa Xaa Arg Asp
1

(2) INFORMATION FOR SEQ ID NO:118:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Xaa is Nal(2)."

(ix) FEATURE:
(A) NAME/KEY: Peptide
(B) LOCATION: 2
(D) OTHER INFORMATION: /note = "Xaa is Cha."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:118:

Xaa Xaa Arg Leu Pro
1               5

(2) INFORMATION FOR SEQ ID NO:119:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Xaa is Nal(2)."

(ix) FEATURE:
(A) NAME/KEY: Peptide (B) LOCATION: 2
(D) OTHER INFORMATION: /note = "Xaa is Chg."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:119:

Xaa Xaa Arg Leu Pro
1               5

(2) INFORMATION FOR SEQ ID NO:120:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Xaa is Nal(2)."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:120:

Xaa Ile Arg Leu Pro
1               5

(2) INFORMATION FOR SEQ ID NO:121:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1
(D) OTHER INFORMATION: /note = "Xaa is Pgl(OH)."

(ix) FEATURE:
(A) NAME/KEY: Peptide
(B) LOCATION: 4
(D) OTHER INFORMATION: /note = "Amino acid is amidated at the C- terminal."

(xi) SEQUENCE DESCRIPTION: SEQ ID NO:121:

Xaa Ile Arg Leu
1

(2) INFORMATION FOR SEQ ID NO:122:

(i) SEQUENCE CHARACTERISTICS:
(A) LENGTH: 5 amino acids
(B) TYPE: amino acid (D) TOPOLOGY: linear (ix) FEATURE:
  (A) NAME/KEY: Peptide
  (B) LOCATION: 1
  (D) OTHER INFORMATION: /note = "Amino acid is acetylated at the N- terminal."

(ix) FEATURE:
  (A) NAME/KEY: Peptide
  (B) LOCATION: 1
  (D) OTHER INFORMATION: /note = "Phe has a p-amidino group."

(ix) FEATURE:
  (A) NAME/KEY: Peptide
  (B) LOCATION: 2
  (D) OTHER INFORMATION: /note = "Xaa is Chg."

(ix) FEATURE:
  (A) NAME/KEY: Peptide
  (B) LOCATION: 5
  (D) OTHER INFORMATION: /note = "Amino acid is amidated at the C- terminal."

(xi) SEQUENCE DESCRIPTION: SEQ ID NO:122:

Phe Xaa Arg Leu Pro
1        5

(2) INFORMATION FOR SEQ ID NO:123:

(i) SEQUENCE CHARACTERISTICS:
  (A) LENGTH: 5 amino acids
  (B) TYPE: amino acid
  (D) TOPOLOGY: linear (ix) FEATURE:
  (A) NAME/KEY: Peptide
  (B) LOCATION: 1
  (D) OTHER INFORMATION: /note = "Amino acid is acetylated at the N- terminal."

(ix) FEATURE:
  (A) NAME/KEY: Peptide
  (B) LOCATION: 1
  (D) OTHER INFORMATION: /note = "Phe has a p-amidino group."

(ix) FEATURE:
  (A) NAME/KEY: Peptide
  (B) LOCATION: 5
  (D) OTHER INFORMATION: /note = "Amino acid is amidated at the C- terminal."

(xi) SEQUENCE DESCRIPTION: SEQ ID NO:123:

Phe Ile Arg Leu Pro
1        5

(2) INFORMATION FOR SEQ ID NO:124:

(i) SEQUENCE CHARACTERISTICS:
  (A) LENGTH: 5 amino acids
  (B) TYPE: amino acid
  (D) TOPOLOGY: linear (ix) FEATURE:
  (A) NAME/KEY: Peptide
  (B) LOCATION: 1
  (D) OTHER INFORMATION: /note = "Amino acid is acetylated at the N- terminal."

(ix) FEATURE:
  (A) NAME/KEY: Peptide
  (B) LOCATION: 1
  (D) OTHER INFORMATION: /note = "Phe has a pGua group."

(ix) FEATURE:
  (A) NAME/KEY: Peptide (B) LOCATION: 5
(D) OTHER INFORMATION: /note = "Amino acid is amidated at the C- terminal."

(xi) SEQUENCE DESCRIPTION: SEQ ID NO:124:

Phe Ile Arg Leu Pro
1               5

(2) INFORMATION FOR SEQ ID NO:125:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 6
(D) OTHER INFORMATION: /note = "Amino acid is amidated at the C- terminal."

(xi) SEQUENCE DESCRIPTION: SEQ ID NO:125:

Ser Tyr Ile Arg Leu Pro
1               5

(2) INFORMATION FOR SEQ ID NO:126:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 2
(D) OTHER INFORMATION: /note = "Xaa is Chg."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:126:

Trp Xaa Arg Leu Pro
1               5

(2) INFORMATION FOR SEQ ID NO:127:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide (B) LOCATION: 5
(D) OTHER INFORMATION: /note = "Amino acid is amidated at the C- terminal."

(xi) SEQUENCE DESCRIPTION: SEQ ID NO:127:

Trp Leu Arg Leu Ala
1               5

(2) INFORMATION FOR SEQ ID NO:128:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 2
(D) OTHER INFORMATION: /note = "Ile has an allo group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:128:

Tyr Ile Arg Leu Pro
1               5

(2) INFORMATION FOR SEQ ID NO:129:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 2
(D) OTHER INFORMATION: /note = "Xaa is Cha."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:129:

Tyr Xaa Arg Leu Pro
1               5

(2) INFORMATION FOR SEQ ID NO:130:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1

(D) OTHER INFORMATION: /note = "Amino acid is acetylated at
the N- terminal."

(ix) FEATURE:
(A) NAME/KEY: Peptide
(B) LOCATION: 2
(D) OTHER INFORMATION: /note = "Xaa is Chg."

(ix) FEATURE:
(A) NAME/KEY: Peptide
(B) LOCATION: 5
(D) OTHER INFORMATION: /note = "Amino acid is amidated at
the C- terminal."

(xi) SEQUENCE DESCRIPTION: SEQ ID NO:130:

Tyr Xaa Arg Leu Pro
1               5

(2) INFORMATION FOR SEQ ID NO:131:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at
the N- terminal."

(ix) FEATURE:
(A) NAME/KEY: Peptide
(B) LOCATION: 2
(D) OTHER INFORMATION: /note = "Xaa is Chg."

(ix) FEATURE:
(A) NAME/KEY: Peptide
(B) LOCATION: 3
(D) OTHER INFORMATION: /note = "Arg has an NO-2 group."

(ix) FEATURE:
(A) NAME/KEY: Peptide
(B) LOCATION: 3..4
(D) OTHER INFORMATION: /note = "There is a pseudo peptide
bond (CH- 2NH) between Arg(NO-2) and Leu."

(ix) FEATURE:
(A) NAME/KEY: Peptide
(B) LOCATION: 4
(D) OTHER INFORMATION: /note = "Amino acid is amidated at
the C- terminal."

(xi) SEQUENCE DESCRIPTION: SEQ ID NO:131:

Tyr Xaa Arg Leu
1

(2) INFORMATION FOR SEQ ID NO:132:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at
the N- terminal."

(ix) FEATURE:
(A) NAME/KEY: Peptide
(B) LOCATION: 2
(D) OTHER INFORMATION: /note = "Xaa is Pen(Me)."

(ix) FEATURE:

(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:132:

Tyr Xaa Arg Leu Pro
1               5

(2) INFORMATION FOR SEQ ID NO:133:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 2
(D) OTHER INFORMATION: /note = "Xaa is Pgl."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:133:

Tyr Xaa Arg Leu Pro
1               5

(2) INFORMATION FOR SEQ ID NO:134:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 1..2
(D) OTHER INFORMATION: /note = "There is a pseudo peptide bond (CH- 2N(Ac)) between Tyr and Ile."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:134:

Tyr Ile Arg Leu Pro
1               5

(2) INFORMATION FOR SEQ ID NO:135:

(i) SEQUENCE CHARACTERISTICS:
(A) LENGTH: 5 amino acids
(B) TYPE: amino acid
(D) TOPOLOGY: linear (ix) FEATURE:

( A ) NAME/KEY: Peptide
                    ( B ) LOCATION: 1
                    ( D ) OTHER INFORMATION: /note = "Amino acid is acetylated at
                            the N- terminal."

( i x ) FEATURE:
                    ( A ) NAME/KEY: Peptide
                    ( B ) LOCATION: 1..2
                    ( D ) OTHER INFORMATION: /note = "There is a pseudo peptide
                            bond (CH- 2NH) between Tyr and Ile."

( i x ) FEATURE:
                    ( A ) NAME/KEY: Peptide
                    ( B ) LOCATION: 5
                    ( D ) OTHER INFORMATION: /note = "Amino acid is amidated at
                            the C- terminal."

( x i ) SEQUENCE DESCRIPTION: SEQ ID NO:135:

Tyr  Ile  Arg  Leu  Pro
    1                    5

( 2 ) INFORMATION FOR SEQ ID NO:136:

( i ) SEQUENCE CHARACTERISTICS:
                    ( A ) LENGTH: 5 amino acids
                    ( B ) TYPE: amino acid
                    ( D ) TOPOLOGY: linear ( i x ) FEATURE:
                    ( A ) NAME/KEY: Peptide
                    ( B ) LOCATION: 1
                    ( D ) OTHER INFORMATION: /note = "Amino acid is acetylated at
                            the N- terminal."

( i x ) FEATURE:
                    ( A ) NAME/KEY: Peptide
                    ( B ) LOCATION: 3..4
                    ( D ) OTHER INFORMATION: /note = "There is a pseudo peptide
                            bond (COCH- 2) between Arg and Gly."

( i x ) FEATURE:
                    ( A ) NAME/KEY: Peptide
                    ( B ) LOCATION: 5
                    ( D ) OTHER INFORMATION: /note = "Amino acid is amidated at
                            the C- terminal."

( x i ) SEQUENCE DESCRIPTION: SEQ ID NO:136:

Tyr  Ile  Arg  Gly  Pro
    1                    5

( 2 ) INFORMATION FOR SEQ ID NO:137:

( i ) SEQUENCE CHARACTERISTICS:
                    ( A ) LENGTH: 5 amino acids
                    ( B ) TYPE: amino acid
                    ( D ) TOPOLOGY: linear ( i x ) FEATURE:
                    ( A ) NAME/KEY: Peptide
                    ( B ) LOCATION: 1
                    ( D ) OTHER INFORMATION: /note = "Amino acid is acetylated at
                            the N- terminal."

( i x ) FEATURE:
                    ( A ) NAME/KEY: Peptide
                    ( B ) LOCATION: 3
                    ( D ) OTHER INFORMATION: /note = "Xaa is Dab-derived
                            dimethylamidinium."

( i x ) FEATURE:
                    ( A ) NAME/KEY: Peptide
                    ( B ) LOCATION: 5
                    ( D ) OTHER INFORMATION: /note = "Amino acid is amidated at
                            the C- terminal."

( x i ) SEQUENCE DESCRIPTION: SEQ ID NO:137:

```
        Tyr  Ile  Xaa  Leu  Ala
        1                  5
```

(2) INFORMATION FOR SEQ ID NO:138:

(i) SEQUENCE CHARACTERISTICS:
        (A) LENGTH: 5 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note = "Amino acid is acetylated at the N- terminal."

(ix) FEATURE:
        (A) NAME/KEY: Peptide
        (B) LOCATION: 3
        (D) OTHER INFORMATION: /note = "Xaa is hR."

(ix) FEATURE:
        (A) NAME/KEY: Peptide
        (B) LOCATION: 5
        (D) OTHER INFORMATION: /note = "Amino acid is amidated at the C- terminal."

(xi) SEQUENCE DESCRIPTION: SEQ ID NO:138:

```
        Tyr  Ile  Xaa  Leu  Ala
        1                  5
```

(2) INFORMATION FOR SEQ ID NO:139:

(i) SEQUENCE CHARACTERISTICS:
        (A) LENGTH: 5 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note = "Amino acid is acetylated at the N- terminal."

(ix) FEATURE:
        (A) NAME/KEY: Peptide
        (B) LOCATION: 3
        (D) OTHER INFORMATION: /note = "Xaa is nR."

(ix) FEATURE:
        (A) NAME/KEY: Peptide
        (B) LOCATION: 5
        (D) OTHER INFORMATION: /note = "Amino acid is amidated at the C- terminal."

(xi) SEQUENCE DESCRIPTION: SEQ ID NO:139:

```
        Tyr  Ile  Xaa  Leu  Ala
        1                  5
```

(2) INFORMATION FOR SEQ ID NO:140:

(i) SEQUENCE CHARACTERISTICS:
        (A) LENGTH: 5 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note = "Amino acid is acetylated at the N- terminal."

(ix) FEATURE:
        (A) NAME/KEY: Peptide ( B ) LOCATION: 3
( D ) OTHER INFORMATION: /note = "Xaa is PalMe(3)."

( i x ) FEATURE:
( A ) NAME/KEY: Peptide
( B ) LOCATION: 5
( D ) OTHER INFORMATION: /note = "Amino acid is amidated at
the C- terminal."

( x i ) SEQUENCE DESCRIPTION: SEQ ID NO:140:

Tyr Ile Xaa Leu Pro
1               5

( 2 ) INFORMATION FOR SEQ ID NO:141:

( i ) SEQUENCE CHARACTERISTICS:
( A ) LENGTH: 5 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note = "Amino acid is acetylated at
the N- terminal."

( i x ) FEATURE:
( A ) NAME/KEY: Peptide
( B ) LOCATION: 2..3
( D ) OTHER INFORMATION: /note = "There is a pseudo peptide
bond (CH- 2NH) between Ile and Arg."

( i x ) FEATURE:
( A ) NAME/KEY: Peptide
( B ) LOCATION: 5
( D ) OTHER INFORMATION: /note = "Amino acid is amidated at
the C- terminal."

( x i ) SEQUENCE DESCRIPTION: SEQ ID NO:141:

Tyr Ile Arg Leu Pro
1               5

( 2 ) INFORMATION FOR SEQ ID NO:142:

( i ) SEQUENCE CHARACTERISTICS:
( A ) LENGTH: 5 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note = "Amino acid is acetylated at
the N- terminal."

( i x ) FEATURE:
( A ) NAME/KEY: Peptide
( B ) LOCATION: 4
( D ) OTHER INFORMATION: /note = "Xaa is Nle."

( i x ) FEATURE:
( A ) NAME/KEY: Peptide
( B ) LOCATION: 5
( D ) OTHER INFORMATION: /note = "Xaa is Hyp."

( x i ) SEQUENCE DESCRIPTION: SEQ ID NO:142:

Tyr Ile Arg Xaa Xaa
1               5

( 2 ) INFORMATION FOR SEQ ID NO:143:

( i ) SEQUENCE CHARACTERISTICS:
( A ) LENGTH: 5 amino acids
( B ) TYPE: amino acid (D) TOPOLOGY: linear (ix) FEATURE:
            (A) NAME/KEY: Peptide
            (B) LOCATION: 1
            (D) OTHER INFORMATION: /note = "Amino acid is acetylated at
                    the N- terminal."

(ix) FEATURE:
            (A) NAME/KEY: Peptide
            (B) LOCATION: 4
            (D) OTHER INFORMATION: /note = "Xaa is Nle."

(ix) FEATURE:
            (A) NAME/KEY: Peptide
            (B) LOCATION: 5
            (D) OTHER INFORMATION: /note = "Xaa is delta 2-P."

(xi) SEQUENCE DESCRIPTION: SEQ ID NO:143:

Tyr  Ile  Arg  Xaa  Xaa
    1                   5

(2) INFORMATION FOR SEQ ID NO:144:

(i) SEQUENCE CHARACTERISTICS:
            (A) LENGTH: 4 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note = "Amino acid is acetylated at
                    the N- terminal."

(xi) SEQUENCE DESCRIPTION: SEQ ID NO:144:

Tyr  Ile  Arg  Ile
    1

(2) INFORMATION FOR SEQ ID NO:145:

(i) SEQUENCE CHARACTERISTICS:
            (A) LENGTH: 5 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note = "Amino acid is acetylated at
                    the N- terminal."

(xi) SEQUENCE DESCRIPTION: SEQ ID NO:145:

Tyr  Ile  Arg  Ile  Pro
    1                   5

(2) INFORMATION FOR SEQ ID NO:146:

(i) SEQUENCE CHARACTERISTICS:
            (A) LENGTH: 4 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note = "Amino acid is acetylated at
                    the N- terminal."

(xi) SEQUENCE DESCRIPTION: SEQ ID NO:146:

Tyr  Ile  Arg  Leu
    1

( 2 ) INFORMATION FOR SEQ ID NO:147:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( x i ) SEQUENCE DESCRIPTION: SEQ ID NO:147:

Tyr Ile Arg Leu Ala
    1                  5

( 2 ) INFORMATION FOR SEQ ID NO:148:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide
        ( B ) LOCATION: 8
        ( D ) OTHER INFORMATION: /note = "Amino acid is amidated at
            the C- terminal."

( x i ) SEQUENCE DESCRIPTION: SEQ ID NO:148:

Tyr Ile Arg Leu Ala Ala Phe Thr
    1                  5

( 2 ) INFORMATION FOR SEQ ID NO:149:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at
            the N- terminal."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:149:

Tyr Ile Arg Leu Pro
    1                  5

( 2 ) INFORMATION FOR SEQ ID NO:150:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1

( D ) OTHER INFORMATION: /note = "Amino acid is acetylated at
                    the N- terminal."

( i x ) FEATURE:
                ( A ) NAME/KEY: Peptide
                ( B ) LOCATION: 4
                ( D ) OTHER INFORMATION: /note = "Amino acid is amidated at
                    the C- terminal."

( x i ) SEQUENCE DESCRIPTION: SEQ ID NO:150:

Tyr    Ile    Arg    Pro
        1

( 2 ) INFORMATION FOR SEQ ID NO:151:

( i ) SEQUENCE CHARACTERISTICS:
                ( A ) LENGTH: 5 amino acids
                ( B ) TYPE: amino acid
                ( D ) TOPOLOGY: circular ( i x ) FEATURE:
                ( A ) NAME/KEY: Peptide
                ( B ) LOCATION: 1
                ( D ) OTHER INFORMATION: /note = "Amino acid is acetylated at
                    the N- terminal."

( i x ) FEATURE:
                ( A ) NAME/KEY: Peptide
                ( B ) LOCATION: 5
                ( D ) OTHER INFORMATION: /note = "Amino acid is amidated at
                    the C- terminal."

( x i ) SEQUENCE DESCRIPTION: SEQ ID NO:151:

Tyr    Lys    Arg    Leu    Glu
        1                                   5

( 2 ) INFORMATION FOR SEQ ID NO:152:

( i ) SEQUENCE CHARACTERISTICS:
                ( A ) LENGTH: 4 amino acids
                ( B ) TYPE: amino acid
                ( D ) TOPOLOGY: circular ( i x ) FEATURE:
                ( A ) NAME/KEY: Peptide
                ( B ) LOCATION: 1
                ( D ) OTHER INFORMATION: /note = "Amino acid is acetylated at
                    the N- terminal."

( i x ) FEATURE:
                ( A ) NAME/KEY: Peptide
                ( B ) LOCATION: 4
                ( D ) OTHER INFORMATION: /note = "Amino acid is amidated at
                    the C- terminal."

( x i ) SEQUENCE DESCRIPTION: SEQ ID NO:152:

Tyr    Asn    Arg    Leu
        1

( 2 ) INFORMATION FOR SEQ ID NO:153:

( i ) SEQUENCE CHARACTERISTICS:
                ( A ) LENGTH: 5 amino acids
                ( B ) TYPE: amino acid
                ( D ) TOPOLOGY: linear ( i x ) FEATURE:
                ( A ) NAME/KEY: Peptide
                ( B ) LOCATION: 1
                ( D ) OTHER INFORMATION: /note = "Amino acid is acetylated at
                    the N- terminal."

( i x ) FEATURE:
                ( A ) NAME/KEY: Peptide (B) LOCATION: 5
(D) OTHER INFORMATION: /note = "Amino acid is amidated at the C- terminal."

(xi) SEQUENCE DESCRIPTION: SEQ ID NO:153:

Tyr Asn Arg Leu Pro
1               5

(2) INFORMATION FOR SEQ ID NO:154:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is acetylated at the N- terminal."

(ix) FEATURE:
(A) NAME/KEY: Peptide
(B) LOCATION: 2
(D) OTHER INFORMATION: /note = "Thr has a methyl group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:154:

Tyr Thr Arg Leu Pro
1               5

(2) INFORMATION FOR SEQ ID NO:155:

(i) SEQUENCE CHARACTERISTICS:
(A) LENGTH: 5 amino acids
(B) TYPE: amino acid
(D) TOPOLOGY: circular (ix) FEATURE:
(A) NAME/KEY: Peptide
(B) LOCATION: 1
(D) OTHER INFORMATION: /note = "Xaa is Beta-Ala."

(xi) SEQUENCE DESCRIPTION: SEQ ID NO:155:

Xaa Tyr Ile Arg Gly
1               5

(2) INFORMATION FOR SEQ ID NO:156:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Xaa is Beta-Ala."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:156:

Xaa Tyr Ile Arg Gly
1               5

( 2 ) INFORMATION FOR SEQ ID NO:157:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid has CClF-2-CO at the N- terminal."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:157:

Tyr  Ile  Arg  Leu  Pro
    1                       5

( 2 ) INFORMATION FOR SEQ ID NO:158:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid has CF-2H-CO at the N- terminal."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:158:

Tyr  Ile  Arg  Leu  Pro
    1                       5

( 2 ) INFORMATION FOR SEQ ID NO:159:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid has CF-3-CF-2CO at the N- terminal."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:159:

Tyr  Ile  Arg  Leu  Pro
    1                       5

( 2 ) INFORMATION FOR SEQ ID NO:160:

( i ) SEQUENCE CHARACTERISTICS:

(A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note = "Amino acid has CH-3-CHCl-CO
                        at the N- terminal."

(ix) FEATURE:
                (A) NAME/KEY: Peptide
                (B) LOCATION: 5
                (D) OTHER INFORMATION: /note = "Amino acid is amidated at
                        the C- terminal."

(xi) SEQUENCE DESCRIPTION: SEQ ID NO:160:

Tyr  Ile  Arg  Leu  Pro
        1                   5

(2) INFORMATION FOR SEQ ID NO:161:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note = "Amino acid has CH-3-O-CO at
                        the N- terminal."

(ix) FEATURE:
                (A) NAME/KEY: Peptide
                (B) LOCATION: 5
                (D) OTHER INFORMATION: /note = "Amino acid is amidated at
                        the C- terminal."

(xi) SEQUENCE DESCRIPTION: SEQ ID NO:161:

Tyr  Ile  Arg  Leu  Pro
        1                   5

(2) INFORMATION FOR SEQ ID NO:162:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note = "Amino acid has CH-3-SO-2 at
                        the N- terminal."

(ix) FEATURE:
                (A) NAME/KEY: Peptide
                (B) LOCATION: 5
                (D) OTHER INFORMATION: /note = "Amino acid is amidated at
                        the C- terminal."

(xi) SEQUENCE DESCRIPTION: SEQ ID NO:162:

Tyr  Ile  Arg  Leu  Pro
        1                   5

(2) INFORMATION FOR SEQ ID NO:163:

(i) SEQUENCE CHARACTERISTICS:
                (A) LENGTH: 5 amino acids
                (B) TYPE: amino acid
                (D) TOPOLOGY: linear (ix) FEATURE:

(A) NAME/KEY: Peptide
(B) LOCATION: 1
(D) OTHER INFORMATION: /note = "Amino acid has
    CH-3CH-2-O- CO at the N-terminal."

(ix) FEATURE:
    (A) NAME/KEY: Peptide
    (B) LOCATION: 5
    (D) OTHER INFORMATION: /note = "Amino acid is amidated at
        the C- terminal."

(xi) SEQUENCE DESCRIPTION: SEQ ID NO:163:

Tyr Ile Arg Leu Pro
1               5

(2) INFORMATION FOR SEQ ID NO:164:

(i) SEQUENCE CHARACTERISTICS:
        (A) LENGTH: 5 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note = "Amino acid has Cl-2CHCO at
            the N- terminal."

(ix) FEATURE:
        (A) NAME/KEY: Peptide
        (B) LOCATION: 5
        (D) OTHER INFORMATION: /note = "Amino acid is amidated at
            the C- terminal."

(xi) SEQUENCE DESCRIPTION: SEQ ID NO:164:

Tyr Ile Arg Leu Pro
1               5

(2) INFORMATION FOR SEQ ID NO:165:

(i) SEQUENCE CHARACTERISTICS:
        (A) LENGTH: 6 amino acids
        (B) TYPE: amino acid
        (D) TOPOLOGY: circular (ix) FEATURE:
        (A) NAME/KEY: Peptide
        (B) LOCATION: 6
        (D) OTHER INFORMATION: /note = "Amino acid is amidated at
            the C- terminal."

(xi) SEQUENCE DESCRIPTION: SEQ ID NO:165:

Cys Tyr Ile Arg Leu Cys
1               5

(2) INFORMATION FOR SEQ ID NO:166:

(i) SEQUENCE CHARACTERISTICS:
        (A) LENGTH: 9 amino acids
        (B) TYPE: amino acid
        (D) TOPOLOGY: linear (ix) FEATURE:
        (A) NAME/KEY: Peptide
        (B) LOCATION: 2
        (D) OTHER INFORMATION: /note = "Xaa is Tic."

(ix) FEATURE:
        (A) NAME/KEY: Peptide
        (B) LOCATION: 9
        (D) OTHER INFORMATION: /note = "Amino acid is amidated at
            the C- terminal."

(xi) SEQUENCE DESCRIPTION: SEQ ID NO:166:

Asp Xaa Ile Arg Leu Ala Ala Phe Thr
1               5

(2) INFORMATION FOR SEQ ID NO:167:

(i) SEQUENCE CHARACTERISTICS:
      (A) LENGTH: 5 amino acids
      (B) TYPE: amino acid
      (D) TOPOLOGY: linear (ix) FEATURE:
      (A) NAME/KEY: Peptide
      (B) LOCATION: 1
      (D) OTHER INFORMATION: /note = "Tyr has an Et(Et) group."

(ix) FEATURE:
      (A) NAME/KEY: Peptide
      (B) LOCATION: 5
      (D) OTHER INFORMATION: /note = "Amino acid is amidated at the C- terminal."

(xi) SEQUENCE DESCRIPTION: SEQ ID NO:167:

Tyr Ile Arg Leu Pro
1               5

(2) INFORMATION FOR SEQ ID NO:168:

(i) SEQUENCE CHARACTERISTICS:
      (A) LENGTH: 5 amino acids
      (B) TYPE: amino acid
      (D) TOPOLOGY: circular (ix) FEATURE:
      (A) NAME/KEY: Peptide
      (B) LOCATION: 5
      (D) OTHER INFORMATION: /note = "Amino acid is amidated at the C- terminal."

(xi) SEQUENCE DESCRIPTION: SEQ ID NO:168:

Glu Tyr Ile Arg Lys
1               5

(2) INFORMATION FOR SEQ ID NO:169:

(i) SEQUENCE CHARACTERISTICS:
      (A) LENGTH: 6 amino acids
      (B) TYPE: amino acid
      (D) TOPOLOGY: circular (ix) FEATURE:
      (A) NAME/KEY: Peptide
      (B) LOCATION: 6
      (D) OTHER INFORMATION: /note = "Amino acid is amidated at the C- terminal."

(xi) SEQUENCE DESCRIPTION: SEQ ID NO:169:

Glu Tyr Ile Arg Leu Lys
1               5

(2) INFORMATION FOR SEQ ID NO:170:

(i) SEQUENCE CHARACTERISTICS:
      (A) LENGTH: 7 amino acids
      (B) TYPE: amino acid
      (D) TOPOLOGY: circular (ix) FEATURE:
      (A) NAME/KEY: Peptide
      (B) LOCATION: 7
      (D) OTHER INFORMATION: /note = "Amino acid is amidated at the C- terminal."

-continued ( x i ) SEQUENCE DESCRIPTION: SEQ ID NO:170:

Glu Tyr Ile Arg Leu Pro Lys
1               5

( 2 ) INFORMATION FOR SEQ ID NO:171:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Phe has a pCl group."

( i x ) FEATURE:
        ( A ) NAME/KEY: Peptide
        ( B ) LOCATION: 5
        ( D ) OTHER INFORMATION: /note = "Xaa is Sar."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:171:

Phe Ile Arg Ile Xaa
1               5

( 2 ) INFORMATION FOR SEQ ID NO:172:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Phe has a pF group."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:172:

Phe Ile Arg Leu Pro
1               5

( 2 ) INFORMATION FOR SEQ ID NO:173:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Phe has a pNH-2 group."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:173:

Phe Ile Arg Leu Ala

```
          1                     5
```

(2) INFORMATION FOR SEQ ID NO:174:

(i) SEQUENCE CHARACTERISTICS:
        (A) LENGTH: 5 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note = "Phe has a pNO-2 group."

(ix) FEATURE:
        (A) NAME/KEY: Peptide
        (B) LOCATION: 5
        (D) OTHER INFORMATION: /note = "Amino acid is amidated at the C- terminal."

(xi) SEQUENCE DESCRIPTION: SEQ ID NO:174:

```
     Phe   Ile   Arg   Leu   Ala
     1                       5
```

(2) INFORMATION FOR SEQ ID NO:175:

(i) SEQUENCE CHARACTERISTICS:
        (A) LENGTH: 4 amino acids
        (B) TYPE: amino acid
        (D) TOPOLOGY: linear (ix) FEATURE:
        (A) NAME/KEY: Peptide
        (B) LOCATION: 4
        (D) OTHER INFORMATION: /note = "Amino acid is amidated at the C- terminal."

(xi) SEQUENCE DESCRIPTION: SEQ ID NO:175:

```
     Phe   Ile   Arg   Leu
     1
```

(2) INFORMATION FOR SEQ ID NO:176:

(i) SEQUENCE CHARACTERISTICS:
        (A) LENGTH: 8 amino acids
        (B) TYPE: amino acid
        (D) TOPOLOGY: linear (ix) FEATURE:
        (A) NAME/KEY: Peptide
        (B) LOCATION: 8
        (D) OTHER INFORMATION: /note = "Amino acid is amidated at the C- terminal."

(xi) SEQUENCE DESCRIPTION: SEQ ID NO:176:

```
     Phe   Ile   Arg   Leu   Pro   His   Tyr   Gly
     1                       5
```

(2) INFORMATION FOR SEQ ID NO:177:

(i) SEQUENCE CHARACTERISTICS:
        (A) LENGTH: 8 amino acids
        (B) TYPE: amino acid
        (D) TOPOLOGY: linear (ix) FEATURE:
        (A) NAME/KEY: Peptide
        (B) LOCATION: 8
        (D) OTHER INFORMATION: /note = "Amino acid is amidated at the C- terminal."

(xi) SEQUENCE DESCRIPTION: SEQ ID NO:177:

```
Phe  Ile  Arg  Leu  Tyr  Val  Trp  Asn
1                   5
```

( 2 ) INFORMATION FOR SEQ ID NO:178:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid has a formyl
            group at the N-terminal."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:178:

```
Tyr  Ile  Arg  Leu  Pro
1                   5
```

( 2 ) INFORMATION FOR SEQ ID NO:179:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note = "Amino acid is amidated at
            the C- terminal."

( x i ) SEQUENCE DESCRIPTION: SEQ ID NO:179:

```
Gly  Gly  Tyr  Ile  Arg  Gly
1                   5
```

( 2 ) INFORMATION FOR SEQ ID NO:180:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:180:

```
Gly  Tyr  Ile  Arg  Asp
1                   5
```

( 2 ) INFORMATION FOR SEQ ID NO:181:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:181:

Gly Tyr Ile Arg Phe
1               5

( 2 ) INFORMATION FOR SEQ ID NO:182:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:182:

Gly Tyr Ile Arg Gly
1               5

( 2 ) INFORMATION FOR SEQ ID NO:183:

( i ) SEQUENCE CHARACTERISTICS:
        ( A ) LENGTH: 5 amino acids
        ( B ) TYPE: amino acid
        ( D ) TOPOLOGY: circular ( x i ) SEQUENCE DESCRIPTION: SEQ ID NO:183:

Gly Tyr Ile Arg Gly
1               5

( 2 ) INFORMATION FOR SEQ ID NO:184:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:184:

Gly Tyr Ile Arg His
1               5

( 2 ) INFORMATION FOR SEQ ID NO:185:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:185:

Gly Tyr Ile Arg Ile
1               5

( 2 ) INFORMATION FOR SEQ ID NO:186:

( i ) SEQUENCE CHARACTERISTICS:
        ( A ) LENGTH: 5 amino acids (B) TYPE: amino acid
(D) TOPOLOGY: linear (ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:186:

Gly Tyr Ile Arg Lys
1               5

(2) INFORMATION FOR SEQ ID NO:187:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:187:

Gly Tyr Ile Arg Leu
1               5

(2) INFORMATION FOR SEQ ID NO:188:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 6
(D) OTHER INFORMATION: /note = "Amino acid is amidated at the C- terminal."

(xi) SEQUENCE DESCRIPTION: SEQ ID NO:188:

Gly Tyr Ile Arg Leu Pro
1               5

(2) INFORMATION FOR SEQ ID NO:189:

(i) SEQUENCE CHARACTERISTICS:
(A) LENGTH: 8 amino acids
(B) TYPE: amino acid
(D) TOPOLOGY: linear (ix) FEATURE:
(A) NAME/KEY: Peptide
(B) LOCATION: 8
(D) OTHER INFORMATION: /note = "Amino acid is amidated at the C- terminal."

(xi) SEQUENCE DESCRIPTION: SEQ ID NO:189:

Gly Tyr Ile Arg Leu Pro Ala Met
1               5

(2) INFORMATION FOR SEQ ID NO:190:

(i) SEQUENCE CHARACTERISTICS:
(A) LENGTH: 8 amino acids
(B) TYPE: amino acid
(D) TOPOLOGY: linear (ix) FEATURE:

(A) NAME/KEY: Peptide
(B) LOCATION: 8
(D) OTHER INFORMATION: /note = "Amino acid is amidated at the C- terminal."

(x i) SEQUENCE DESCRIPTION: SEQ ID NO:190:

Gly Tyr Ile Arg Leu Pro Pro Val
1               5

(2) INFORMATION FOR SEQ ID NO:191:

(i) SEQUENCE CHARACTERISTICS:
(A) LENGTH: 8 amino acids
(B) TYPE: amino acid
(D) TOPOLOGY: linear (ix) FEATURE:
(A) NAME/KEY: Peptide
(B) LOCATION: 8
(D) OTHER INFORMATION: /note = "Amino acid is amidated at the C- terminal."

(x i) SEQUENCE DESCRIPTION: SEQ ID NO:191:

Gly Tyr Ile Arg Leu Pro Gln Thr
1               5

(2) INFORMATION FOR SEQ ID NO:192:

(i) SEQUENCE CHARACTERISTICS:
(A) LENGTH: 8 amino acids
(B) TYPE: amino acid
(D) TOPOLOGY: linear (ix) FEATURE:
(A) NAME/KEY: Peptide
(B) LOCATION: 8
(D) OTHER INFORMATION: /note = "Amino acid is amidated at the C- terminal."

(x i) SEQUENCE DESCRIPTION: SEQ ID NO:192:

Gly Tyr Ile Arg Leu Pro Ser Gln
1               5

(2) INFORMATION FOR SEQ ID NO:193:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 5
(D) OTHER INFORMATION: /note = "Amino acid is amidated at the C- terminal."

(x i) SEQUENCE DESCRIPTION: SEQ ID NO:193:

Gly Tyr Ile Arg Ser
1               5

(2) INFORMATION FOR SEQ ID NO:194:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 5
(D) OTHER INFORMATION: /note = "Amino acid is amidated at the C- terminal."

(x i) SEQUENCE DESCRIPTION: SEQ ID NO:194:

Gly Tyr Ile Arg Thr
1               5

(2) INFORMATION FOR SEQ ID NO:195:

(i) SEQUENCE CHARACTERISTICS:
    (A) LENGTH: 5 amino acids
    (B) TYPE: amino acid
    (D) TOPOLOGY: linear (i x) FEATURE:
    (A) NAME/KEY: Peptide
    (B) LOCATION: 5
    (D) OTHER INFORMATION: /note = "Amino acid is amidated at
        the C- terminal."

(x i) SEQUENCE DESCRIPTION: SEQ ID NO:195:

Gly Tyr Ile Arg Val
1               5

(2) INFORMATION FOR SEQ ID NO:196:

(i) SEQUENCE CHARACTERISTICS:
    (A) LENGTH: 5 amino acids
    (B) TYPE: amino acid
    (D) TOPOLOGY: linear (i x) FEATURE:
    (A) NAME/KEY: Peptide
    (B) LOCATION: 5
    (D) OTHER INFORMATION: /note = "Amino acid is amidated at
        the C- terminal."

(x i) SEQUENCE DESCRIPTION: SEQ ID NO:196:

Gly Tyr Ile Arg Trp
1               5

(2) INFORMATION FOR SEQ ID NO:197:

(i) SEQUENCE CHARACTERISTICS:
    (A) LENGTH: 5 amino acids
    (B) TYPE: amino acid
    (D) TOPOLOGY: linear (i x) FEATURE:
    (A) NAME/KEY: Peptide
    (B) LOCATION: 5
    (D) OTHER INFORMATION: /note = "Amino acid is amidated at
        the C- terminal."

(x i) SEQUENCE DESCRIPTION: SEQ ID NO:197:

Gly Tyr Ile Arg Tyr
1               5

(2) INFORMATION FOR SEQ ID NO:198:

(i) SEQUENCE CHARACTERISTICS:
    (A) LENGTH: 4 amino acids
    (B) TYPE: amino acid
    (D) TOPOLOGY: linear (i x) FEATURE:
    (A) NAME/KEY: Peptide
    (B) LOCATION: 1
    (D) OTHER INFORMATION: /note = "Amino acid has
        (p O H )C-6H-4-CH-2CH-2(OH)-CO at the N-terminal."

(i x) FEATURE:
    (A) NAME/KEY: Peptide
    (B) LOCATION: 4

( D ) OTHER INFORMATION: /note = "Xaa is Sar."

( i x ) FEATURE:
    ( A ) NAME/KEY: Peptide
    ( B ) LOCATION: 4
    ( D ) OTHER INFORMATION: /note = "Amino acid is amidated at the C- terminal."

( x i ) SEQUENCE DESCRIPTION: SEQ ID NO:198:

Ile Arg Leu Xaa
1

( 2 ) INFORMATION FOR SEQ ID NO:199:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid has ( p O H )C-6H-4-CH-2CH-2CO at the N-terminal."

( i x ) FEATURE:
    ( A ) NAME/KEY: Peptide
    ( B ) LOCATION: 4
    ( D ) OTHER INFORMATION: /note = "Amino acid is amidated at the C- terminal."

( x i ) SEQUENCE DESCRIPTION: SEQ ID NO:199:

Ile Arg Leu Ala
1

( 2 ) INFORMATION FOR SEQ ID NO:200:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid has ( p O H )C-6H-4-CH-2CH-2CO at the N-terminal."

( i x ) FEATURE:
    ( A ) NAME/KEY: Peptide
    ( B ) LOCATION: 4
    ( D ) OTHER INFORMATION: /note = "Amino acid is amidated at the C- terminal."

( x i ) SEQUENCE DESCRIPTION: SEQ ID NO:200:

Ile Arg Leu Pro
1

( 2 ) INFORMATION FOR SEQ ID NO:201:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid has ( p O H )C-6H-4-CH-2CHOH-CO at the N-terminal."

( i x ) FEATURE:
    ( A ) NAME/KEY: Peptide
    ( B ) LOCATION: 4

(D) OTHER INFORMATION: /note = "Amino acid is amidated at
the C- terminal."

(xi) SEQUENCE DESCRIPTION: SEQ ID NO:201:

Ile Arg Leu Pro
1

(2) INFORMATION FOR SEQ ID NO:202:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid has
(pOH)C-6H-4-OCH(CH-3)CO at the N-terminal."

(ix) FEATURE:
(A) NAME/KEY: Peptide
(B) LOCATION: 4
(D) OTHER INFORMATION: /note = "Amino acid is amidated at
the C- terminal."

(xi) SEQUENCE DESCRIPTION: SEQ ID NO:202:

Ile Arg Leu Pro
1

(2) INFORMATION FOR SEQ ID NO:203:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid has
(pOH)C-6H-4-OCH-2CO at the N-terminal."

(ix) FEATURE:
(A) NAME/KEY: Peptide
(B) LOCATION: 4
(D) OTHER INFORMATION: /note = "Amino acid is amidated at
the C- terminal."

(xi) SEQUENCE DESCRIPTION: SEQ ID NO:203:

Ile Arg Leu Pro
1

(2) INFORMATION FOR SEQ ID NO:204:

(i) SEQUENCE CHARACTERISTICS:
(A) LENGTH: 9 amino acids
(B) TYPE: amino acid
(D) TOPOLOGY: linear (ix) FEATURE:
(A) NAME/KEY: Peptide
(B) LOCATION: 9
(D) OTHER INFORMATION: /note = "Amino acid is amidated at
the C- terminal."

(xi) SEQUENCE DESCRIPTION: SEQ ID NO:204:

Ile His Leu Trp Tyr Ile Arg Leu Pro
1               5

(2) INFORMATION FOR SEQ ID NO:205:

( i ) SEQUENCE CHARACTERISTICS:
    ( A ) LENGTH: 9 amino acids
    ( B ) TYPE: amino acid
    ( D ) TOPOLOGY: linear ( i x ) FEATURE:
    ( A ) NAME/KEY: Peptide
    ( B ) LOCATION: 9
    ( D ) OTHER INFORMATION: /note = "Amino acid is amidated at the C- terminal."

( x i ) SEQUENCE DESCRIPTION: SEQ ID NO:205:

Ile Gln Leu Gly Tyr Ile Arg Leu Pro
1               5

( 2 ) INFORMATION FOR SEQ ID NO:206:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid has 4-MeO-C-6H-4- CO at the N-terminal."

( i x ) FEATURE:
    ( A ) NAME/KEY: Peptide
    ( B ) LOCATION: 4
    ( D ) OTHER INFORMATION: /note = "Amino acid is amidated at the C- terminal."

( x i ) SEQUENCE DESCRIPTION: SEQ ID NO:206:

Ile Arg Leu Ala
1

( 2 ) INFORMATION FOR SEQ ID NO:207:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid has N- morpholinyl-CO at the N-terminal."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:207:

Phe Ile Arg Leu Pro
1               5

( 2 ) INFORMATION FOR SEQ ID NO:208:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Xaa is Nal(2)."

( i x ) FEATURE:

(A) NAME/KEY: Peptide
                (B) LOCATION: 2
                (D) OTHER INFORMATION: /note = "Xaa is Cha."

(ix) FEATURE:
                (A) NAME/KEY: Peptide
                (B) LOCATION: 4
                (D) OTHER INFORMATION: /note = "Asp has an O-Allyl group."

(ix) FEATURE:
                (A) NAME/KEY: Peptide
                (B) LOCATION: 4
                (D) OTHER INFORMATION: /note = "Amino acid is amidated at
                        the C- terminal."

(xi) SEQUENCE DESCRIPTION: SEQ ID NO:208:

Xaa  Xaa  Arg  Asp
        1

(2) INFORMATION FOR SEQ ID NO:209:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note = "Xaa is Nal(2)."

(ix) FEATURE:
                (A) NAME/KEY: Peptide
                (B) LOCATION: 2
                (D) OTHER INFORMATION: /note = "Xaa is Cha."

(ix) FEATURE:
                (A) NAME/KEY: Peptide
                (B) LOCATION: 4
                (D) OTHER INFORMATION: /note = "Asp has an O-Allyl group."

(ix) FEATURE:
                (A) NAME/KEY: Peptide
                (B) LOCATION: 5
                (D) OTHER INFORMATION: /note = "Xaa is Sar."

(ix) FEATURE:
                (A) NAME/KEY: Peptide
                (B) LOCATION: 5
                (D) OTHER INFORMATION: /note = "Amino acid is amidated at
                        the C- terminal."

(xi) SEQUENCE DESCRIPTION: SEQ ID NO:209:

Xaa  Xaa  Arg  Asp  Xaa
        1                    5

(2) INFORMATION FOR SEQ ID NO:210:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note = "Xaa is Nal(2)."

(ix) FEATURE:
                (A) NAME/KEY: Peptide
                (B) LOCATION: 2
                (D) OTHER INFORMATION: /note = "Xaa is Chg."

(ix) FEATURE:
                (A) NAME/KEY: Peptide
                (B) LOCATION: 5

(D) OTHER INFORMATION: /note = "Amino acid is amidated at
            the C- terminal."

(x i) SEQUENCE DESCRIPTION: SEQ ID NO:210:

Xaa    Xaa    Arg    Leu    Pro
1                                  5

(2) INFORMATION FOR SEQ ID NO:211:

(i) SEQUENCE CHARACTERISTICS:
        (A) LENGTH: 5 amino acids
        (B) TYPE: amino acid
        (D) TOPOLOGY: linear (i x) FEATURE:
        (A) NAME/KEY: Peptide
        (B) LOCATION: 1
        (D) OTHER INFORMATION: /note = "Xaa is Nal(2)."

(i x) FEATURE:
        (A) NAME/KEY: Peptide
        (B) LOCATION: 4
        (D) OTHER INFORMATION: /note = "Cys has an Me group."

(i x) FEATURE:
        (A) NAME/KEY: Peptide
        (B) LOCATION: 5
        (D) OTHER INFORMATION: /note = "Amino acid is amidated at
            the C- terminal."

(x i) SEQUENCE DESCRIPTION: SEQ ID NO:211:

Xaa    Ile    Arg    Cys    Pro
1                                  5

(2) INFORMATION FOR SEQ ID NO:212:

(i) SEQUENCE CHARACTERISTICS:
        (A) LENGTH: 8 amino acids
        (B) TYPE: amino acid
        (D) TOPOLOGY: linear (i x) FEATURE:
        (A) NAME/KEY: Peptide
        (B) LOCATION: 8
        (D) OTHER INFORMATION: /note = "Amino acid is amidated at
            the C- terminal."

(x i) SEQUENCE DESCRIPTION: SEQ ID NO:212:

Asn    Gly    Tyr    Ile    Arg    Leu    Ile    His
1                                  5

(2) INFORMATION FOR SEQ ID NO:213:

(i) SEQUENCE CHARACTERISTICS:
        (A) LENGTH: 4 amino acids
        (B) TYPE: amino acid
        (D) TOPOLOGY: linear (i x) FEATURE:
        (A) NAME/KEY: Peptide
        (B) LOCATION: 1
        (D) OTHER INFORMATION: /note = "Xaa is Pgl(OH)."

(i x) FEATURE:
        (A) NAME/KEY: Peptide
        (B) LOCATION: 4
        (D) OTHER INFORMATION: /note = "Amino acid is amidated at
            the C- terminal."

(x i) SEQUENCE DESCRIPTION: SEQ ID NO:213:

Xaa    Ile    Arg    Leu
1

( 2 ) INFORMATION FOR SEQ ID NO:214:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid has Ph-CH=CH-CO
            at the N- terminal."

( i x ) FEATURE:
        ( A ) NAME/KEY: Peptide
        ( B ) LOCATION: 4
        ( D ) OTHER INFORMATION: /note = "Amino acid is amidated at
            the C- terminal."

( x i ) SEQUENCE DESCRIPTION: SEQ ID NO:214:

Ile Arg Leu Ala
    1

( 2 ) INFORMATION FOR SEQ ID NO:215:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid has
            Ph-CH-2CH- 2CH-2-CO at the N-terminal."

( i x ) FEATURE:
        ( A ) NAME/KEY: Peptide
        ( B ) LOCATION: 4
        ( D ) OTHER INFORMATION: /note = "Amino acid is amidated at
            the C- terminal."

( x i ) SEQUENCE DESCRIPTION: SEQ ID NO:215:

Ile Arg Leu Ala
    1

( 2 ) INFORMATION FOR SEQ ID NO:216:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid has
            Ph-CH-2CH- 2CO at the N-terminal."

( i x ) FEATURE:
        ( A ) NAME/KEY: Peptide
        ( B ) LOCATION: 4
        ( D ) OTHER INFORMATION: /note = "Amino acid is amidated at
            the C- terminal."

( x i ) SEQUENCE DESCRIPTION: SEQ ID NO:216:

Ile Arg Leu Ala
    1

( 2 ) INFORMATION FOR SEQ ID NO:217:

( i ) SEQUENCE CHARACTERISTICS:
        ( A ) LENGTH: 6 amino acids (B) TYPE: amino acid
(D) TOPOLOGY: linear (ix) FEATURE:
(A) NAME/KEY: Peptide
(B) LOCATION: 1
(D) OTHER INFORMATION: /note = "Xaa is Pth."

(ix) FEATURE:
(A) NAME/KEY: Peptide
(B) LOCATION: 6
(D) OTHER INFORMATION: /note = "Amino acid is amidated at the C- terminal."

(xi) SEQUENCE DESCRIPTION: SEQ ID NO:217:

Xaa Tyr Ile Arg Leu Pro
1               5

(2) INFORMATION FOR SEQ ID NO:218:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 6
(D) OTHER INFORMATION: /note = "Amino acid is amidated at the C- terminal."

(xi) SEQUENCE DESCRIPTION: SEQ ID NO:218:

Ser Tyr Ile Arg Leu Pro
1               5

(2) INFORMATION FOR SEQ ID NO:219:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is trifluoroacetylated at the N-terminal."

(ix) FEATURE:
(A) NAME/KEY: Peptide
(B) LOCATION: 1
(D) OTHER INFORMATION: /note = "Phe has an iso-butyl and a pNH-2 group."

(ix) FEATURE:
(A) NAME/KEY: Peptide
(B) LOCATION: 2
(D) OTHER INFORMATION: /note = "Xaa is Chg."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:219:

Phe Xaa Arg Leu Pro
1           5

(2) INFORMATION FOR SEQ ID NO:220:

(i) SEQUENCE CHARACTERISTICS:
(A) LENGTH: 5 amino acids
(B) TYPE: amino acid ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is
        trifluoroacetylated at the N-terminal."

( i x ) FEATURE:
    ( A ) NAME/KEY: Peptide
    ( B ) LOCATION: 1
    ( D ) OTHER INFORMATION: /note = "Xaa is (iBu)Nal(2)."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5
    ( D ) OTHER INFORMATION: /note = "Amino acid is amidated at
        the C- terminal."

( x i ) SEQUENCE DESCRIPTION: SEQ ID NO:220:

Xaa Xaa Arg Leu Pro
1               5

( 2 ) INFORMATION FOR SEQ ID NO:221:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is
            trifluoroacetylated at the N-terminal."

( i x ) FEATURE:
        ( A ) NAME/KEY: Peptide
        ( B ) LOCATION: 1
        ( D ) OTHER INFORMATION: /note = "Tyr has an iBu group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:221:

Tyr Xaa Arg Leu Pro
1               5

( 2 ) INFORMATION FOR SEQ ID NO:222:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is
            trifluoroacetylated at the N-terminal."

( i x ) FEATURE:
        ( A ) NAME/KEY: Peptide ( B ) LOCATION: 1
( D ) OTHER INFORMATION: /note = "Tyr has an iBu group."

( i x ) FEATURE:
( A ) NAME/KEY: Peptide
( B ) LOCATION: 3
( D ) OTHER INFORMATION: /note = "Xaa is Dab-derived
dimethylamidinium."

( i x ) FEATURE:
( A ) NAME/KEY: Peptide
( B ) LOCATION: 5
( D ) OTHER INFORMATION: /note = "Amino acid is amidated at
the C- terminal."

( x i ) SEQUENCE DESCRIPTION: SEQ ID NO:222:

Tyr Ile Xaa Leu Pro
1               5

( 2 ) INFORMATION FOR SEQ ID NO:223:

( i ) SEQUENCE CHARACTERISTICS:
( A ) LENGTH: 5 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note = "Amino acid is
trifluoroacetylated at the N-terminal."

( i x ) FEATURE:
( A ) NAME/KEY: Peptide
( B ) LOCATION: 1
( D ) OTHER INFORMATION: /note = "Tyr has an iBu group."

( i x ) FEATURE:
( A ) NAME/KEY: Peptide
( B ) LOCATION: 3
( D ) OTHER INFORMATION: /note = "Xaa is Ornithine-derived
dimethylamidinium."

( i x ) FEATURE:
( A ) NAME/KEY: Peptide
( B ) LOCATION: 5
( D ) OTHER INFORMATION: /note = "Amino acid is amidated at
the C- terminal."

( x i ) SEQUENCE DESCRIPTION: SEQ ID NO:223:

Tyr Ile Xaa Leu Pro
1               5

( 2 ) INFORMATION FOR SEQ ID NO:224:

( i ) SEQUENCE CHARACTERISTICS:
( A ) LENGTH: 4 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note = "Amino acid is
trifluoroacetylated at the N-terminal."

( i x ) FEATURE:
( A ) NAME/KEY: Peptide
( B ) LOCATION: 1
( D ) OTHER INFORMATION: /note = "Tyr has an iBu group."

( i x ) FEATURE:
( A ) NAME/KEY: Peptide
( B ) LOCATION: 4
( D ) OTHER INFORMATION: /note = "Amino acid is amidated at
the C- terminal."

( x i ) SEQUENCE DESCRIPTION: SEQ ID NO:224:

Tyr Ile Arg Gly
1

( 2 ) INFORMATION FOR SEQ ID NO:225:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is trifluoroacetylated at the N-terminal."

( i x ) FEATURE:
        ( A ) NAME/KEY: Peptide
        ( B ) LOCATION: 1
        ( D ) OTHER INFORMATION: /note = "Tyr has an iBu group."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:225:

Tyr Ile Arg Leu Pro
1                 5

( 2 ) INFORMATION FOR SEQ ID NO:226:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is trifluoroacetylated at the N-terminal."

( i x ) FEATURE:
        ( A ) NAME/KEY: Peptide
        ( B ) LOCATION: 1
        ( D ) OTHER INFORMATION: /note = "Tyr has an methyl group."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:226:

Tyr Ile Arg Leu Ala
1                 5

( 2 ) INFORMATION FOR SEQ ID NO:227:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is trifluoroacetylated at the N-terminal."

( i x ) FEATURE:
    ( A ) NAME/KEY: Peptide
    ( B ) LOCATION: 1
    ( D ) OTHER INFORMATION: /note = "Tyr has an methyl group."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:227:

Tyr Ile Arg Leu Pro
1                 5

( 2 ) INFORMATION FOR SEQ ID NO:228:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is trifluoroacetylated at the N-terminal."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:228:

Tyr Xaa Arg Leu Pro
1                 5

( 2 ) INFORMATION FOR SEQ ID NO:229:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is trifluoroacetylated at the N-terminal."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:229:

Tyr Ile Arg Leu Pro
1                 5

( 2 ) INFORMATION FOR SEQ ID NO:230:

( i ) SEQUENCE CHARACTERISTICS:
    ( A ) LENGTH: 8 amino acids
    ( B ) TYPE: amino acid
    ( D ) TOPOLOGY: linear ( i x ) FEATURE:

(A) NAME/KEY: Peptide
(B) LOCATION: 8
(D) OTHER INFORMATION: /note = "Amino acid is amidated at the C- terminal."

(xi) SEQUENCE DESCRIPTION: SEQ ID NO:230:

Thr Phe Gly Tyr Ile Arg Lys Ala
1               5

(2) INFORMATION FOR SEQ ID NO:231:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid has a tosyl group at the N-terminal."

(ix) FEATURE:
(A) NAME/KEY: Peptide
(B) LOCATION: 5
(D) OTHER INFORMATION: /note = "Xaa is Sar."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:231:

Gly Ile Arg Val Xaa
1               5

(2) INFORMATION FOR SEQ ID NO:232:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Tyr has a methyl group."

(ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:232:

Tyr Ile Arg Leu Ala
1               5

(2) INFORMATION FOR SEQ ID NO:233:

(i) SEQUENCE CHARACTERISTICS:
(A) LENGTH: 10 amino acids
(B) TYPE: amino acid
(D) TOPOLOGY: linear (ix) FEATURE:
(A) NAME/KEY: Peptide
(B) LOCATION: 10
(D) OTHER INFORMATION: /note = "Amino acid is amidated at the C- terminal."

(xi) SEQUENCE DESCRIPTION: SEQ ID NO:233:

```
Trp  Phe  Arg  Glu  Met  Gly  Gly  Gly  Gly  Gly
1              5                        10
```

( 2 ) INFORMATION FOR SEQ ID NO:234:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:234:

```
Trp  Ile  Arg  Glu  Lys
1              5
```

( 2 ) INFORMATION FOR SEQ ID NO:235:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:235:

```
Trp  Ile  Arg  Asn  Pro
1              5
```

( 2 ) INFORMATION FOR SEQ ID NO:236:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:236:

```
Trp  Ile  Arg  Thr  Pro
1              5
```

( 2 ) INFORMATION FOR SEQ ID NO:237:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:237:

```
Trp  Leu  Arg  Leu  Ala
1              5
```

( 2 ) INFORMATION FOR SEQ ID NO:238:

( i ) SEQUENCE CHARACTERISTICS:
        ( A ) LENGTH: 10 amino acids
        ( B ) TYPE: amino acid
        ( D ) TOPOLOGY: linear ( i x ) FEATURE:
        ( A ) NAME/KEY: Peptide
        ( B ) LOCATION: 10
        ( D ) OTHER INFORMATION: /note = "Amino acid is amidated at
            the C- terminal."

( x i ) SEQUENCE DESCRIPTION: SEQ ID NO:238:

```
Trp Leu Arg Leu Ala Gly Gly Gly Gly Gly
1               5                   10
```

( 2 ) INFORMATION FOR SEQ ID NO:239:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:239:

```
Trp Leu Arg Val Ala
1               5
```

( 2 ) INFORMATION FOR SEQ ID NO:240:

( i ) SEQUENCE CHARACTERISTICS:
        ( A ) LENGTH: 10 amino acids
        ( B ) TYPE: amino acid
        ( D ) TOPOLOGY: linear ( i x ) FEATURE:
        ( A ) NAME/KEY: Peptide
        ( B ) LOCATION: 10
        ( D ) OTHER INFORMATION: /note = "Amino acid is amidated at
            the C- terminal."

( x i ) SEQUENCE DESCRIPTION: SEQ ID NO:240:

```
Trp Leu Arg Val Ala Gly Gly Gly Gly Gly
1               5                   10
```

( 2 ) INFORMATION FOR SEQ ID NO:241:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 8
        ( D ) OTHER INFORMATION: /note = "Amino acid is amidated at
            the C- terminal."

( x i ) SEQUENCE DESCRIPTION: SEQ ID NO:241:

```
Tyr Ile Arg Glu Phe Ser Asp Tyr
1               5
```

( 2 ) INFORMATION FOR SEQ ID NO:242:

( i ) SEQUENCE CHARACTERISTICS:
        ( A ) LENGTH: 5 amino acids

-continued ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:242:

Tyr Ile Arg Gly Ala
1                 5

( 2 ) INFORMATION FOR SEQ ID NO:243:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 4
        ( D ) OTHER INFORMATION: /note = "Amino acid is amidated at
            the C- terminal."

( x i ) SEQUENCE DESCRIPTION: SEQ ID NO:243:

Tyr Ile Arg Ile
1

( 2 ) INFORMATION FOR SEQ ID NO:244:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:244:

Tyr Ile Arg Ile Tyr
1                 5

( 2 ) INFORMATION FOR SEQ ID NO:245:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 8
        ( D ) OTHER INFORMATION: /note = "Amino acid is amidated at
            the C- terminal."

( x i ) SEQUENCE DESCRIPTION: SEQ ID NO:245:

Tyr Ile Arg Ile Tyr Glu Arg Glu
1                 5

( 2 ) INFORMATION FOR SEQ ID NO:246:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:

(A) NAME/KEY: Peptide
(B) LOCATION: 4
(D) OTHER INFORMATION: /note = "Amino acid is amidated at the C- terminal."

(xi) SEQUENCE DESCRIPTION: SEQ ID NO:246:

Tyr Ile Arg Leu
1

(2) INFORMATION FOR SEQ ID NO:247:

(i) SEQUENCE CHARACTERISTICS:
(A) LENGTH: 5 amino acids
(B) TYPE: amino acid
(D) TOPOLOGY: linear (ix) FEATURE:
(A) NAME/KEY: Peptide
(B) LOCATION: 5
(D) OTHER INFORMATION: /note = "Amino acid is amidated at the C- terminal."

(xi) SEQUENCE DESCRIPTION: SEQ ID NO:247:

Tyr Ile Arg Leu Ala
1               5

(2) INFORMATION FOR SEQ ID NO:248:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 1
(D) OTHER INFORMATION: /note = "Amino acid is amidated at the C- terminal."

(xi) SEQUENCE DESCRIPTION: SEQ ID NO:248:

Tyr Ile Arg Leu Ala Ala
1               5

(2) INFORMATION FOR SEQ ID NO:249:

(i) SEQUENCE CHARACTERISTICS:
(A) LENGTH: 7 amino acids
(B) TYPE: amino acid
(D) TOPOLOGY: linear (ix) FEATURE:
(A) NAME/KEY: Peptide
(B) LOCATION: 7
(D) OTHER INFORMATION: /note = "Amino acid is amidated at the C- terminal."

(xi) SEQUENCE DESCRIPTION: SEQ ID NO:249:

Tyr Ile Arg Leu Ala Ala Phe
1               5

(2) INFORMATION FOR SEQ ID NO:250:

(i) SEQUENCE CHARACTERISTICS:
(A) LENGTH: 8 amino acids
(B) TYPE: amino acid
(D) TOPOLOGY: linear (ix) FEATURE:
(A) NAME/KEY: Peptide
(B) LOCATION: 8
(D) OTHER INFORMATION: /note = "Amino acid is amidated at the C- terminal."

( x i ) SEQUENCE DESCRIPTION: SEQ ID NO:250:

Tyr Ile Arg Leu Ala Ala Phe Thr
1               5

( 2 ) INFORMATION FOR SEQ ID NO:251:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 8
        ( D ) OTHER INFORMATION: /note = "Amino acid is amidated at the C- terminal."

( x i ) SEQUENCE DESCRIPTION: SEQ ID NO:251:

Tyr Ile Arg Leu Met Glu Met Thr
1               5

( 2 ) INFORMATION FOR SEQ ID NO:252:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:252:

Tyr Ile Arg Leu Pro
1               5

( 2 ) INFORMATION FOR SEQ ID NO:253:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 8
        ( D ) OTHER INFORMATION: /note = "Amino acid is amidated at the C- terminal."

( x i ) SEQUENCE DESCRIPTION: SEQ ID NO:253:

Tyr Ile Arg Leu Pro Gly Leu Leu
1               5

( 2 ) INFORMATION FOR SEQ ID NO:254:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 8
        ( D ) OTHER INFORMATION: /note = "Amino acid is amidated at the C- terminal."

( x i ) SEQUENCE DESCRIPTION: SEQ ID NO:254:

Tyr Ile Arg Leu Thr Lys Met Trp

-continued

```
        1               5
```

( 2 ) INFORMATION FOR SEQ ID NO:255:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 8
        ( D ) OTHER INFORMATION: /note = "Amino acid is amidated at the C- terminal."

( x i ) SEQUENCE DESCRIPTION: SEQ ID NO:255:

```
    Tyr  Ile  Arg  Val  Ala  Gln  Leu  Tyr
    1                   5
```

( 2 ) INFORMATION FOR SEQ ID NO:256:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 8
        ( D ) OTHER INFORMATION: /note = "Amino acid is amidated at the C- terminal."

( x i ) SEQUENCE DESCRIPTION: SEQ ID NO:256:

```
    Tyr  Ile  Arg  Val  Met  Asn  His  Arg
    1                   5
```

( 2 ) INFORMATION FOR SEQ ID NO:257:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 8
        ( D ) OTHER INFORMATION: /note = "Amino acid is amidated at the C- terminal."

( x i ) SEQUENCE DESCRIPTION: SEQ ID NO:257:

```
    Tyr  Ile  Arg  Tyr  Arg  Asn  Pro  Ile
    1                   5
```

( 2 ) INFORMATION FOR SEQ ID NO:258:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide
        ( B ) LOCATION: 8
        ( D ) OTHER INFORMATION: /note = "Amino acid is amidated at the C- terminal."

( x i ) SEQUENCE DESCRIPTION: SEQ ID NO:258:

```
    Tyr  Arg  Tyr  Pro  Arg  Asp  Arg  Asn
    1                   5
```

( 2 ) INFORMATION FOR SEQ ID NO:259:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:259:

Tyr Leu Arg Phe Pro
1               5

( 2 ) INFORMATION FOR SEQ ID NO:260:

( i ) SEQUENCE CHARACTERISTICS:
    ( A ) LENGTH: 8 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( x i ) SEQUENCE DESCRIPTION: SEQ ID NO:260:

Tyr Ile Arg Leu Ala Ala Phe Thr
1               5

( 2 ) INFORMATION FOR SEQ ID NO:261:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( x i ) SEQUENCE DESCRIPTION: SEQ ID NO:261:

Tyr Ile Arg Leu Pro
1               5

( 2 ) INFORMATION FOR SEQ ID NO:262:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Tyr has an iBu group."

( x i ) SEQUENCE DESCRIPTION: SEQ ID NO:262:

Tyr Ile Arg Leu Pro
1               5

( 2 ) INFORMATION FOR SEQ ID NO:263:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is acetylated at the N- terminal."

( i x ) FEATURE:
        ( A ) NAME/KEY: Peptide
        ( B ) LOCATION: 1
        ( D ) OTHER INFORMATION: /note = "Phe has a pNH-2 group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 3
        ( D ) OTHER INFORMATION: /note = "Leu has a Dab-derived dimethylamidinium group."

( i x ) FEATURE:
        ( A ) NAME/KEY: Peptide
        ( B ) LOCATION: 4
        ( D ) OTHER INFORMATION: /note = "Amino acid is amidated at the C- terminal."

( x i ) SEQUENCE DESCRIPTION: SEQ ID NO:263:

Phe Xaa Leu Pro
    1

( 2 ) INFORMATION FOR SEQ ID NO:264:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid has a benzoyl at the N- terminal."

( i x ) FEATURE:
        ( A ) NAME/KEY: Peptide
        ( B ) LOCATION: 1
        ( D ) OTHER INFORMATION: /note = "Phe has a pNH-2 group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at the C- terminal."

( x i ) SEQUENCE DESCRIPTION: SEQ ID NO:264:

Phe Xaa Arg Leu Pro
    1                 5

( 2 ) INFORMATION FOR SEQ ID NO:265:

( i ) SEQUENCE CHARACTERISTICS:
        ( A ) LENGTH: 5 amino acids (B) TYPE: amino acid
                (D) TOPOLOGY: linear (ix) FEATURE:
                (A) NAME/KEY: Peptide
                (B) LOCATION: 1
                (D) OTHER INFORMATION: /note = "Amino acid has a tosyl
                        group at the N-terminal."

(ix) FEATURE:
                (A) NAME/KEY: Peptide
                (B) LOCATION: 1
                (D) OTHER INFORMATION: /note = "Phe has a pNH-2 group."

(ix) FEATURE:
                (A) NAME/KEY: Peptide
                (B) LOCATION: 2
                (D) OTHER INFORMATION: /note = "Xaa is Chg."

(ix) FEATURE:
                (A) NAME/KEY: Peptide
                (B) LOCATION: 5
                (D) OTHER INFORMATION: /note = "Amino acid is amidated at
                        the C- terminal."

(xi) SEQUENCE DESCRIPTION: SEQ ID NO:265:

Phe  Xaa  Arg  Leu  Pro
        1                   5

(2) INFORMATION FOR SEQ ID NO:266:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note = "Amino acid is acetylated at
                        the N- terminal."

(ix) FEATURE:
                (A) NAME/KEY: Peptide
                (B) LOCATION: 1
                (D) OTHER INFORMATION: /note = "Tyr has 3-I group."

(ix) FEATURE:
                (A) NAME/KEY: Peptide
                (B) LOCATION: 2
                (D) OTHER INFORMATION: /note = "Xaa is Chg."

(ix) FEATURE:
                (A) NAME/KEY: Peptide
                (B) LOCATION: 5
                (D) OTHER INFORMATION: /note = "Amino acid is amidated at
                        the C- terminal."

(xi) SEQUENCE DESCRIPTION: SEQ ID NO:266:

Tyr  Xaa  Arg  Leu  Pro
        1                   5

(2) INFORMATION FOR SEQ ID NO:267:

(i) SEQUENCE CHARACTERISTICS:
                (A) LENGTH: 6 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /note = "Xaa is 3-Iqc."

(ix) FEATURE:
                (A) NAME/KEY: Peptide ( B ) LOCATION: 1
( D ) OTHER INFORMATION: /note = "Phe has a pNH-2 group."

( i x ) FEATURE:
( A ) NAME/KEY: Peptide
( B ) LOCATION: 2
( D ) OTHER INFORMATION: /note = "Xaa is Chg."

( i x ) FEATURE:
( A ) NAME/KEY: Peptide
( B ) LOCATION: 5
( D ) OTHER INFORMATION: /note = "Amino acid is amidated at the C- terminal."

( x i ) SEQUENCE DESCRIPTION: SEQ ID NO:267:

Xaa  Phe  Xaa  Arg  Leu  Pro
1                    5

( 2 ) INFORMATION FOR SEQ ID NO:268:

( i ) SEQUENCE CHARACTERISTICS:
( A ) LENGTH: 5 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note = "Amino acid is acetylated at the N- terminal."

( i x ) FEATURE:
( A ) NAME/KEY: Peptide
( B ) LOCATION: 1
( D ) OTHER INFORMATION: /note = "Phe has a p-amidino group."

( i x ) FEATURE:
( A ) NAME/KEY: Peptide
( B ) LOCATION: 2
( D ) OTHER INFORMATION: /note = "Xaa is Chg."

( i x ) FEATURE:
( A ) NAME/KEY: Peptide
( B ) LOCATION: 3
( D ) OTHER INFORMATION: /note = "Xaa is Dab-derived dimethylamidinium."

( i x ) FEATURE:
( A ) NAME/KEY: Peptide
( B ) LOCATION: 5
( D ) OTHER INFORMATION: /note = "Amino acid is amidated at the C- terminal."

( x i ) SEQUENCE DESCRIPTION: SEQ ID NO:268:

Phe  Xaa  Xaa  Leu  Pro
1                5

( 2 ) INFORMATION FOR SEQ ID NO:269:

( i ) SEQUENCE CHARACTERISTICS:
( A ) LENGTH: 6 amino acids
( B ) TYPE: amino acid
( D ) TOPOLOGY: circular ( i x ) FEATURE:
( A ) NAME/KEY: Peptide
( B ) LOCATION: 1
( D ) OTHER INFORMATION: /note = "Amino acid is acetylated at the N- terminal."

( i x ) FEATURE:
( A ) NAME/KEY: Peptide
( B ) LOCATION: 1
( D ) OTHER INFORMATION: /note = "Xaa is Orn."

( i x ) FEATURE:

(A) NAME/KEY: Peptide
                    (B) LOCATION: 2
                    (D) OTHER INFORMATION: /note = "Xaa is Nal(2)."

(ix) FEATURE:
                    (A) NAME/KEY: Peptide
                    (B) LOCATION: 3
                    (D) OTHER INFORMATION: /note = "Xaa is Chg."

(ix) FEATURE:
                    (A) NAME/KEY: Peptide
                    (B) LOCATION: 4
                    (D) OTHER INFORMATION: /note = "Xaa is PalMe(3)."

(ix) FEATURE:
                    (A) NAME/KEY: Peptide
                    (B) LOCATION: 5
                    (D) OTHER INFORMATION: /note = "Xaa is Sar."

(ix) FEATURE:
                    (A) NAME/KEY: Peptide
                    (B) LOCATION: 6
                    (D) OTHER INFORMATION: /note = "Amino acid is amidated at
                        the C- terminal."

(xi) SEQUENCE DESCRIPTION: SEQ ID NO:269:

Xaa  Xaa  Xaa  Xaa  Xaa  Glu
    1                   5

(2) INFORMATION FOR SEQ ID NO:270:

(i) SEQUENCE CHARACTERISTICS:
                    (A) LENGTH: 5 amino acids
                    (B) TYPE: amino acid
                    (D) TOPOLOGY: linear (ix) FEATURE:
                    (A) NAME/KEY: Peptide
                    (B) LOCATION: 1
                    (D) OTHER INFORMATION: /note = "Amino acid is acetylated at
                        the N- terminal."

(ix) FEATURE:
                    (A) NAME/KEY: Peptide
                    (B) LOCATION: 1
                    (D) OTHER INFORMATION: /note = "Phe has a 3-I and a 4-NH-2
                        group."

(ix) FEATURE:
                    (A) NAME/KEY: Peptide
                    (B) LOCATION: 2
                    (D) OTHER INFORMATION: /note = "Xaa is Chg."

(ix) FEATURE:
                    (A) NAME/KEY: Peptide
                    (B) LOCATION: 5
                    (D) OTHER INFORMATION: /note = "Amino acid is amidated at
                        the C- terminal."

(xi) SEQUENCE DESCRIPTION: SEQ ID NO:270:

Phe  Xaa  Arg  Leu  Pro
    1                   5

(2) INFORMATION FOR SEQ ID NO:271:

(i) SEQUENCE CHARACTERISTICS:
                    (A) LENGTH: 5 amino acids
                    (B) TYPE: amino acid
                    (D) TOPOLOGY: linear (ix) FEATURE:
                    (A) NAME/KEY: Peptide
                    (B) LOCATION: 1
                    (D) OTHER INFORMATION: /note = "Amino acid is acetylated at
                        the N- terminal."

( i x ) FEATURE:
  ( A ) NAME/KEY: Peptide
  ( B ) LOCATION: 1
  ( D ) OTHER INFORMATION: /note = "Phe has an iso-butyl and a
    p-amidino group."

( i x ) FEATURE:
  ( A ) NAME/KEY: Peptide
  ( B ) LOCATION: 2
  ( D ) OTHER INFORMATION: /note = "Xaa is Chg."

( i x ) FEATURE:
  ( A ) NAME/KEY: Peptide
  ( B ) LOCATION: 5
  ( D ) OTHER INFORMATION: /note = "Amino acid is amidated at
    the C- terminal."

( x i ) SEQUENCE DESCRIPTION: SEQ ID NO:271:

Phe Xaa Arg Leu Pro
1     5

( 2 ) INFORMATION FOR SEQ ID NO:272:

( i ) SEQUENCE CHARACTERISTICS:
  ( A ) LENGTH: 5 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note = "Amino acid is acetylated at
    the N- terminal."

( i x ) FEATURE:
  ( A ) NAME/KEY: Peptide
  ( B ) LOCATION: 1
  ( D ) OTHER INFORMATION: /note = "Phe has a p-amidino group."

( i x ) FEATURE:
  ( A ) NAME/KEY: Peptide
  ( B ) LOCATION: 2
  ( D ) OTHER INFORMATION: /note = "Xaa is Chg."

( i x ) FEATURE:
  ( A ) NAME/KEY: Peptide
  ( B ) LOCATION: 4
  ( D ) OTHER INFORMATION: /note = "Xaa is Gla."

( i x ) FEATURE:
  ( A ) NAME/KEY: Peptide
  ( B ) LOCATION: 5
  ( D ) OTHER INFORMATION: /note = "Amino acid is amidated at
    the C- terminal."

( x i ) SEQUENCE DESCRIPTION: SEQ ID NO:272:

Phe Xaa Arg Xaa Pro
1     5

( 2 ) INFORMATION FOR SEQ ID NO:273:

( i ) SEQUENCE CHARACTERISTICS:
  ( A ) LENGTH: 5 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note = "Amino acid is acetylated at
    the N- terminal."

( i x ) FEATURE:
  ( A ) NAME/KEY: Peptide
  ( B ) LOCATION: 1
  ( D ) OTHER INFORMATION: /note = "Phe has a p-amidino group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 4
    ( D ) OTHER INFORMATION: /note = "Xaa is Pen(CH-2COOH)."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:273:

Phe Xaa Arg Xaa Pro
1               5

( 2 ) INFORMATION FOR SEQ ID NO:274:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has a p-amidino group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:274:

Phe Xaa Arg Leu Pro
1               5

( 2 ) INFORMATION FOR SEQ ID NO:275:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has a pNH-2 group."

( i x ) FEATURE:
    ( A ) NAME/KEY: Peptide
    ( B ) LOCATION: 4
    ( D ) OTHER INFORMATION: /note = "Leu has a methyl group."

( i x ) FEATURE:
  ( A ) NAME/KEY: Peptide
  ( B ) LOCATION: 5
  ( D ) OTHER INFORMATION: /note = "Amino acid is amidated at the C- terminal."

( x i ) SEQUENCE DESCRIPTION: SEQ ID NO:275:

Phe Xaa Arg Leu Pro
1               5

( 2 ) INFORMATION FOR SEQ ID NO:276:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has a pNH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 3
    ( D ) OTHER INFORMATION: /note = "Xaa is ornithine-derived dimethylamidinium."

( i x ) FEATURE:
    ( A ) NAME/KEY: Peptide
    ( B ) LOCATION: 5
    ( D ) OTHER INFORMATION: /note = "Amino acid is amidated at the C- terminal."

( x i ) SEQUENCE DESCRIPTION: SEQ ID NO:276:

Phe Xaa Xaa Leu Pro
1               5

( 2 ) INFORMATION FOR SEQ ID NO:277:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note = "Amino acid is acetylated at the N- terminal."

( i x ) FEATURE:
    ( A ) NAME/KEY: Peptide
    ( B ) LOCATION: 1
    ( D ) OTHER INFORMATION: /note = "Phe has a pNH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5

( D ) OTHER INFORMATION: /note = "Amino acid is amidated at
the C- terminal."

( x i ) SEQUENCE DESCRIPTION: SEQ ID NO:277:

Phe Xaa Arg Leu Pro
1               5

( 2 ) INFORMATION FOR SEQ ID NO:278:

( i ) SEQUENCE CHARACTERISTICS:
( A ) LENGTH: 5 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note = "Amino acid is acetylated at
the N- terminal."

( i x ) FEATURE:
( A ) NAME/KEY: Peptide
( B ) LOCATION: 1
( D ) OTHER INFORMATION: /note = "Xaa is Nal(2)."

( i x ) FEATURE:
( A ) NAME/KEY: Peptide
( B ) LOCATION: 2
( D ) OTHER INFORMATION: /note = "Xaa is Chg."

( i x ) FEATURE:
( A ) NAME/KEY: Peptide
( B ) LOCATION: 5
( D ) OTHER INFORMATION: /note = "Amino acid is amidated at
the C- terminal."

( x i ) SEQUENCE DESCRIPTION: SEQ ID NO:278:

Xaa Xaa Arg Leu Pro
1               5

( 2 ) INFORMATION FOR SEQ ID NO:279:

( i ) SEQUENCE CHARACTERISTICS:
( A ) LENGTH: 5 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note = "Amino acid is acetylated at
the N- terminal."

( i x ) FEATURE:
( A ) NAME/KEY: Peptide
( B ) LOCATION: 1
( D ) OTHER INFORMATION: /note = "Phe has a p-amidino group."

( i x ) FEATURE:
( A ) NAME/KEY: Peptide
( B ) LOCATION: 2
( D ) OTHER INFORMATION: /note = "Xaa is Chg."

( i x ) FEATURE:
( A ) NAME/KEY: Peptide
( B ) LOCATION: 3
( D ) OTHER INFORMATION: /note = "Xaa is PalMe(3)."

( i x ) FEATURE:
( A ) NAME/KEY: Peptide
( B ) LOCATION: 5
( D ) OTHER INFORMATION: /note = "Amino acid is amidated at
the C- terminal."

( x i ) SEQUENCE DESCRIPTION: SEQ ID NO:279:

Phe Xaa Xaa Leu Pro
1               5

(2) INFORMATION FOR SEQ ID NO:280:

(i) SEQUENCE CHARACTERISTICS:
        (A) LENGTH: 6 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note = "Amino acid is acetylated at the N- terminal."

(ix) FEATURE:
        (A) NAME/KEY: Peptide
        (B) LOCATION: 2
        (D) OTHER INFORMATION: /note = "Xaa is Nal(2)."

(ix) FEATURE:
        (A) NAME/KEY: Peptide
        (B) LOCATION: 3
        (D) OTHER INFORMATION: /note = "Xaa is Chg."

(ix) FEATURE:
        (A) NAME/KEY: Peptide
        (B) LOCATION: 5
        (D) OTHER INFORMATION: /note = "Xaa is Hyp."

(ix) FEATURE:
        (A) NAME/KEY: Peptide
        (B) LOCATION: 6
        (D) OTHER INFORMATION: /note = "Amino acid is amidated at the C- terminal."

(xi) SEQUENCE DESCRIPTION: SEQ ID NO:280:

Lys Xaa Xaa Arg Xaa Glu
1               5

(2) INFORMATION FOR SEQ ID NO:281:

(i) SEQUENCE CHARACTERISTICS:
        (A) LENGTH: 5 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note = "Amino acid has a DIPA group at the N- terminal."

(ix) FEATURE:
        (A) NAME/KEY: Peptide
        (B) LOCATION: 1
        (D) OTHER INFORMATION: /note = "Phe has a p-amidino group."

(ix) FEATURE:
        (A) NAME/KEY: Peptide
        (B) LOCATION: 2
        (D) OTHER INFORMATION: /note = "Xaa is Chg."

(ix) FEATURE:
        (A) NAME/KEY: Peptide
        (B) LOCATION: 5
        (D) OTHER INFORMATION: /note = "Amino acid is amidated at the C- terminal."

(xi) SEQUENCE DESCRIPTION: SEQ ID NO:281:

Phe Xaa Arg Leu Pro
1               5

(2) INFORMATION FOR SEQ ID NO:282:

( i ) SEQUENCE CHARACTERISTICS:
  ( A ) LENGTH: 5 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note = "Amino acid is Isn at the N- terminal."

( i x ) FEATURE:
  ( A ) NAME/KEY: Peptide
  ( B ) LOCATION: 1
  ( D ) OTHER INFORMATION: /note = "Phe has a pNH-2 group."

( i x ) FEATURE:
  ( A ) NAME/KEY: Peptide
  ( B ) LOCATION: 2
  ( D ) OTHER INFORMATION: /note = "Xaa is Chg."

( i x ) FEATURE:
  ( A ) NAME/KEY: Peptide
  ( B ) LOCATION: 5
  ( D ) OTHER INFORMATION: /note = "Amino acid is amidated at the C- terminal."

( x i ) SEQUENCE DESCRIPTION: SEQ ID NO:282:

Phe Xaa Arg Leu Pro
1         5

( 2 ) INFORMATION FOR SEQ ID NO:283:

( i ) SEQUENCE CHARACTERISTICS:
  ( A ) LENGTH: 6 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note = "Xaa is Pza."

( i x ) FEATURE:
  ( A ) NAME/KEY: Peptide
  ( B ) LOCATION: 1
  ( D ) OTHER INFORMATION: /note = "Phe has a pNH-2 group."

( i x ) FEATURE:
  ( A ) NAME/KEY: Peptide
  ( B ) LOCATION: 2
  ( D ) OTHER INFORMATION: /note = "Xaa is Chg."

( i x ) FEATURE:
  ( A ) NAME/KEY: Peptide
  ( B ) LOCATION: 5
  ( D ) OTHER INFORMATION: /note = "Amino acid is amidated at the C- terminal."

( x i ) SEQUENCE DESCRIPTION: SEQ ID NO:283:

Xaa Phe Xaa Arg Leu Pro
1           5

( 2 ) INFORMATION FOR SEQ ID NO:284:

( i ) SEQUENCE CHARACTERISTICS:
  ( A ) LENGTH: 5 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note = "Amino acid is trifluoroacetylated at the N-terminal."

( i x ) FEATURE:
    ( A ) NAME/KEY: Peptide
    ( B ) LOCATION: 1
    ( D ) OTHER INFORMATION: /note = "Phe has an iso-butyl and a
        p-NH-2 group."

( i x ) FEATURE:
    ( A ) NAME/KEY: Peptide
    ( B ) LOCATION: 2
    ( D ) OTHER INFORMATION: /note = "Xaa is Chg."

( i x ) FEATURE:
    ( A ) NAME/KEY: Peptide
    ( B ) LOCATION: 5
    ( D ) OTHER INFORMATION: /note = "Amino acid is amidated at
        the C- terminal."

( x i ) SEQUENCE DESCRIPTION: SEQ ID NO:284:

Phe Xaa Arg Leu Pro
1               5

( 2 ) INFORMATION FOR SEQ ID NO:285:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is
            trifluoroacetylated at the N-terminal."

( i x ) FEATURE:
        ( A ) NAME/KEY: Peptide
        ( B ) LOCATION: 1
        ( D ) OTHER INFORMATION: /note = "Tyr has an iBu group."

( i x ) FEATURE:
        ( A ) NAME/KEY: Peptide
        ( B ) LOCATION: 2
        ( D ) OTHER INFORMATION: /note = "Xaa is Chg."

( i x ) FEATURE:
        ( A ) NAME/KEY: Peptide
        ( B ) LOCATION: 5
        ( D ) OTHER INFORMATION: /note = "Amino acid is amidated at
            the C- terminal."

( x i ) SEQUENCE DESCRIPTION: SEQ ID NO:285:

Tyr Xaa Arg Leu Pro
1               5

( 2 ) INFORMATION FOR SEQ ID NO:286:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note = "Amino acid is
            trifluoroacetylated at the N-terminal."

( i x ) FEATURE:
        ( A ) NAME/KEY: Peptide
        ( B ) LOCATION: 1
        ( D ) OTHER INFORMATION: /note = "Tyr has an iBu group."

( i x ) FEATURE:
        ( A ) NAME/KEY: Peptide
        ( B ) LOCATION: 3

(D) OTHER INFORMATION: /note = "Xaa is ornithine-derived dimethylamidinium."

(ix) FEATURE:
 (A) NAME/KEY: Peptide
 (B) LOCATION: 5
 (D) OTHER INFORMATION: /note = "Amino acid is amidated at the C- terminal."

(xi) SEQUENCE DESCRIPTION: SEQ ID NO:286:

Tyr Ile Xaa Leu Pro
1               5

(2) INFORMATION FOR SEQ ID NO:287:

(i) SEQUENCE CHARACTERISTICS:
  (A) LENGTH: 5 amino acids
  (B) TYPE: amino acid
  (D) TOPOLOGY: linear (ix) FEATURE:
  (A) NAME/KEY: Peptide
  (B) LOCATION: 1
  (D) OTHER INFORMATION: /note = "Amino acid has a tosyl group at the N-terminal."

(ix) FEATURE:
  (A) NAME/KEY: Peptide
  (B) LOCATION: 1
  (D) OTHER INFORMATION: /note = "Phe has a pNH-2 group."

(ix) FEATURE:
  (A) NAME/KEY: Peptide
  (B) LOCATION: 2
  (D) OTHER INFORMATION: /note = "Xaa is Chg."

(ix) FEATURE:
  (A) NAME/KEY: Peptide
  (B) LOCATION: 5
  (D) OTHER INFORMATION: /note = "Amino acid is amidated at the C- terminal."

(xi) SEQUENCE DESCRIPTION: SEQ ID NO:287:

Phe Xaa Arg Leu Pro
1               5

(2) INFORMATION FOR SEQ ID NO:288:

(i) SEQUENCE CHARACTERISTICS:
  (A) LENGTH: 4 amino acids
  (B) TYPE: amino acid
  (D) TOPOLOGY: linear (ix) FEATURE:
  (A) NAME/KEY: Peptide
  (B) LOCATION: 1
  (D) OTHER INFORMATION: /note = "Amino acid is acetylated at the N- terminal."

(ix) FEATURE:
  (A) NAME/KEY: Peptide
  (B) LOCATION: 2
  (D) OTHER INFORMATION: /note = "Xaa is Chg."

(ix) FEATURE:
  (A) NAME/KEY: Peptide
  (B) LOCATION: 4
  (D) OTHER INFORMATION: /note = "Xaa is Pip."

(ix) FEATURE:
  (A) NAME/KEY: Peptide
  (B) LOCATION: 4
  (D) OTHER INFORMATION: /note = "Amino acid is amidated at the C- terminal."

(xi) SEQUENCE DESCRIPTION: SEQ ID NO:288:

```
         Tyr  Xaa  Arg  Xaa
         1
```

(2) INFORMATION FOR SEQ ID NO:289:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (ix) FEATURE:
        (A) NAME/KEY: Peptide
        (B) LOCATION: 1
        (D) OTHER INFORMATION: /note = "Phe has a p-amidino bond and a DIPA bond."

(ix) FEATURE:
        (A) NAME/KEY: Peptide
        (B) LOCATION: 2
        (D) OTHER INFORMATION: /note = "Xaa is Chg"

(ix) FEATURE:
        (A) NAME/KEY: Peptide
        (B) LOCATION: 5
        (D) OTHER INFORMATION: /note = "Amino acid is amidated at the C- terminal."

(xi) SEQUENCE DESCRIPTION: SEQ ID NO:289:

```
         Phe  Xaa  Arg  Leu  Pro
         1                    5
```

(2) INFORMATION FOR SEQ ID NO:290:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (ix) FEATURE:
        (A) NAME/KEY: Peptide
        (B) LOCATION: 1
        (D) OTHER INFORMATION: /note = "Amino acid is acetylated at the N- terminal."

(ix) FEATURE:
        (A) NAME/KEY: Peptide
        (B) LOCATION: 5
        (D) OTHER INFORMATION: /note = "Amino acid is amidated at the C- terminal."

(xi) SEQUENCE DESCRIPTION: SEQ ID NO:290:

```
         Tyr  Ile  Arg  Leu  Ala
         1                    5
```

FACTOR XA INHIBITORS

This application is a continuation of U.S. application Ser. No. 08/428,404, filed Apr. 25, 1995, now abandoned, which is a continuation-in-part of U.S. application Ser. No. 08/233,054, filed Apr. 26, 1994, now abandoned.

BACKGROUND OF THE INVENTION

FIELD OF THE INVENTION

The present invention relates generally to the inhibition of blood clotting proteins and more particularly to specific inhibitors of the blood clotting enzyme factor Xa.

BACKGROUND INFORMATION

The ability to form blood clots is vital to survival. In certain disease states, however, the formation of blood clots within the circulatory system is itself a source of morbidity. Thus, it sometimes can be desirable to prevent blood clot formation. However, it is not desirable to completely inhibit the clotting system because life threatening hemorrhage would ensue.

In order to reduce the intravascular formation of blood clots, those skilled in the art have endeavored to develop an effective inhibitor of prothrombinase or of factor Xa, which is incorporated into the prothrombinase complex where it activates thrombin during clot formation.

Appropriate concentrations of a factor Xa inhibitor would increase the level of prothrombinase forming agents required to initiate clotting but would not unduly prolong the clotting process once a threshold concentration of thrombin had been obtained. However, despite the long standing recognition of the desirability of such an inhibitor, there is at present no effective, specific factor Xa inhibitor in clinical use.

In many clinical applications there is a great need for anti-coagulant treatment. The currently available drugs are not satisfactory in many specific clinical applications. For example, nearly 50% of patients who undergo a total hip replacement develop deep vein thrombosis (DVT). The currently approved therapies include fixed dose low molecular weight heparin (LMWH) and variable dose heparin. Even with these drug regimes, 10% to 20% of patients develop DVT and 5% to 10% develop bleeding complications.

Another clinical situation for which better anti-coagulants are needed concerns subjects undergoing transluminal coronary angioplasty and at risk for myocardial infarction or suffering from crescendo angina. The present, conventionally accepted therapy, which consists of administering heparin and aspirin, is associated with a 6% to 8% abrupt vessel closure rate within 24 hours of the procedure. The rate of bleeding complications requiring transfusion therapy due to the use of heparin also is approximately 7%. Moreover, even though delayed closures are significant, administration of heparin after the termination of the procedures is of little value and can be detrimental.

The most widely used blood-clotting inhibitors are heparin and the related sulfated polysaccharides, LMWH and heparin sulfate. These molecules exert their anti-clotting effects by promoting the binding of a natural regulator of the clotting process, anti-thrombin III, to thrombin and to factor Xa. The inhibitory activity of heparin primarily is directed toward thrombin, which is inactivated approximately 100 times faster than factor Xa. Although relative to heparin, heparin sulfate and LMWH are somewhat more potent inhibitors of Xa than of thrombin, the differences in vitro are modest (3–30 fold) and effects in vivo can be inconsequential. Hirudin and hirulog are two additional thrombin-specific anticoagulants presently in clinical trials. However, these anticoagulants, which inhibit thrombin, also are associated with bleeding complications.

Preclinical studies in baboons and dogs have shown that specific inhibitors of factor Xa prevent clot formation without producing the bleeding side effects observed with direct thrombin inhibitors. Such factor Xa inhibitors include, for example, 2,7-bis-(4-amidino benzylidene)-cycloheptanone and Nα-tosylglycyl-3-amidinophenylalanine methyl ester ("TENSTOP"), which have effective inhibitory concentrations ($K_i$'s) of about 20 nM and 800 nM, respectively. (+)-(2S)-2-(4({(3S)-1-acetimidoyl-3-pyrrolidinyl}oxy)phenyl)-3-(7-amidino-2-naphthyl)propanoic acid also is representative of a class of factor Xa inhibitors (Katakura et al., *Biochem. Biophys. Res. Comm.* 197:965–972 (1993)). Thus far, however, these compounds have not been developed clinically.

Specific protein inhibitors of factor Xa also have been identified and include, for example, antistasin ("ATS") and tick anticoagulant peptide ("TAP"). ATS, which isolated from the leech, *Haementerin officinalis*, contains 119 amino acids and has a $K_i$ for factor Xa of 0.05 nM. TAP, which is isolated from the tick, Ornithodoros moubata, contains 60 amino acids and has a $K_i$ for factor Xa of about 0.5 nM.

The effectiveness of recombinantly-produced ATS and TAP have been investigated in a number of animal model systems. Both inhibitors decrease bleeding time compared to other anticoagulants and prevent clotting in a thromboplastin-induced, ligated jugular vein model of deep vein thrombosis. The results achieved in this model correlate with results obtained using the current drug of choice, heparin.

Subcutaneous ATS also was found to be an effective treatment in a thrombopiastin-induced model of disseminated intravascular coagulation (DIC). TAP effectively prevents "high-shear" arterial thrombosis and "reduced flow" caused by the surgical placement of a polyester ("DACRON") graft at levels that produced a clinically acceptable prolongation of the activated partial thromboplastin time (aPTT), i.e., less than about two fold prolongation. By comparison, standard heparin, even at doses causing a five fold increase in the aPTT, did not prevent thrombosis and reduced flow within the graft. The aPTT is a clinical assay of coagulation which is particularly sensitive to thrombin inhibitors.

ATS and TAP have not been developed clinically. One major disadvantage of these two inhibitors is that administration of the required repeated doses causes the generation of neutralizing antibodies, thus limiting their potential clinical use. Moreover, the sizes of TAP and ATS render oral administration impossible, further restricting the number of patients able to benefit from these agents.

A specific inhibitor of factor Xa would have substantial practical value in the practice of medicine. In particular, a factor Xa inhibitor would be effective under circumstances where the present drugs of choice, heparin and related sulfated polysaccharides, are ineffective or only marginally effective. Thus, there exists a need for a low molecular weight, factor Xa specific blood clotting inhibitor that is effective, but does not cause unwanted side effects. The present invention satisfies this need and provides related advantages as well.

SUMMARY OF THE INVENTION

The present invention provides compounds that specifically inhibit factor Xa activity. A compound of the invention has the structure $X_1$-Y-I-R-$X_2$, wherein $X_1$ is a hydrogen (H), acyl, alkyl or arylalkyl group, or one or more amino acids, and $X_2$ is a modified C-terminal group, one or more carboxy-protecting groups (see below), one or more amino acids, or other substituents, and Y, I and R refer to the amino acids tyrosine, isoleucine and arginine, respectively, and to peptidomimetic or organic structures that have the same functional activities as tyrosine, isoleucine and arginine, respectively. In addition, a compound of the invention has the structure, A1-A2-(A3)$_m$—B, as defined herein.

A compound of the invention can be linear or cyclic, between about 2 and 43 residues in length and modified at the N-terminus or C-terminus or both. Such compounds exhibit a specific inhibition of factor Xa activity with a $K_i \leq 100 \mu M$, preferably a $K_i \leq 2$ nM, and do not substantially inhibit the activity of other proteases involved in the coagulation cascade. Specific examples of such compounds include Ac-Tyr-Ile-Arg-Leu-Ala—NH$_2$ (SEQ ID NO:2); Ac-Tyr-Ile-Arg-Leu-Pro—NH$_2$ (SEQ ID NO:3); Ac-(iBu)Tyr-Ile-Arg-Leu-Pro—NH$_2$ (SEQ ID NO:4); Ac-Tyr-Ile-Arg—N(CH$_3$)O(CH$_3$); Ac-Tyr-{Ψ(CH$_2$NH)}-Ile-Arg-Leu-Pro—NH$_2$ (SEQ ID NO:5)(where "Ψ" indicates a pseudo peptide bond, which, for example, can be a reduced bond as indicated by "(CH$_2$NH)"; pseudo peptide bonds are indicated by "Ψ" enclosed in brackets, "{Ψ}"); Ac-Tyr-Ile-Arg—NH—CH$_2$(4-Pyridyl); Ac-Tyr-Ile-{ΨCH$_2$NH)}-Arg-Leu-Pro—NH$_2$ (SEQ ID NO:6); Ac-Tyr-Chg-Arg(NO$_2$)-{Ψ(CH$_2$NH)}-Leu—NH$_2$; Ac-Tyr-Ile-Arg-{Ψ(COCH$_2$)}-Gly-Pro—NH$_2$ (SEQ ID NO:8); Ac-Tyr-Ile-Dab(N$^γ$—C$_3$H$_7$N)-Leu-Ala—NH$_2$ (SEQ ID NO:9); Ac-Tyr-Ile-PalMe(3)—NH2; Tyr-Ile-Arg—NH$_2$; (D)-Tyr-Ile-Arg-Leu-Pro—NH$_2$; Ac-(Bzl)Gly-(Chx)Gly-(3-guanidopropyl)Gly—NH$_2$; Cyclo(Gly-Tyr-Ile-Arg-Gly)(SEQ ID NO:10); Tfa-(iBu)Tyr-Chg-Arg-Leu-Pro—NH$_2$ (SEQ ID NO:11); Ac-pAph-Chg-Arg-Leu-Pro—NH$_2$ (SEQ ID NO:12); Ac-Nal (2)-Chg-Arg-Leu-Pro—NH$_2$ (SEQ ID NO:13); Ac-pAph-Chg-PalMe(3)—NH$_2$; and pharmaceutically acceptable salts and C-terminal derivatives such as amides, esters, alcohols and aldehydes thereof (see, also, Table 5). Methods of specifically inhibiting the activity of factor Xa and of inhibiting blood-clotting in an individual also are provided. Methods of detecting factor Xa levels or activity are provided as well.

DETAILED DESCRIPTION OF THE INVENTION

Figure 1:
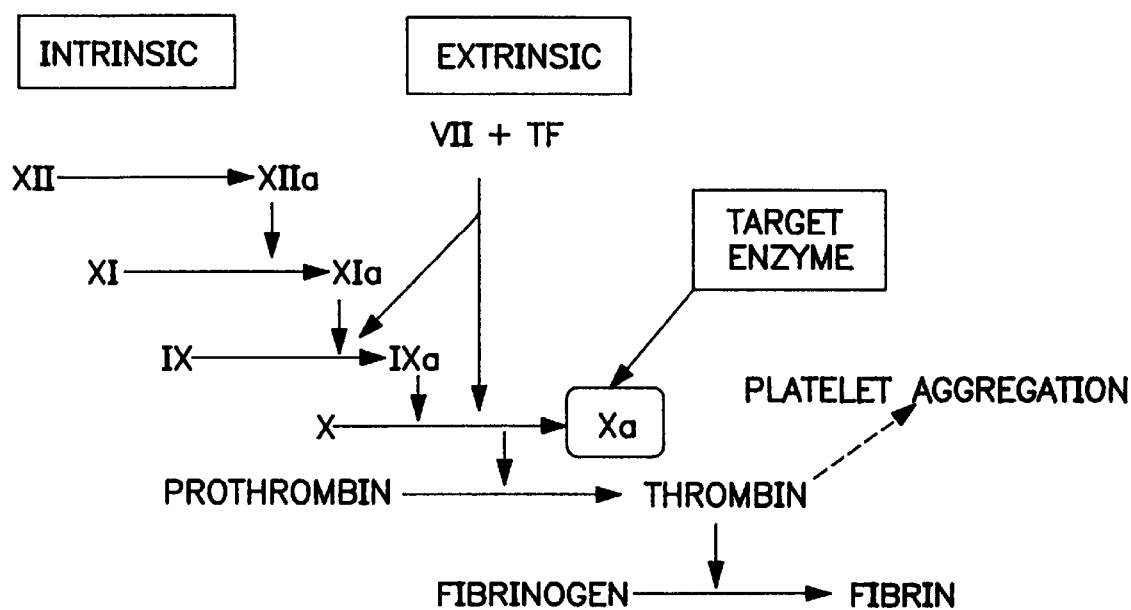
FIG. 1 is a schematic diagram of the blood coagulation cascade.

Blood coagulation is a complex process involving a progressively amplified series of enzyme activation reactions in which plasma zymogens are sequentially activated by limited proteolysis. Mechanistically the blood coagulation cascade has been divided into intrinsic and extrinsic pathways, which converge at the activation of factor X; subsequent generation of thrombin proceeds through a single common pathway (see FIG. 1).

Present evidence suggests that the intrinsic pathway plays an important role in the maintenance and growth of fibrin formation, while the extrinsic pathway is critical in the initiation phase of blood coagulation. It is generally accepted that blood coagulation is physically initiated upon formation of a tissue factor/factor VIIa complex. Once formed, this complex rapidly initiates coagulation by activating factors IX and X. The newly generated factor Xa then forms a one-to-one complex with factor Va and phospholipids to form a prothrombinase complex, which is responsible for converting soluble fibrinogen to insoluble fibrin. As time progresses, the activity of the factor VIIa/tissue factor complex (extrinsic pathway) is suppressed by a Kunitz-type protease inhibitor protein, TFPI, which, when complexed to factor Xa, can directly inhibit the proteolytic activity of factor VIIa/tissue factor. In order to maintain the coagulation process in the presence of an inhibited extrinsic system, additional factor Xa is produced via the thrombin-mediated activity of the intrinsic pathway. Thus, thrombin plays a dual autocatalytic role, mediating its own production and the conversion of fibrinogen to fibrin.

The autocatalytic nature of thrombin generation is an important safeguard against uncontrolled bleeding and it ensures that, once a given threshold level of prothrombinase is present, blood coagulation will proceed to completion, effecting, for example, an end of the hemorrhage. Thus, it is most desirable to develop agents that inhibit coagulation without directly inhibiting thrombin.

The present invention provides YIR peptides, which are compounds that inhibit factor Xa activity but do not substantially inhibit the activity of other proteases involved in the blood coagulation pathway. As used herein, the term "compound" or "YIR peptide" refers to a non-naturally occurring Tyr-Ile-Arg (YIR) peptide and analogues and mimetics thereof, which can inhibit factor Xa activity. The YIR sequence, itself, is referred to herein as the "YIR motif" and consists of the tripeptide tyrosine-isoleucine-arginine or a functional equivalent thereof such as pAph-Chg-PalMe(3), pAph-Chg-PalMe(3)—NH$_2$ and pAph-Chg-AMP (4) (see Table 1 for abbreviations). Such compounds of the invention contain at least one YIR motif or a functional equivalent thereof and are cap able of specifically inhibiting the activity of factor Xa. For convenience, the terms compound and "YIR peptide" are used broadly herein to refer to the peptides of the invention, including functional equivalents such as peptide analogs, peptide mimetics and synthetic organic compounds. A function equivalent of a YIR peptide of the invention can be characterized, in part, by having a structure as disclosed herein and by having a $K_i \leq 100 \mu M$ for inhibiting factor Xa activity (see Example XXXVII).

Peptide analogs of a YIR peptide of the invention include, for example, peptides containing non-naturally occurring amino acids or chemically modified amino acids, provided the compound retains factor Xa inhibitory activity (see, for example, Table 2). Similarly, peptide mimetics are non-amino acid chemical structures that mimic the structure of a YIR peptide of the invention and retain factor Xa inhibitor activity. Such mimetics are characterized generally as exhibiting similar physical characteristics such as size, charge or hydrophobicity that is presented in the appropriate spatial orientation as found in the normal YIR peptide counterpart. A specific example of a peptide mimetic is a compound in which the amide bond between one or more of the amino acids is replaced, for example, by a carbon-carbon bond or other bond as is well known in the art (see, for example, Sawyer, in *Peptide Based Drug Design* pp. 387–422 (ACS, Washington D.C. 1995), which is incorporated herein by reference). Thus, the invention further provides factor Xa inhibitory compounds having the structure A1-A2-(A3)$_m$—B (SEQ ID NO:14), where m is 0 or 1, as disclosed herein (see below). Examples of such peptides, which can be mimetic compounds, are provided herein.

As used herein, the term "amino acid" is used in its broadest sense to mean the twenty naturally occurring amino acids, which are translated from the genetic code and comprise the building blocks of proteins, including, unless specifically stated otherwise, L-amino acids and D-amino acids, as well as chemically modified amino acids such as amino acid analogs, naturally-occurring amino acids that are not usually incorporated into proteins such as norleucine, and chemically synthesized compounds having properties known in the art to be characteristic of an amino acid. For example, analogs or mimetics of phenylalanine or proline, which allow the same conformational restriction of the peptide compounds as natural Phe or Pro, are included within the definition of "amino acids" and are known to those skilled in the art. Such analogs and mimetics are referred to herein as "functional equivalents" of an amino acid. Other examples of amino acids and amino acids analogs are listed by Roberts and Vellaccio (*The Peptides: Analysis, Synthesis, Biology*, Eds. Gross and Meienhofer, Vol. 5, p. 341, Academic Press, Inc., N.Y. 1983, which is incorporated herein by reference). Abbreviations of amino acids, amino acid analogs and mimetic structures are listed in Table 1.

TABLE 1

Abbreviations used in the specification

| Compound | Abbreviation #1 | Abbreviation #2 |
|---|---|---|
| Acetyl | Ac | |
| Alanine | Ala | A |
| 3-(2-Thiazolyl)-L-alanine | Tza | |
| Amidine | AMDN | |
| Amidoxime (C(NH$_2$)=N—OH) | (CNOH.NH$_2$) | |
| (N-methylpyridinium) methyl | AMP | |
| (4-(N-methylpyridinium)) methyl | AMP(4) | |
| 1-(N-Methylpyridinium) ethy-1-yl | AEMP | |
| 1-(4-(N-methylpyridinium) eth-1-yl | AEMP(4) | |
| Arginine | Arq | R |
| Asparagine | Asn | N |
| Aspartic acid | Asp | D |
| Benzoyl | Bz | |
| 2-Benzofuranecarboxy | Bzf | |
| Benzyl | Bzl | |
| Benzyloxycarbonyl | Cbz | |
| 5-Benzimidazolecarboxy | 5-Bzim | |
| t-Butyloxycarbonyl | Boc | |
| Benzotriazol-1-yloxy-tris-(dimethylamino)-phosphonium-hexafluorophosphate | Bop | |
| β-Alanine | βAla | |
| β-Valine | βVal | |
| β-(2-Pyridyl)-alanine | Pal(2) | |
| β-(3-Pyridyl)-alanine | Pal(3) | |
| β-(4-Pyridyl)-alanine | Pal(4) | |
| β-(3-N-Methylpyridinium)-alanine | PalMe(3) | |
| Bromo-tris-pyrrolidino-phosphonium-hexafluorophosphate | PyBrOP | |
| t-Butyl | tBu, But | |
| t-Butyloxycarbonyl | Boc | |
| Caffeic acid | Caff | |
| Carbonyldiimidazole | CDI | |
| Cysteine | Cys | C |
| 5-chloroindole-2-carboxy | CICA | |
| Cyclohexyl | Chx | |
| Cyclohexylalanine | Cha | |
| Cyclohexylglycine | Chg | |
| 2,4-Diaminobutyric acid | Dab | |

TABLE 1-continued

Abbreviations used in the specification

| Compound | Abbreviation #1 | Abbreviation #2 |
|---|---|---|
| Dab-derived dimethylamidinium | Dab (N$^\gamma$-C$_3$H$_7$N) | |
| 2,3-Diaminopropionic acid | Dap | |
| Dap-derived dimethylamidinium | Dap(N$^\beta$-C$_3$H$_7$N) | |
| 3,5-Dinitrotyrosine | Tyr(3,5-NO$_2$) | Y(3,5-NO$_2$) |
| 3,5-Diiodotyrosine | Tyr(3,5-I) | Y(3,5-I) |
| 3,5-Dibromotyrosine | Tyr(3,5-Br) | Y(3,5-Br) |
| N,N-diisobutylcarboxamide | DIBA | |
| N,N-diisopropylcarboxamide | DIPA | |
| 4-N,N-Dimethylamino pyridine | DMAP | |
| 9-Fluorenylmethyloxy-carbonyl | Fmoc | |
| 5-Fluoroindole-2-carboxy | FICA | |
| Formyl | For | |
| Glutamine | Gln | Q |
| Glutamic acid | Glu | E |
| γ-Carboxyglutamic acid | Gla | |
| Glycine | Gly | G |
| Histidine | His | H |
| Homoarginine | hArq | hR |
| 5-Hydroxyindole-2-carboxy | 5-Hic | |
| N-Hydroxybenzotriazole | HOBt | |
| 3-Hydroxyproline | Hyp | |
| Iminodiacetic acid | Ida | |
| 5-aminoindole-2-carboxy | 5AM2IN | |
| 5-nitroindole-2-carboxy | 5NOINDC | |
| DL-Indoline-2-carboxy | 2INCA | |
| Isobutyl | iBu | |
| Isoleucine | Ile | I |
| Isonicotinic acid | Isn | |
| N-Methyl-isnicotinic acid | IsnMe | |
| Isonipecotic acid | Ina | |
| Isopropanol | iPrOH | |
| 1-Isoquinolinecarboxy | 1-Iqc | |
| 3-Isoquinolinecarboxy | 3-Iqc | |
| Leucine | Leu | L |
| tert-Leucine | Tle | |
| Lysine | Lys | K |
| Mercapto-β,β-cyclopentamethylene-propionic acid | Mpp | |
| Mercaptoacetic acid | Mpa | |
| Mercaptopropionic acid | Mpr | |
| Methanol | MeOH | |
| Methionine | Met | M |
| 4-Morpholinocarbonylamide | MORA | |
| N-methylmorpholine | NMM | |
| 1-Naphthylalanine | Nal(1) | |
| 2-Naphthylalanine | Nal(2) | |
| Nicotinic acid | Nic | |
| Nipecotic acid | Npa | |
| N-methyl nicotinic acid | NicMe | |
| Norarginine | nArg | nR |
| Norleucine | Nle | nL |
| Norvaline | Nva | nV |
| Ornithine | Orn | |
| Ornithine-derived dimethylamidinium | Orn(N$^6$-C$_3$H$_7$N) | |
| Phenyl | Ph | |
| Phenylalanine | Phe | F |
| p-Guanidinophenylalanine | Phe(Gua) | F (pGua) |
| p-Aminophenylalanine | Phe(NH$_2$) | F(pNH$_2$) |
| p-Chlorophenylalanine | Phe(Cl) | F(pCl) |
| p-Flurophenylalanine | Phe(F) | F(pF) |
| p-Nitrophenylalanine | Phe(NO$_2$) | F(pNO$_2$) |
| p-Hydroxyphenylglycine | Pgl(OH) | |
| p-Toluenesulfonyl | Tos | |
| 2,2,5,7,8-Pentamethyl-chroman-6-sulfonyl | Pmc | |
| m-Amidinophenylalanine | mAph | |
| p-Amidinophenylalanine | pAph | |
| Phenylglycine | Pgl | |

TABLE 1-continued

Abbreviations used in the specification

| Compound | Abbreviation #1 | Abbreviation #2 |
|---|---|---|
| Phenylmalonic acid | Pma | |
| Piperidinyl | PIP | |
| 1-Piperidinocarbonyl amide | PIPA | |
| L-Pipecolonic acid | Pip | |
| Proline | Pro | P |
| 2-Pyrazinecarboxy | Pza | |
| 2-Quinolinecarboxy | 2-Qca | |
| 4-Quinolinecarboxy | 4-Qca | |
| Sarcosine | Sar | |
| S-tert-butyl | SBut | |
| SCAL linker attached to "TENTAGEL" | SCAL-TG | |
| Serine | Ser | S |
| Tetrahydroisoquinoline-3-carboxyl | Tic | |
| Threonine | Thr | T |
| Trifluoroacetyl | Tfa | |
| Tryptophan | Trp | W |
| Tyrosine | Tyr | Y |
| 3-iodotyrosine | Tyr(3-I) | Y(3-I) |
| O-Methyl tyrosine | Tyr(Me) | Y(Me) |
| Valine | Val | V |

*Amino acids of D configuration are denoted either by D- prefix using three-letter code (eg., D-Ala, D-Cys, D-Asp, D-Trp) or with lower case letters using the one-letter code (a, c, d, w, respectively).

As used herein, the term "factor Xa activity" refers to the ability of factor Xa, by itself or in the assembly of subunits known as the prothrombinase complex, to catalyze the conversion of prothrombin to thrombin. When used in reference to factor Xa activity, the term "inhibition" includes both the direct and the indirect inhibition of factor Xa activity. Direct inhibition of factor Xa activity can be accomplished, for example, by the binding of a YIR peptide of the invention to factor Xa or to prothrombinase so as to prevent the binding of prothrombin to the prothrombinase complex active site. Indirect inhibition of factor Xa activity can be accomplished, for example, by the binding of a compound of the invention to soluble factor Xa so as to prevent its assembly into the prothrombinase complex.

As used herein, the term "specific" when used in reference to the inhibition of factor Xa activity means that a YIR peptide can inhibit factor Xa activity without substantially inhibiting the activity of other specified proteases, including plasmin and thrombin (using the same concentration of the inhibitor). Such proteases are involved in the blood coagulation and fibrinolysis cascade (see Table 2; see, also, Example XXVII).

TABLE 2

Inhibitory activities of selected compounds against five enzymes

| | $K_i$ ($\mu$M) | | | | |
|---|---|---|---|---|---|
| Compound | Xa | Thrombin | Plasmin | Trypsin | Elastase |
| Ac-Y-I-R-L-A-A-F-T (SEQ ID NO.:260) | 1.5 | 100 | NT | >200* | >100 |
| Ac-Y-I-R-L-P (SEQ ID NO. 261) | 0.5 | >200 | >200 | >200 | >100 |
| y-I-R-L-P | 0.2 | >200 | >200 | >200 | >100 |
| Ac-(iBu)Y-I-R-L-P | 0.04 | 25 | >200 | NT | >100 |
| "TENSTOP" | 2 | 2 | >200 | NT | >200 |

*Indicates that there was no significant inhibition of enzyme activity at the highest concentration of compound (indicated) tested.

The results in Table 2 demonstrate that the YIR peptides of the invention are useful as inhibitors of factor Xa but do not substantially inhibit the activity of other serine proteases such as thrombin or plasmin, which are involved in the process of blood coagulation and fibrinolysis.

As used herein, the term "substituent" refers to any of various chemical groups that is substituted onto the peptide backbone or side chain of a peptide, peptide analogue, mimetic or organic compound disclosed herein. A substituent can include any of a variety of different moieties known to those skilled in the art (see, for example, Giannis and Kolter, *Angew. Chem. Int. Ed. Engl.* 32:1244–1267 (1993), which is incorporated herein by reference). Numerous examples demonstrating the substitution of a substituent are disclosed herein including, for example, substitution of a $pNH_2$ substituent onto phenylalanine to obtain $F(pNH_2)$ and the substitution of a halogen onto a tyrosine to obtain, for example Y(3-I) or Y(3,5-I). In addition, a substituent can be, for example, a heteroatom such as nitrogen (N; see, for example, Pal), oxygen (O; see, for example, O-methyltyrosine) or sulfur (S; see, for example, $Tyr(SO_3H)$), which can be substituted with a substituent. Thus, an N-, S- or O-containing moiety such as $—SO_3H$ is considered a "substituent" as defined herein. Furthermore, a substituent can be an amino-protecting group or carboxy-protecting group.

As used herein, the term "alkyl" is used in the broadest sense to mean saturated or unsaturated, linear, branched or cyclic chains of about 1 to 13 carbon atoms. Thus, the term "alkyl" includes, for example, methyl, ethyl, n-propyl, isopropyl, sec-butyl, 1-methylbutyl, 2,2-dimethylbutyl, 2-methylpentyl, 2,2-dimethylpropyl, n-pentyl and n-hexyl groups, alkylene groups, cyclic chains of carbon atoms such cyclohexyl and cyclopentyl groups, as well as combinations of linear or branched chains and cyclic chains of carbon atoms such as a methyl-cyclohexyl or cyclopropyl-methylene group. In addition, it should be recognized that an alkyl as defined herein can be substituted with a substituent. Similarly, the term "acyl" is used in its broadest sense to mean saturated or unsaturated, linear, branched or cyclic chains of about 1 to 13 carbon atoms, which contain a carboxyl group. Thus, the term "acyl" encompasses, for example, groups such as formyl, acetyl, benzoyl and the like.

The term "aryl" refers to aromatic groups containing about 5 to 13 carbon atoms and at least one "ring" group having a conjugated pi electron system. Examples of aryls include, for example, heterocyclic aryl groups, biaryl groups, and analogues and derivatives thereof, all of which optionally can be substituted with one or more substituents. The term "arylalkyl" refers to an alkyl as defined above substituted with an aryl group. Suitable arylalkyl groups include benzyl, picolyl and the like, all of which optionally can be substituted.

The terms "heteroalkyl," "heteroarylalkyl" and "heteroaryl" also are used herein and refer to an alkyl, an arylalkyl and an aryl, respectively, that is substituted with one or more heteroatoms such as a N, O or S atom. In addition, the term "heterocyclic" is used in reference to a cyclic alkyl or an aryl group that is substituted with one or more heteroatoms. Numerous examples of heteroalkyls, heteroarylalkyls, heteroaryls and heterocyclics are disclosed, for example, in Tables 1 and 3, or are otherwise known in the art.

The peptides of the invention can be modifies at the N-terminus or the C-terminus using an amino-protecting group or carboxy-protecting group, respectively. Numerous such modifications are disclosed herein (see, for example, Table 3). The N-terminus of a peptide or peptide analog can be chemically modified such that the N-terminus amino group is substituted, for example, by an acetyl, cyclopentyicarboxy, isoquinolylcarboxy, furoyl, tosyl, pyrazinecarboxy or other such group, which can be substituted by a substituent as described above. The N-terminal amino group also can be substituted, for example, with a reverse amide bond. It should be recognized that the term "amino group" is used broadly herein to refer to any free amino group, including a primary, secondary or tertiary amino group, present in a peptide. In comparison, the term "N-terminus" refers to the α-amino group of the first amino acid present in a peptide written in the conventional manner.

The N-terminus of a peptide of the invention can be protected by linking thereto an amino-protecting group. The term "amino-protecting group" is used broadly herein to refer to a chemical group that can react with a free amino group, including, for example, the α-amino group present at the N-terminus of a peptide of the invention. By virtue of reacting therewith, an amino-protecting group protects the otherwise reactive amino group against undesirable reactions as can occur, for example, during a synthetic procedure or due to exopeptidase activity on a final compound. Modification of an amino group also can provide additional advantages, including, for example, increasing the solubility or the activity of the compound. Various amino-protecting groups are disclosed herein (see Table 3) or otherwise known in the art and include, for example, acyl groups such as an acetyl, picoloyl, tert-butylacetyl, tert-butyloxycarbonyl, benzyloxycarbonyl, benzoyl groups, including, for example, a benzyloxime such as a 2-aryl-2-O-benzyloxime (see Example XVI), as well as an aminoacyl residue, which itself can be modified by an amino-protecting group. Other amino-protecting groups are described, for example, in *The Peptides*, eds. Gross and Meienhofer, Vol. 3 (Academic Press, Inc., N.Y. 1981); and by Greene and Wuts, in *Protective Groups in Organic Synthesis* 2d ed., pages 309–405 (John Wiley & Sons, New York (1991), each of which is incorporated herein by reference. The product of any such modification of the N-terminus amino group of a peptide or peptide analog of the invention is referred to herein as an "N-terminal derivative."

Similarly, a carboxy group such as the carboxy group present at the C-terminus of a peptide can be chemically modified using a carboxy-protecting group. The terms "carboxy group" and "C-termnius" are used in a manner consistent with the terms "amino group" and "N-terminus" as defined above. A carboxy group such as that present at the C-terminus of a peptide can be modified by reduction of the C-terminus carboxy group to an alcohol or aldehyde or by formation of an oral ester or by substitution of the carboxy group with a substituent such as a thiazolyl, cyclohexyl or other group. Oral esters are well known in the art and include, for example, alkoxymethyl groups such as methoxymethyl, ethoxymethyl, iso-propoxymethyl and the like; the α-($C_1$ to $C_4$) alkoxyethyl groups such as methoxyethyl, ethoxyethyl, propoxyethyl, isopropoxyethyl and the like; the 2-oxo-1,3-dioxolen-4-ylmethyl groups such as 5-methyl-2-oxo-1,3-dioxolen-4-ylmethyl, 5-phenyl-2-oxo-1,3-dioxolen-4-ylmethyl and the like; the $C_1$ to $C_3$ alkylthiomethyl groups such as methylthiomethyl, ethylthiomethyl, isopropylthiomethyl and the like; the acyloxymethyl groups such as pivaloyloxymethyl, α-acetoxymethyl and the like; the ethoxycarbonyl-1-methyl group; the α-acyloxy-α-substituted methyl groups such as α-acetoxyethyl, the 3-phthalidyl or 5,6-dimethylphthalidyl groups, the 1-($C_1$ to $C_4$ alkyloxycarbonyloxy)eth-1-yl groups such as the 1-(ethoxycarbonyloxy)eth-1-yl group; and the 1-($C_1$ to $C_4$ alkylaminocarbonyloxy)eth-1-yl group such as the 1-(methylaminocarbonyloxy)eth-1-yl group.

A peptide of the invention can be modified by linking thereto a carboxy-protecting group. Carboxy-protecting groups are well known in the art and, by virtue of being bound to a peptide, protect a carboxy group against undesirable reactions (see, for example, Greene and Wuts, supra, pages 224–276 (1991), which is incorporated herein by reference). The skilled artisan would recognize that such modifications as described above, which can be effected upon the N-terminus amino group or C-terminus carboxy group of a peptide, similarly can be effected upon any reactive amino group or carboxy group present, for example, on a side chain of an amino acid or amino acid analog in a peptide of the invention. Methods for performing such modifications are disclosed herein or otherwise known in the art.

The present invention provides compounds that specifically inhibit factor Xa activity. A compound of the invention has the general structure $X_1$-YIR-$X_2$ or a functional equivalent thereof, wherein $X_1$ is an H, acyl, alkyl, arylalkyl, or one or more amino acids, and $X_2$ is a modified C-terminal group, one or more carboxy-protecting groups, or one or more amino acids or other substituent such as an amino-protecting group. A compound of the invention is useful as an anticoagulant for therapeutic treatment of a variety of clinical conditions. A compound of the invention also is useful in a variety of laboratory procedures to prevent the clotting of blood samples.

The invention also provides a compound that specifically inhibits the activity of factor Xa, having the general formula A1-A2-(A3)$_m$—B, wherein m is 0 or 1 and A1 is $R_1$—$R_2$—$R_3$, A2 is $R_4$—$R_5$—$R_6$ and A3 is $R_7$—$R_8$—$R_9$; wherein $R_1$ is selected from the group consisting of 1 to 20 amino acids;

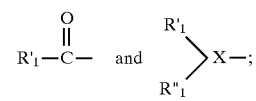

X is selected from the group consisting of N, CH and NC(O), and R'$_1$, and R"$_1$ independently are selected from the group consisting of H, alkyl, acyl, aryl, arylalkyl and an amino-protecting group and wherein $R_1$ can be substituted by a substituent; $R_2$ is —$CR_{99}R_{100}$—, wherein $R_{99}$ and $R_{100}$ independently are selected from the group consisting of an H; alkyl, arylalkyl, heteroarylalkyl and heteroaryl, and wherein $R_{99}$ and $R_{100}$ independently can be substituted with a substituent; $R_3$ is selected from the group consisting of —C(O)—, —CH$_2$—, —CHR$_{99}$—C(O)— and —C(O)—NR$_{35}$—CH$_2$—C(O)—, wherein $R_{35}$ is the CHR$_{55}$ group of the bridging group —C(O)—CR$_{55}$—; $R_4$ is selected from the group consisting of —CH$_2$— and —NR$_{50}$—, wherein R$_{50}$ is selected from the group consisting of H, alkyl, arylalkyl and heterocyclic; R$_5$ is >CR$_{201}$R$_{202}$, wherein R$_{201}$ and R$_{202}$ independently are selected from the group consisting of H, alkyl, aryl and arylalkyl, and wherein R$_{201}$ and R$_{202}$ independently can be substituted with a substituent; R$_6$ is selected from the group consisting of —C(O)—, —CH$_2$— and —CHR$_{99}$—C(O)—; R$_7$ is selected from the group consisting of —CH$_2$— and —NR$_{51}$—, wherein R$_{51}$ is H, alkyl, arylalkyl, heteroalkyl and heteroarylalkyl, and any of these moieties substituted by a substituent selected from the group consisting of Q and —(CH$_2$)$_n$—Q, wherein n is 1 to 5 and wherein Q is selected from the group consisting of an amino, amidino, imidazole and guanidino group, which can be substituted with a substituent, and a mono-, di-, tri- or tetra-alkylammonium of a pharmaceutically acceptable salt, isoureide or isothioureide thereof; R$_8$ is —CR$_{210}$R$_{211}$—, wherein R$_{210}$ and R$_{211}$ independently are selected from the group consisting of H, alkyl, alkylaryl and heterocyclic, and any of these moieties substituted by a substituent selected from the group consisting of Q and —(CH$_2$)$_n$—Q wherein n is 1 to 5 and wherein Q is selected from the group consisting of an amino, amidino, imidazole and guanidino group, which can be substituted with a substituent, and a mono-, di-, tri- or tetra-alkylammonium of a pharmaceutically acceptable salt, isoureide or isothioureide thereof; R$_9$ is selected from he group consisting of —C(O)—, —CH$_2$— and —CHR$_{99}$—C(O)—; and wherein, when m is 1, B is selected from the group consisting of 1 to 20 amino acids, —NHR$_{52}$, —NR$_{60}$R$_{61}$, —OR$_{70}$ and —CHR$_{60}$R$_{61}$, wherein R$_{52}$ is selected from the group consisting of H, alkyl, arylalkyl, heteroarylalkyl and heteroaryl; wherein R$_{60}$ and R$_{61}$ independently are selected from the group consisting of H, alkyl, arylalkyl, aryl, heteroarylalkyl and heteroaryl, and wherein R$_{70}$ is selected from the group consisting of H, acyl, alkyl, arylalkyl and heteroarylalkyl, and wherein when m is 0, B is selected from the group consisting of 1 to 20 amino acids, —OR$_{70}$, —NHR$_{52}$ and —NR$_{60}$R$_{61}$, which is joined to R$_6$ by an amide bond or an ester bond; wherein B can be substituted with a substituent, provided that when R$_3$ is —CH$_2$— or —CHR$_{99}$—C(O)—, R$_4$ is NR$_{50}$; when R$_4$ is —CH$_2$—, R$_3$ is —C(O)—or —CHR$_{99}$—C(O)—; when R$_4$ is —CH$_2$—, R$_3$ is —C(O)—or —CHR$_{99}$—C(O)—; when R$_6$ is —CH$_2$—, R$_7$ is —NHR$_{51}$—; when R$_7$ is CH$_2$, R$_6$ is —C(O)— or —CHR$_{99}$—C(O)—; when R$_4$ is —CR$_{50}$— and R$_1$ is

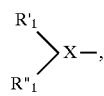

R$_{50}$ and R'$_1$ are taken together to form a bridging group having the formula: —C(O)—CHR$_{55}$—, wherein CHR$_{55}$ represents R$_{50}$ and the carbonyl group represents R'$_1$, and R"$_1$, and R$_{55}$ independently are H, C$_1$ to C$_6$ alkyl or arylalkyl; and when R$_3$ is —C(O)—NR$_{35}$—CH$_2$—C(O)—, then R$_4$ is —NR$_{50}$—, R$_1$ is

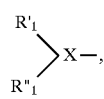

Figure 2:
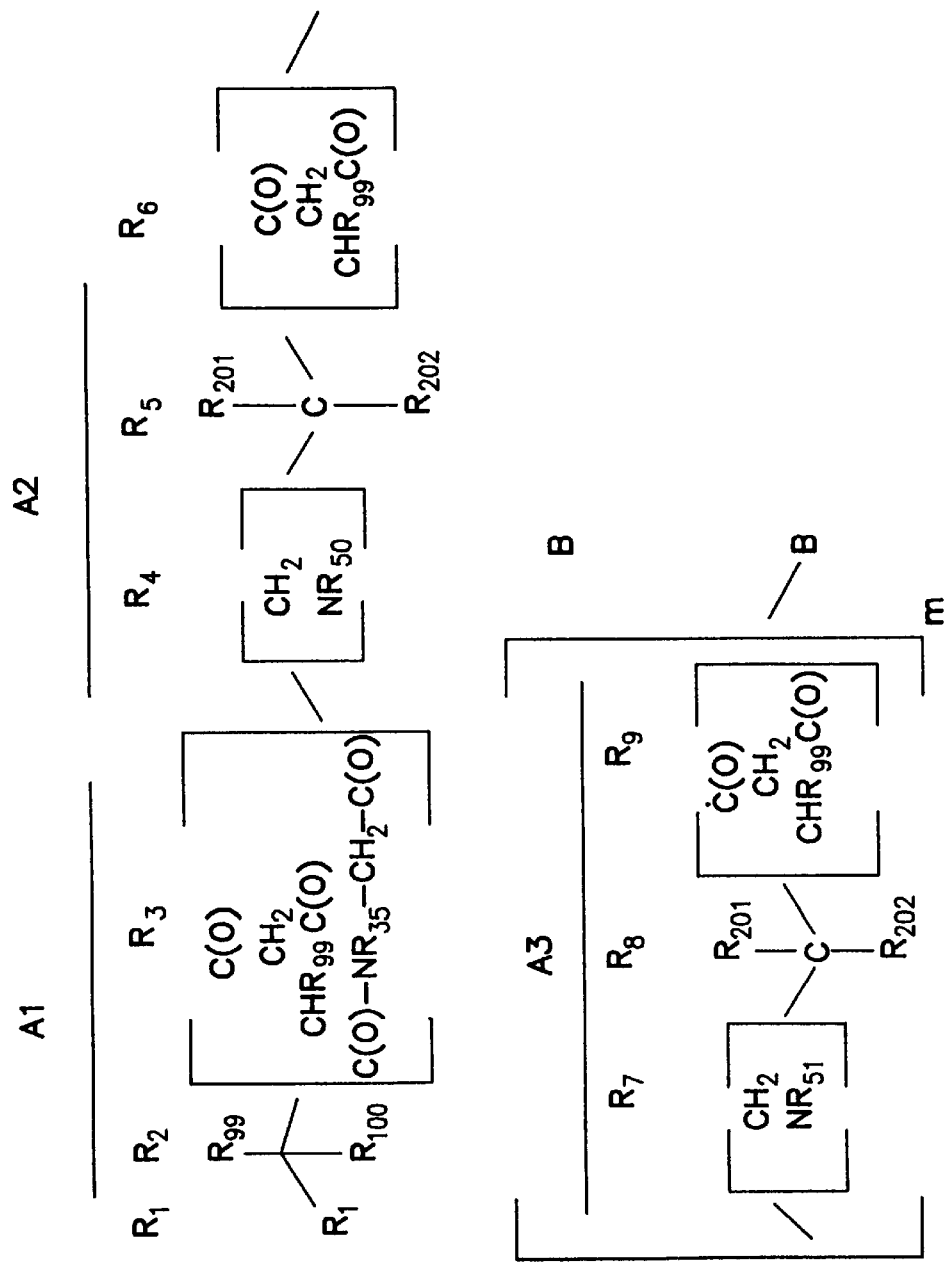
FIG. 2 exemplifies a structure for a compound of the invention.

R$_{35}$ and R'$_1$ are taken together to form a bridging group having the formula —C(O)CHR$_{55}$—, wherein C(O) represents R'$_1$ and CHR$_{55}$ represents R$_{35}$; R"$_1$ and R$_{55}$ independently are H or a C$_1$ to C$_6$ alkyl (see, for example, FIG. 2).

A commound of the invention can contain a cyclic N-terminus formed by R$_1$, R$_2$, R$_3$ and, if desired, R$_4$. Such a compound is defined, for example, by the structure A1-A2-(A3)$_m$—B, as described above, wherein R$_4$ is —NR$_{50}$—, R$_1$ is

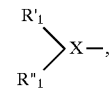

R$_{50}$ and R'$_1$ are taken together to form a bridging group of the formula —C(O)—CHR$_{55}$, wherein R$_{55}$ is H; R$_1$ is H or methyl; R$_{99}$ and R$_{100}$ independently are selected from the group consisting of H, arylalkyl, alkyl and heteroalkyl or 1 to 3 carbon atoms, and wherein R$_{99}$ and R$_{100}$ can be further linked to a moiety selected from the group consisting of phenyl, thienyl, thiazolyl, pyridyl, naphthyl, thionaphthyl, indolyl or saturated alkyl, alkoxy, monoalkylamino, dialkylamino, tetraalkylammonium, arylalkylamino, aminoalkylaryl, carboxy, halo, hydroxy, amino, amido, amidino, guanidino, triazolyl and sulfonyl, and R$_3$ is selected from the group consisting of —C(O)—and —C(O)—NR$_{35}$—CH$_2$—C(O)—.

Furthermore, in the compound A1-A2-(A3)$_m$—B, the R'1 and R"1 moieties can be substituted with up to six substituents, including, for example, an alkyl, and optionally linked by a group such as —OCH$_2$—, —SCH$_2$—, >N—CH$_2$—, >NC(O)—, —CO— or —NY—CO—NZ, where Y and Z can be H, alkyl, arylalkyl or heteroarakyl. Moreover, R$_{99}$ and R$_{100}$ independently can be substituted by a substituent such as a phenyl, thienyl, thiazolyl, pyridyl, naphthyl, thionaphthyl or indolyl group, or a saturated group corresponding thereto, optionally substituted by up to five groups selected from alkyl, alkoxy, mono-, di- or tri-alkylamine, tetralkylammonium, arylalkylamino, aminoalkylaryl, carboxy, halogens, hydroxy, amino, amide, amidino, guanidino, triazolyl or sulfonyl. A preferred compound with substitutions at the R$_2$ position is where R$_{100}$ is an H and R$_{99}$ is either

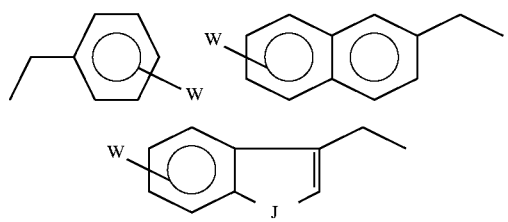

where W in the substituted compound can be, for example, a halogen, hydroxyl, amino or amidino group, and J can be, for example, an O, S or —NR, where R is an H or an alkyl, aryl or arylalkyl.

A compound of the invention, which contains a substituent substituted on the A2 moiety and exhibits factor Xa inhibitory activity, can have, for example, the substitution of R$_{50}$, R$_{201}$ or R$_{202}$ with one or more heteroatom substituents such as an N, O or S. R$_{202}$ also can be substituted with a substituent selected from

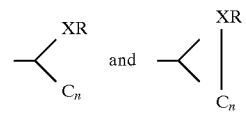

Where X is a C, N or S; R is absent, H or alkyl, which can be substituted with a heteroatom, and n is 1 to 5.

A compound of the invention, which contains a substituent substituted on the A3 moiety and exhibits factor Xa inhibitory activity, can include, for example, the substitution of $R_{51}$ with one or more substituents such as an H, alkyl, arylalkyl or heterocyclic, optionally substituted with a heteroatom such as an N, O or S. $R_{210}$ and $R_{211}$ can be, for example, the substituent —$(CH_2)_n$—Q, where n is about 1 to 5 and where Q is an amino, amidino, urea, imidazole, guanidino, mono-, di-, tri- or tetra-alkyl imminium of a pharmaceutically acceptable salt, isoureide or isothioureide. Alternatively, $R_{210}$ or $R_{211}$ can be, for example, an alkyl, aryl or alkylaryl. These groups can be further substituted with a substituent such as a hydroxy or $C_1$ to $C_4$ alkoxy group.

A compound of the invention can contain an alternative arrangement of substituents comprising the B moiety. Such an alternative arrangement of substituents can include, for example, the substitution of $R_{52}$ by an N, O or S or the substitution of $R_{60}$, $R_{61}$ or $R_{70}$ by one or more heteroatoms or alkyl groups.

The general structures disclosed herein represent the various compounds of the invention, which retain factor Xa inhibitory activity such as imparted by the tripeptide, YIR. Also represented within the structures disclosed herein are compounds containing non-naturally occurring amino acids, amino acid mimetics and other organic structures and substituents exhibiting similar function. Such functional equivalents provide the appropriate spatial groupings of the desired charges and forces that confer effective factor Xa inhibitor function.

Specific examples of the compounds of the invention include, for example, Ac-Tyr-Ile-Arg-Leu-Ala—$NH_2$; Ac-Tyr-Ile-Arg-Leu-Pro—$NH_2$; Ac-(iBu)Tyr-Ile-Arg-Leu-Pro—$NH_2$; Ac-Tyr-Ile-Arg—$N(CH_3)O(CH_3)$; Ac-Tyr-{Ψ($CH_2NH$)}-Ile-Arg-Leu-Pro—$NH_2$; Ac-Tyr-Ile-Arg—NH—$CH_2$(4-Pyridyl); Ac-Tyr-Ile-{Ψ($CH_2NH$)}-Arg-Leu-Pro—$NH_2$; Ac-Tyr-Chg-Arg($NO_2$)-{Ψ($CH_2NH$)}-Leu—$NH_2$; Ac-Tyr-Ile-Arg-{Ψ($COCH_2$)}-Gly-Pro—$NH_2$; Ac-Tyr-Ile-Dab($N^γ$—$C_3H_7N$)-Leu-Ala—$NH_2$; Ac-Tyr-Ile-PalMe(3)—$NH_2$; Tyr-Ile-Arg—$NH_2$; D-Tyr-Ile-Arg-Leu-Pro—$NH_2$, Ac-(Bzl) Gly-(Chx)Gly-(3-guanidopropyl) Gly—$NH_2$; Cyclo(Gly-Tyr-Ile-Arg-Gly); Tfa-(iBu) Tyr-Chg-Arg-Leu-Pro—$NH_2$; Ac-pAph-Chg-Arg-Leu-Pro—$NH_2$; and Ac-Nal(2)-Chg-Arg-Leu-Pro—$NH_2$. Additional YIR peptides of the invention are shown, for example, in Tables 3 and 5.

The present invention also provides a compound having the structure A1-A2-(A3)$_m$—B, wherein $R_1$ is

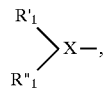

$R'_1$ is selected from the group consisting of H, —CO—$R_a$, —$SO_2$—$R_a$, an amino-protecting group, 1 to 6 amino acids, which can be substituted, wherein the N-terminus of said 1 to 6 amino acids is substituted with a substituent selected from the group consisting of H, —CO—$R_a$, —$SO_2$—$R_a$ and an amino-protecting group; and wherein $R_a$ is selected from the group consisting of alkyl, aryl and heteroalkyl; $R''_1$ is selected from the group consisting of H, acyl and alkyl; X is N; $R_2$ is —$CHR_{99}$—, wherein $R_{99}$ is selected from the group consisting of alkyl, aryl, arylalkyl, heteroalkyl and heteroaryl, which can be substituted with a substituent selected from the group consisting of 1 to 6 fluoro, chloro, bromo, iodo, amino, nitro, amidino, amido, carboxy, ester, ether and hydroxy groups; $R_3$ is —C(O)—; $R_4$ is —NH—; $R_5$ is —$CHR_{201}$—, wherein $R_{201}$ is an alkyl; $R_6$ is —C(O)—; $R_7$ is —NH—; $R_8$ is —$CHR_{210}$—, wherein $R_{210}$ is a heteroalkyl having at least one formal positive charge, wherein the heteroatom is 1 to 6 nitrogen atoms; $R_9$ is —C(O)—; and B is selected from the group consisting of —$OR_b$ and —N—$R_cR_d$, wherein $R_b$ is selected from the group consisting of H, alkyl and a carboxy-protecting group, $R_c$ is selected from the group consisting of H and alkyl, and $R_d$ is selected from the group consisting of alkyl, heteroalkyl and 1 to 20 amino acids, which can be substituted with a substituent, wherein the C-terminus of said compound can be modified with a carboxy-protecting group, a primary amide group or part of a cyclic peptide as the secondary or tertiary amide group formed with amino group of $R_1$. Such a compound can contain one or more amino-protecting groups For example, a compound of the invention have $A_1$ selected from the group consisting of Tyr, F(pNH$_2$), mAph, pAph and Nal(2), which contain 0 or 1 amino-protecting groups; A2 selected from the group consisting of Ile and Chg; A3 selected from the group consisting of Arg, PalMe (3), Dab($N^γ$—$C_3H_7N$), Dap($N^β$—$C_3H_7N$) and Orn($N^δ$—$C_3H_7N$); and B selected from the group consisting of —H, —OH, —$NH_2$, one to five amino acids or functional equivalents thereof and a carboxy-protecting group. Examples of such compounds include Ac-pAph-Chg-PalMe(3)—NH—$CH_2$—Chx; Ac-pAph-Chg-PalMe(3)—NH-Chx; Bzf-pAph-Chg-PalMe(3)—$NH_2$; Ac-pAph-Chg-PalMe(3)-L-P—$NH_2$; Ac-pAph-Chg-PalMe(3)—$NH_2$; Cyclopentyl-CO-pAph-Chg-PalMe(3)—$NH_2$; 3-Iqc-pAph-Chg-PalMe(3)—$NH_2$; 2-Furoyl-pAph-Chg-PalMe(3)—$NH_2$; 5-Me-thienyl-CO-pAph-Chg-PalMe(3)—$NH_2$; and Ac-pAph-Chg-PalMe(3)-ol (see, also, Table 5).

The invention further provides a compound having the structure A1-A2-B, i.e., A1-A2-(A3)$_m$—B, wherein m is 0. In such a compound, B can be a heteroarylalkyl such as (4-(N-methyl pyridinium))methyl; 2-(3-(N-methylpyridinium))eth-1-yl; 1-(4—(N-methylpyridinium))eth-1-yl; (p-amidino)benzyl; 2-(4-(N-methylpyridinium))prop-2-yl; and 2-(4-(N-methylpyridinium))eth-1-yl. Ac-pAph-Chg-AMP(4) and Ac-pAph-Chg-AEMP(4) are examples of such compounds.

The choice of including an L- or a D-amino acid in a compound of the present invention can depend, in part, on the desired characteristics of the peptide. For example, the incorporation of one or more D-amino acids can confer increased stability on the compound in vitro or in vivo. The incorporation of one or more D-amino acids also can increase or decrease the pharmacological activity of the compound. In some cases it can be desirable to allow the compound to remain active for only a short period of time. In such cases, the incorporation of one or more L-amino acids in the compound can allow endogenous peptidases in an individual to digest the compound in vivo, thereby limiting the individual's exposure to the active compound. The skilled artisan can determine the desirable characteristics required of compound of the invention by taking into consideration, for example, the age and general health of an individual.

A compound of the invention can be chemically synthesized using, for example, an automated synthesizer (see Example I). Selective modification of a reactive group such as a group present on an amino acid side chain or an N-terminus or a C-terminus reactive group in a peptide can impart desirable characteristics such as increased solubility or enhanced inhibitory function to a compound of the invention.

Where solid phase synthesis methods are employed, the chemical composition of a compound can be manipulated while the nascent peptide is attached to the resin or after the peptide has been cleaved from the resin to obtain, for example, an N-terminal derivative such as an N-terminus acetylated compound. Similar modifications also can be made to a carboxy group of a compound, including a C-terminus carboxy group, which, for example, can be amidated. One skilled in the art also can synthesize a YIR peptide of the invention using solution phase organic chemistry. A synthesized compound can be purified using well known methods such as reverse phase-high performance liquid chromatography (RP—HPLC; see Example I) or other methods of separation based, for example, on the size, charge or hydrophobicity of the compound. Similarly, well known methods such as amino acid sequence analysis or mass spectrometry (MS) can be used for characterizing the structure of a compound of the invention (see Example I).

The YIR peptides of the invention can be linear or cyclic (see, for example, Table 3, below). Cyclization can be accomplished by forming a bridge between two nonadjacent residues, moieties or substituents, which can be within or outside of the YIR motif. Cyclization also can be accomplished, for example, by forming a bridge between one of the residues within the YIR motif and a nonadjacent residue, moiety or substituent outside the YIR sequence. For example, peptides or peptidomimetics can by cyclized via S-S, —$CH_2$—S—, —$CH_2$—O—$CH_2$—, lactam or ester linkages or as previously reported (see Hruby, *Life Sci.* 31:189–199 (1982); Toniolo, Int. *J. Pept. Prot. Res.* 35:287–300 (1990); Kates et al., *Tetr. Lett.* 34:1549–1552 (1993), each of which is incorporated herein by reference).

As used herein, the phrase "outside the YIR motif" means not including a tyrosine, isoleucine or arginine residue of the YIR sequence or its equivalent present in a YIR peptide of the invention. In contrast, the phrase "within the YIR motif" means including at least one of the tyrosine, isoleucine and arginine residues of the YIR sequence or its equivalent. The term "bridge" in referring to a cyclic compound means a bond formed between two non-adjacent amino acids present in a YIR peptide of the invention.

Cyclization can be achieved by the formation, for example, of a disulfide bond or a lactam bond between $X_1$ and $X_2$. Residues capable of forming a disulfide bond include, for example, Cys, Pen, Mpr, and Mpp and its 2-amino group-containing equivalents. Residues capable of forming a lactacm bridge include, for example, Asp, Glu, Lys, Orn, α,β-diaminopropionic acid, α-amino-adipic acid, α,γ-diaminobutyric acid, diaminoacetic acid, aminobenzoic acid and mercaptobenzoic acid. The compounds disclosed herein can be cyclized, for example, via a lactam bond, which can utilize a side chain group of one non-adjacent residue to form a covalent attachment to the N-terminus amino group of $X_1$ or of Y. Alternative bridge structures also can be used to cyclize the compounds of the invention, including, for example, peptides and peptidomimetics, which can be cyclized via S-S, —$CH_2$—S—,—$CH_2$—O—$CH_2$—, lactam, ester or other linkages (see for example, Hruby, supra, 1982; Toniolo, supra, 1990; Kates et al., supra, 1993).

A composition of the present invention can be provided as a homogenous composition or as a mixture of compounds containing various combinations of substituents. The flexibility permitted by the choice of substituents permits a great deal of control over the physico-chemical properties of the peptide compound analogs. The choice of the substituent also influences the binding affinity of the compound (see Examples).

Various compounds containing different arrangements of the substituents exhibit different levels of inhibitory activity for factor Xa. These compounds were synthesized according to the procedures described in the Examples. Testing the peptides for inhibitory activity was accomplished using the assays described in Examples XXXVII and XXXVIII. Using such methods, one skilled in the art can synthesize a compound as disclosed herein, including a modification thereof, and determine the factor Xa inhibitory activity of the compound.

The invention provides compounds that specifically inhibit factor Xa activity. Such compounds have a $K_i \leq 100$ μM, preferably $\leq 2$ nM, for factor Xa activity and do not substantially inhibit the activity of other proteases involved in coagulation and fibrinolysis relative to the inhibition of factor Xa (see Table 2, above). Such other proteases include, for example, thrombin and plasmin. Specificity of the compounds of the invention is demonstrated in Example XXXVII, below (see, also, Table 2, above).

A compound of the invention can be used advantageously as an anticoagulant, which can be contacted with a blood sample to prevent coagulation. For example, an effective amount of a compound of the invention can be contacted with a freshly drawn blood sample to prevent coagulation of the blood sample. As used herein, the term "effective amount" when used in reference to a compound of the invention means an amount of a compound that inhibits factor Xa activity. The skilled artisan would recognize that an effective amount of a compound of the invention can be determined using the methods disclosed herein (see Examples XXXVII and XXXVIII) or otherwise known in the art. In view of the disclosed utility of a compound of the invention, the skilled artisan also would recognize that an agent such as heparin can be replaced with a compound of the invention. Such a use of a compound of the invention can result, for example, in a cost saving as compared to other anticoagulants.

In addition, a compound of the invention can be administered to an individual for the treatment of a variety of clinical conditions, including, for example, the treatment of a cardiovascular disorder or a complication associated, for example, with infection or surgery. Examples of cardiovascular disorders include restenosis following angioplasty, adult respiratory distress syndrome, multi-organ failure, stroke and disseminated intravascular coagulation clotting disorder. Examples of related complications associated with surgery include, for example, deep vein and proximal vein thrombosis, which can occur following surgery. Thus, a compound of the invention is useful as a medicament for reducing or inhibiting unwanted coagulation in an individual.

Since a YIR peptide of the invention can inhibit factor Xa activity, such a compound can be useful for reducing or inhibiting blood clotting in an individual. As used herein, the term "individual" means a vertebrate, including a mammal such as a human, in which factor Xa is involved in the clotting cascade.

Blood clotting in an individual can be reduced or inhibited by administering to the individual a therapeutically effective amount of a YIR peptide of the invention. As used herein, the term "therapeutically effective amount" means the dose of a YIR peptide that must be administered to an individual in order to inhibit factor Xa activity in the individual. More specifically, a therapeutically effective amount of a compound of the invention inhibits factor Xa catalytic activity either directly, within the prothrombinase complex or as a soluble subunit, or indirectly, by inhibiting the assembly of factor Xa into the prothrombinase complex. In particular, such compounds can inhibit factor Xa activity with a $K_i \leq 100$ μM and, preferably, with a $K_i \leq 2$ nM. A therapeutically effective amount can be determined using the methods described, for example, in Examples XXXVII and XXXVIII or otherwise known in the art.

In the practice of a therapeutic method of the invention, the particular dosage to obtain a therapeutically effective amount of a pharmaceutical composition to be administered to the individual will depend on a variety of considerations, including, for example, the nature or severity of the disease, the schedule of administration and the age and physical characteristics of the individual. An appropriate dosage can be established using clinical approaches well known in the medical art. Thus, the invention provides a method of specifically inhibiting factor Xa activity by contacting factor Xa with a compound having the sequence $X_1$-YIR-$X_2$ or A1-A2-(A3)$_m$—B, where m is 0 or 1, or a functional equivalent thereof. The invention further provides a method of reducing or inhibiting the formation of a blood clot in an individual by administering a therapeutically effective amount of a compound of the invention.

A compound of the invention generally will be administered to an individual as a composition containing the compound and a pharmaceutically acceptable carrier. The term "pharmaceutically acceptable carrier" refers to a medium or composition that is non-toxic to an individual or has acceptable toxicity as determined by the appropriate regulatory agency. As used herein, the term pharmaceutically acceptable carrier encompasses any of the standard pharmaceutical carriers such as phosphate buffered saline, water, an emulsion such as an oil/water or water/oil emulsion, or any of various types of wetting agents. Suitable pharmaceutical carriers and their formulations are described by Martin (in Remington's Pharmaceutical Sciences, 15th Ed. (Mack Publishing Co., Easton 1975) which is incorporated herein by reference). Such compositions will, in general, contain a therapeutically effective amount of a compound of the invention together with a suitable amount of carrier so as to comprise the proper dosage for administration to an individual. Thus, the claimed compounds can be useful as medicaments for inhibiting factor Xa activity and blood clotting in an individual.

Pharmaceutically acceptable carriers also can include, for example, other mediums, compounds or modifications to a factor Xa inhibitor compound that enhances its pharmacological function. A pharmaceutically acceptable medium can include, for example, an acid addition salt such as a salt formed with an inorganic acid such as hydrochloric acid, hydrobromic acid, phosphoric acid, sulfuric acid or perchloric acid, or with an organic acid such as acetic acid, oxalic acid, maleic acid, malic acid, tartaric acid, citric acid, succinic acid or malonic acid. Other pharmaceutically acceptable salts include, for example, inorganic nitrate, sulfate, acetate, malate, formate, lactate, tartrate, succinate, citrate, p-toluenesulfonate, and the like, including, but not limited to, cations based on the alkali and alkaline earth metals such as sodium, lithium, potassium, calcium or magnesium, as well as non-toxic ammonium, quaternary ammonium and amine cations such as ammonium, methylammonium, dimethylammonium, trimethylammonium, tetramethylammonium, ethylammonium, triethylammonium and tetraethylammonium.

Examples of modifications that enhance the pharmacological function of the compound include, for example, esterification such as the formation of $C_1$ to $C_6$ alkyl esters, preferably $C_1$ to $C_4$ alkyl esters, wherein the alkyl group is a straight or branched chain. Other acceptable esters include, for example, $C_5$ to $C_7$ cycloalkyl esters and arylalkyl esters such as benzyl esters. Such esters can be prepared from the compounds described herein using conventional methods well known in the art of peptide chemistry.

Pharmaceutically acceptable modifications also can include, for example, the formation of peptide amides. Such amide modifications, which can be effected upon the compounds of the invention, include, for example, those derived from ammonia, primary $C_1$ to $C_6$ dialkyl amines, where the alkyl groups are straight or branched chain, or arylamines having various substitutions. In the case of secondary amines, the amine also can be in the form of a 5 or 6 membered heterocycle containing, for example, a nitrogen atom. Methods for preparing such amides are well known in the art.

In another embodiment of the invention, a YIR peptide can be used in an assay to identify the presence of factor Xa or to isolate factor Xa in a substantially purified form. Preferably, the compound of the invention is labeled with, for example, a radioisotope, and the labeled compound is detected using a routine method useful for detecting the particular label. In addition, a YIR peptide can be used advantageously as a probe to detect the location or amount of factor Xa activity in vivo, in vitro or ex vivo.

It is understood that modifications that do not substantially affect the activity of the various embodiments of this invention are included within the invention disclosed herein. Accordingly, the following examples are intended to illustrate but not limit the present invention.

EXAMPLE I

Peptide Synthesis Procedures

Starting materials used in the synthesis were obtained from chemical vendors such as Aldrich, Sigma, Fluka, Nova Biochem and Advance Chemtech. During the synthesis of these compounds, the functional groups of the amino acid derivatives used in these methods were protected by blocking groups to prevent side reaction during the coupling steps. Examples of suitable protecting groups and their use are described in *The Pentides*, supra, 1981, and in Vol. 9, Udenfriend and Meienhofer ed. 1987, which is incorporated herein by reference.

General solid-phase peptide synthesis was used to produce the compounds of the invention. Such methods are described, for example, by Steward and Young (*Solid Phase Peptide Synthesis* (Freeman and Co., San Francisco, 1969), which is incorporated herein by reference).

Unless indicated otherwise, peptides were synthesized on polystyrene resin cross-linked with 1% divinylbenzene. An acid sensitive linker (Rink Linker) was coupled to the solid support (Rink, *Tetr. Lett.* 28:3787 (1987); Sieber, *Tetr. Lett.* 28:2107 (1987), each of which is incorporated herein by reference). Coupling was performed using N,N'-diisopropylcarbodiimide (DIC) in the presence of an equivalent amount of HOBt. All couplings were done in either N,N-dimethylformamide (DMF) or DMF:dichloromethane (1:1 mixture) at room temperature (RT) for 40 min. Completion of coupling was monitored by ninhydrin test.

Deprotection of the Fmoc group was accomplished using 50% piperidine in DMF for 10 min. The amount of Fmoc released was determined from the absorbance at 300 nm of the solution after deprotection, volume of washes and weight of the resin used in the synthesis. A second (double) coupling was performed where coupling in the first instance was incomplete. The cycle of each coupling and methods was as follows:

| Step | Action | Reagent and Solvent |
|------|--------|---------------------|
| 1 | 1 g Peptide Resin | 10 ml DMF |
| 2. | 2.4 fold-excess amino acid derivative | |
| 3. | 2.4 equivalent | DIC |
| 4. | 2.4 equivaient | HOBt |
| 5. | Couple for 40 min | |
| 6. | Wash (3 × 8 ml) | DMF |
| 7. | Ninhydrin test | |
| 8. | Deprotection (10 min) | 8 ml 50% Piperidine/DMF |
| 9. | Wash (6 × 8 ml) | DMF |
| 10. | Wash (2 × 8 ml) | Dichloromethane (DCM) |
| 11. | Ninhydrin test | |
| 12. | Repeat starting at step 2. | |

After completion of peptide assembly on the resin, the final Fmoc deprotection was performed, then followed by normal wash cycles and determination the amount of Fmoc group released by deprotection. In some cases, the $N^\alpha$-unprotected peptide was acetylated by shaking the peptide resin with 20-fold excess of acetic anhydride/pyridine (1:1) in DCM for 15 min. The peptide resin was washed successively with DCM, DMF and DCM, then dried under vacuum.

Peptide resin was suspended in reagent K (King et al., *Int. J. Pept. Prot. Res.* 36:255–266 (1990), which is incorporated herein by reference) cocktail (5 ml/g peptide resin) for 180 min at RT, then the cleavage mixture was filtered in anhydrous diethyl ether and the solid precipitate was isolated by centrifugation and dried in vacuum over solid pellets of KOH. The dried peptide was subjected to HPLC purification using an appropriate gradient of 0.1% TFA in water and acetonitrile (ACN). After collecting the peak containing the intended synthetic product, the peptide solution was lyophilized and the peptide was subjected to an identification process, which included electrospray MS and amino acid analysis to confirm that the correct compound was synthesized.

For peptide purification, a sample of crude lyophilized peptide was dissolved in a mixture of 0.1% aqueous TFA containing 10% to 50% ACN. The peptide solution usually was filtered through a syringe connected to a 0.45 μm nylon "ACRODISC" 13 (Gelman Sciences; Ann Arbor MI) filter. A proper volume of filtered peptide solution was injected into a semi-preparative C18 column (Vydac Protein and Peptide C18, 218TP1010; The Separation Group; Hesperia Calif.). The flow rate of a gradient or isocratic mixture of 0.1% TFA buffer and ACN (HPLC grade) as an eluent was maintained using a Beckman "SYSTEM GOLD" HPLC. Elution of the peptide was monitored by UV detection at 230 nm (Beckman, System Gold, Programmable Solvent Module 126 and Programmable Detector Module 166 controlled by "SYSTEM GOLD" software). After identifying the peak corresponding to the compound under synthesis, using MS, the compound was collected, lyophilized and biologically tested. MS was performed using a SCIEX API III+ instrument. In addition, NMR was performed using a General Electric instrument (300 MHz). For NMR, samples typically were measured in hexadeuterodimethylsulfoxide or deuterochloroform (CDCl$_3$; Aldrich).

Amino acid aldehydes were prepared using methods well known in the art. Amino acids and peptide aldehydes have been reported, for example, by Fehrentz and Castro, *Synthesis* 676 (1983); Bajusz et al., *J. Med. Chem.* 33:1729 (1990); Kawamura et al., *Chem. Pharm. Bull.* 17:1902 (1969), and Someno et al., *Chem. Pharm. Bull.*, 34:1748 (1986), each of which is incorporated herein by reference. Synthesis of reduced peptide bonds was performed at the level of the dipeptide in solution (e.g., Tyr-{Ψ(CH$_2$NH)}-Ile), then the properly protected dipeptide was coupled to the rest of the peptide on resin using solid phase peptide synthesis. Alternatively, the protected amino acid aldehyde was coupled to the peptide on resin using methods described by Ho et al. (*Pept. Res.* 6:10–12 (1993), and references cited therein, each of which is incorporated herein by reference).

EXAMPLE II

Synthesis of Ac-Tyr-Ile-Arg-Leu-Ala—NH$_2$

For the synthesis of Ac-Tyr-ile-Arg-Leu-Ala—NH$_2$, 1 g of Rink resin (0.6 mmol NH$_2$/g resin) was used in the procedure as described above. The resultant peptide was analyzed by MS. (M+H)$^+$ found 659.4, calculated (calc.) 659.9.

EXAMPLE III

Synthesis of Ac-Tyr-Ile-Arg-Leu-Pro—NH$_2$

For the synthesis of Ac-Tyr-Ile-Arg-Leu-Pro—NH$_2$, 1 g of Rink resin (0.6 mmol NH$_2$/g resin) was used in the procedure as described in Example I. The resultant peptide had an (M+H)$^+$ found 685.4, calc. 685.9.

EXAMPLE IV

Synthesis of Ac-(iBu)Tyr-Ile-Arg-Leu-Pro—NH$_2$ 1 g of Rink resin (0.6 mmol NH$_2$/g resin) was used. The general solid phase synthesis outlined above was used. After deprotection of Tyr and proper washing of the peptide resin, 50 eq isobutyraldehyde in DMF containing 2% glacial acetic acid was added. The resulting mixture was shaken for 4 hr at RT. After washing the peptide resin with DMF containing 2% acetic acid (2×8 ml), 1 g of NaBH$_3$CN in 10 ml of DMF containing 2% acetic acid was added. The peptide resin was shaken for 30 min, then the peptide resin was filtered and a fresh mixture of NaBH$_3$CN in DMF/acetic acid was added and the reaction continued for an additional 30 min.

The peptide resin then was washed with DMF/2% acetic acid (2×8 ml) and DMF (2×8 ml). The resultant monoalkylated peptide resin was acetylated with acetic anhydride triethylamine mixture in DMF (30 eq, 6 h). After proper washing of the peptide resin, the peptide was cleaved and deprotected as described in Example I. HPLC purified peptide was analyzed by MS. (M+H)$^+$ found 758.4, calc. 758.5.

EXAMPLE V

Synthesis of Tfa-(iBu)Tyr-Ile-Arg-Leu-Pro—NH$_2$
(SEQ ID NO:16)

The same protocol as described in Example IV was used to prepare (iBu)Tyr-Ile-Arg-Leu-Pro-Rink resin (SEQ ID NO:17). Final trifluoroacetylation was performed by treating the peptide-resin with 0.7M trifluoroacetanhydride in the presence of Diisopropylethylamine (DIEA) and N-methyl imidazole (NMI) (1:3:0.3 eq) for 45 min. Cleavage of the peptide from the resin and isolation of the peptide were performed as described in Example IV. The purified peptide was identified by MS. (M+H)$^+$ found 812.4, calc. 812.5.

EXAMPLE VI

Synthesis of Ac-Tyr-Ile-Arg—N(CH$_3$)O(CH$_3$)

The synthesis of Boc-Arg(N$^G$-Tos)—N(CH$_3$)O(CH$_3$) was accomplished according to the literature procedure (Fehrentz and Castro, supra, 1983). Boc-Arg(N$^\gamma$-Tos)—N(CH$_3$)O(CH$_3$) (200 mg) was mixed with 5 ml trifluoroacetic acid (TFA) at RT and stirred for 20 min. Disappearance of the starting material was monitored by thin layer chromatography (TLC) using CHCl$_3$:MeOH:CH$_3$COOH (90:9:1) and visualized by ninhydrin spray and UV illumination. Evaporation of the remaining TFA under vacuum and drying in vacuum over KOH pellets resulted in a solid material having the proper mass. (M+H)$^+$ found 371.2, calc. 371.4.

In one flask, 150 mg of the material prepared above was dissolved in 1 ml DMF, then 57 μl triethylamine was added and the mixture was cooled to 0° C. In a second flask, 171 mg of Z-Tyr-Ile-OH (Biochem Bioscience Inc.; Philadelphia Pa.) was dissolved in anhydrous tetrahydrofuran (THF) and cooled to −10° C., then 44 μl NNM and 52 μl isobutylchloroformate was added under N$_2$ and the mixture was stirred for 15 min. A solution of Arg(Tos)N(CH$_3$)OCH$_3$ in DMF previously prepared was added to the mixed anhydride of Z-Tyr-Ile—OH dipeptide and the mixture was stirred at −10° C. for 30 min, then overnight at RT.

After workup of the reaction mixture as described in Example I, the peptide was dried under vacuum and a small portion was purified by HPLC and analyzed by MS; the peptide had the expected molecular weight (781). The resulting peptide Z-Tyr-Ile-Arg(Tos)—N(CH$_3$)OCH$_3$ was mixed with 500 μl anisole and subjected to HF deprotection by the usual procedure. After workup, 169 mg of the product Tyr-Ile-Arg—N(CH$_3$)O(CH$_3$) was isolated and identified by MS (found 493.6, calc. 494). The residual peptide then was dissolved in 1 ml of the 1N HCl and lyophilized.

Tyr-Ile-Arg—N(CH$_3$)OCH$_3$·2HCl (76 mg)was dissolved in ACN, cooled to 0° C. and 13 μl pyridine was added, followed by 15 μl acetic anhydride. The mixture was stirred at 0° C. for 3 hr and completion of the reaction was monitored by the ninhydrin test. After stirring at RT for 8 hr, the reaction mixture was worked up and the product, Ac-Tyr-Ile-Arg—N(CH$_3$)OCH$_3$, was characterized by MS (found 535.6, calc. 535.3).

EXAMPLE VII

Synthesis of Ac-Tyr-{Ψ(CH$_2$NH)}Ψ-Ile-Arg-Leu-Pro—NH$_2$ a. Synthesis of Fmoc-Tyr(But)—H 4.6 g (10.0 mmol) Fmoc-Tyr(But)—OH, 2.1 g (10.1 mmol) dicylohexylcarbodilmide (DCC), 1.26 g (10.1 mmol) benzylmercaptan and 0.12 g DMAP were reacted in DCM as described by Ho and Ngu (*J. Org. Chem.* 58:2315 (1993), which is incorporated herein by reference). After workup, Fmoc-Tyr(But)—S—CH$_2$C$_6$H$_5$ was isolated and, upon reduction of the thioester by stirring with triethylsilane in the presence of 10% Pd on carbon and purification by flash chromatography, gave a 81% yield of Fmoc-Tyr(But)-H. The NMR and mass of the product were in accordance with the expected range.

b. Synthesis of Fmoc-Tyr(But)-{Ψ(CH$_2$NH)}-Ile-(O-Allyl)

0.73 g (1.66 mmol) Fmoc-Tyr(But)—OH and 0.209 g (3.32 mmol) NaBH$_3$CN in 20 ml of 1% AcOH in DMF were added to a solution of 0.516 g (1.82 mmol) TFA.Ile-(O-Allyl) in 2 ml of DMF. After 2 hr, the reaction mixture was worked up and the final product purified by flash chromatography (ethyl acetate:hexane, 35:65) to give an oil product having the proper NMR and MS. (M+H) found 599, calc. 598.7.

c. Synthesis of Fmoc-Tyr(But)-{Ψ(CH$_2$NH)}-Ile—OH

To 0.467 g (0.78 mmol) Fmoc-Tyr(But)-{Ψ(CH$_2$NH)}-Ile-OAllyl in 10 ml DCM, was added 89 μl (1.56 mmol) HOAC, 20 μl triethylamine (TEA) and 0.02 g of complex PdCl$_2$(Ph$_3$)$_2$. 231 μl (0.86 nmol) Bu$_3$SnH was added in one portion and the mixture was stirred for 1 hr at RT. After proper workup of the reaction mixture, the product was purified on flash chromatography (CHCl$_3$:MeOH, 20:1) to give a 69% yield (0.319 g) of the expected peptide. (M+H$^+$) found 559, calc. 558. Fmoc-Tyr(But)-{Ψ(CH$_2$NH)}-Ile—OH then was coupled to Arg(Pmc)-Leu-Pro-Rink resin using general solid phase methodology as outlined in Example I. The finished peptide resin Ac-Tyr(But)-{Ψ(CH$_2$NH)}-Ile-Arg(Pmc)-Leu-Pro-Rink was deprotected and cleaved as usual as described in Example I and purified by HPLC on C18 column.

EXAMPLE VIII

Synthesis of Ac-Tyr-Ile-Arg—NH—CH$_2$(4-Pyridyl)

Oxime resin (DeGrado and Kaiser, *J. Org. Chem.* 45:1295 (1980) (0.862 g of 0.6 mmol/g) was coupled overnight with Boc-Arg(Tos)—OH in the presence of DIC/HOBt. The resin was washed with DMF, then DCM and acetylated with acetic anhydride/DIEA (1:1 eq) hn DCM. After washing the resin with DCM, DMF and DCM, it was deprotected with 25% TFA in DCM for 30 min. The deprotected resin was washed with DCM, isopropanol and DCM. To TFA.Arg (Tos)-OxmR was coupled Boc-Ile—OH in symmetrical anhydride form (3 eq) in the presence 1.5 eq DIEA in DCM. The cycle of washing, acetylation and deprotection, as described above, was repeated. After deprotection, Boc-Tyr (2-BrZ)—OH was coupled in a similar way as Ile, then the finished peptide resin Boc-Tyr(2-BrZ)-Ile-Arg(Tos)-OxmR was deprotected and acetylated to give Ac-Tyr(2-BrZ)-Ile-Arg(Tos)-OxmR. The peptide resin was dried under vacuum to give a total gain of 0.216 g.

To ⅓ of the resin was added 100 μl (800 μmol) 4—(dimethylamino)pyridine in the presence of 60 μl glacial acetic acid and 120 μl DIEA in 6 ml of DCM. The resin was shaken overnight at RT. After filtration of the DCM solution, the resin was washed with 3 μl DMF and the washes were combined with the DCM filtrate. After evaporation of the solvent, the residual peptide was deprotected with HF/anisole and processed as usual to obtain the expected peptide. Electrospray MS was performed. (M+H)$^+$ found 582.3, calc. 582.

EXAMPLE IX

Synthesis of Ac-Tyr-Ile-{Ψ(CH$_2$NH)}-Arg-Leu-Pro—NH$_2$ a. Synthesis of Boc-Ile—H Aldehyde was synthesized from 1 g Boc-Ile-N (Me)OMe as described by Fehrentz and Castro (supra, 1983). The aldehyde was identified by TLC and NMR as described in the reference.

b. Synthesis of Arg(Tos)-Leu-Pro-MBHA

Synthesis of tripeptide resin was performed by general solid-phase approach described in Example I.

c. Synthesis of Boc-Ile-{Ψ(CH$_2$NH)}-Arg(Tos)-Leu-Pro-MBHA

Boc-Ile-H was coupled to the tripeptide resin Arg(Tos)-Leu-Pro-MBHA by reductive amination using NaBH$_3$CN in DMF containing 1% acetic acid. The Boc-group was cleaved as usual and Ac-Tyr—OH was coupled using DIC/HOBt. The finished peptide resin (0.7 g) was deprotected and cleaved from the resin using HF/thioanisole mixture. 19 mg of the crude Ac-Tyr-Ile-{Ψ(CH$_2$NH)}-Arg-Leu-Pro—NH$_2$ was HPLC purified on C18 column to give about 5 mg of >90% pure expected peptide. (M+H$^+$) found 688.4, calc. 687.9.

EXAMPLE X

Synthesis of Ac-Tyr-Ile-Dab(N$^\gamma$—C$_3$H$_7$N)-Leu-Ala—NH$_2$ 0.2 g SCAL-TG (0.2 mmol NH$_2$/g) (Patek & Lebl, *Tetr. Lett*. 32:3891–3894 (1991), which is incorporated herein by reference) was coupled with Fmoc-Ala—OH, Fmoc-Leu—OH, Fmoc-Dab(Boc)—OH, Fmoc-Ile—OH and Fmoc-Tyr(But)—OH using methods as described in Example I. After acetylation of the N-terminus and side chain deprotection by TFA, the peptide resin Ac-Tyr-Ile-Dab-Leu-Ala-SCAL-TG (SEQ ID NO:19) was washed, neutralized and treated with 0.3M PyBroP/NMI in DMF for 2 hr. The finished peptide was cleaved from the resin using 1M triphenyl phosphine/(CH$_3$)$_3$SiCl in DCM (3×1 hr), followed by 100% TFA (1 hr). After isolation of the crude peptide by diethyl ether precipitation, the peptide was lyophilized from a 0.1% aqueous solution of TFA. The peptide Ac-Tyr-Ile-Dab(N$^\gamma$—C$_3$H$_7$N)-Leu-Ala—NH$_2$ was purified by HPLC and characterized by MS. (M+H$^+$) found 676.4, calc. 676.4.

EXAMPLE XI

Synthesis of Ac-Tyr-Ile-PalMe(3)—NH$_2$

To 1.0 g Rink resin (0.48 mmol NH$_2$/g) was coupled Fmoc-Pal(3)—OH, Fmoc-Ile-OH and Fmoc-Tyr(But)—OH using the methods described in Example I. To 0.25 g of the finished peptide resin, Fmoc-Tyr(But)-Ile-Pal(3)-Rink, was added 500 μl methyl iodide (MeI) in DCM and the peptide resin was shaken for 6 hr. The finished peptide resin, Fmoc-Tyr(But)-Ile-PalMe(3)-Rink, was deprotected and acetylated and cleaved as described in Example I. A portion of the crude peptide was purified by HPLC and the final peptide was characterized by MS.

EXAMPLE XII

Synthesis of Ac-Cyclo(Glu-Tyr-Ile-Arg-Leu-Lys)—NH$_2$ (SEQ ID NO:20)

1 g SCAL-TG (0.29 mmol NH$_2$/g) (see Example X) was coupled with Fmoc-Lys(Boc)—OH, Fmoc-Leu—OH, Fmoc-Arg(Pmc)—OH, Fmoc-Ile—OH, Fmoc-Tyr(But)—OH and Fmoc-Glu(OtBu)—OH using methods as described in Example I. After Fmoc removal, the peptide resin was acetylated and washed with DMF, then with DCM. The peptide resin, Ac-Glu(OtBu)—Tyr(But)-Ile-Arg(Pmc)-Leu-Lys(Boc)-SCAL-TG (SEQ ID NO:21), was deprotected with reagent K, washed, neutralized and cyclized using BOP/HOBt/DIEA (5:5:5 eq) in DMF for 2 hr. The completion of coupling was monitored by ninhydrin test as described by Kaiser (Kaiser et al., *Anal. Biochem*. 34:595 (1970), which is incorporated herein by reference). After cyclization, the peptide was cleaved from the resin, purified by HPLC and characterized by MS. (M+H)$^+$ found: 844.5, calc. 844.5.

EXAMPLE XIII

Synthesis of Cyclo(Gly-Tyr-Ile-Ara-Gly)

1 g oxime resin (see Example VIII) (0.6 mmol NH$_2$/g) was coupled overnight with Boc-Gly—OH in the presence of DIC/HOBt. After washing and deprotection of the resin, Boc-Arg(Tos)—OH, Boc-Ile—OH and Boc-Tyr(2-BrZ)—OH were coupled using methods as described in Example VIII. One-third of the peptide resin, Boc-Tyr(2-BrZ)-Ile-Arg(Tos)-Gly-Oxime resin (SEQ ID NO:22), was deprotected and coupled with Boc-Gly by DIC/HOBt. The finished peptide resin was deprotected, neutralized and cyclized overnight in DMF containing 1% acetic acid. The resin was filtered and washed (DMF), the filtrates were combined and the organic solvent was removed by evaporation in vacuo. The residual peptide was deprotected (HF/anisole), lyophilized, HPLC purified and characterized by M.S. (M+H)$^+$ found: 547.8, calc. 547.8.

EXAMPLE XIV

Synthesis of N-substituted Glycine Compounds: Synthesis of Ac-(Bzl)Gly-(Chx)Gly-(3-guanidopropyl)Gly—NH$_2$ For the synthesis of N-substituted glycines, the procedure of Zuckermann et al. (*J. Am. Chem. Soc*. 114:10646 (1992), which is incorporated herein by reference) was used. 1 g SCAL-TG (0.29 mmol NH$_2$/g) (see Example X) was coupled with bromoacetic acid via symmetrical anhydride in DCM/DMF. Each coupling reaction was repeated twice. To Br—CH$_2$CO—SCAL-TG resin was added Boc—NH—CH$_2$CH$_2$CH$_2$NH$_2$ in DMSO and the resin was rocked for 2 hr. After deprotection, the process repeated by alternating the coupling of Br—CH$_2$COOH to the resin and the reaction of bromoacetic acid resin with the proper amine. The (Bzl)Gly-(Chx)Gly-(Boc—NH—(CH$_2$)$_3$) Gly-SCAL-TG resin was acetylated with acetic anhydride/DIEA/NMI (1:1:0.25) in DMF overnight. After deprotection of the Boc group, the resin, Ac-(Bzl)Gly-(Chx)Gly-(3-aminopropyl)Gly-SCAL-TG, was treated with 1.8M carboxyamidinopyrazole.HCl (Bernatowicz et al., *J. Org. Chem*. 57:2497–2502 (1992), which is incorporated herein by reference) in of presence of DIEA (1:1) in DMF for 3 h at RT. The completion of guanylation was monitored by the Kaiser test. Cleavage and processing of the resultant peptide was performed as described in Example X and analyzed by M. S. (M+H)$^+$ found 502.3, calc. 502.3.

EXAMPLE XV

Synthesis of diketopiperazine compounds: Synthesis of Cyclo(Ser-Ida)-Ile-Arg-Leu-Ala—NH$_2$ (SEQ ID NO:23)

The starting protected tetrapeptide, Fmoc-Ile-Arg(Pmc)-Leu-Ala-Rink (SEQ ID NO:23), was prepared by Fmoc strategy on Rink resin (see Example I). After Fmoc deprotection of the peptide resin, Fmoc-Ida(OMe)—OH (3 eq; DIC, HOBt) and Fmoc-Ser(tBu)—OH (7 eq; symmetrical anhydride) were coupled consecutively. The final deprotection and spontaneous ring closure were performed simultaneously by 1 hr exposure to 50% piperidine/DMF. After washing steps, the final peptide was cleaved and deprotected using TFA/thioanisole/H$_2$O (95:2.5:2.5). The resultant peptide was processed as described above and it was analyzed by HPLC (>95%) and by MS. (M+H)$^+$ found 655.4, calc. 655.38.

EXAMPLE XVI

Synthesis of Ph-C(NOCH$_2$Ph)—CO-I-R—NH$_2$ 0.2 g Rink resin was coupled with Fmoc-Arg(Pmc)—OH, Fmoc-Ile—OH, followed by removal of Fmoc protection (see Example I). To the peptide resin, Ile-Arg(Pmc)-Rink, was coupled with Ph-C(NOCH$_2$Ph)—COOH using the DIC/HOBt protocol described above. The finished peptide resin, Ph-C(NOCH$_2$Ph)-CO-Ile-Arg(Pmc)-Rink, was worked up as described in Example I and analyzed by MS. (M+H)+ found 524.3, calc. 524.6.

EXAMPLE XVII

Synthesis of Ac-pAph-Ile-Arg-Leu-Pro—NH$_2$ (SEQ ID NO:25)

The synthesis was performed on 100 mg Rink resin (0.48 mmol/g) according to the method of Example I, using the following amino acids derivatives: Fmoc-Pro—OH, Fmoc-Leu—OH, Fmoc-Arg(Pmc)—OH, Fmoc-Ile—OH and Fmoc-pAph-(Fmoc)—OH (racemic mixture). The cleavage and isolation of the peptide were carried out as described in Example I. Both diastereomeric peptides were isolated by RP—HPLC and identified by MS. (M+H)+ found 754.4. calc. 754.5.

EXAMPLE XVIII

Synthesis of Ac-Tyr-Chg-Arg-ol

The peptide sequence was built on 0.25 g Fmoc-Arg(Pmc)-Sasrin resin (0.5 mmol NH$_2$/g resin; Bachem Bioscience) using the method described in Example I. After N-terminus Fmoc deprotection and acetylation, the protected peptide was cleaved from the resin by reductive cleavage as a C-terminus alcohol (Mergler et al., *Peptides* pp. 177–178 (eds. Schneider and Eberle; Leiden 1993), which is incorporated herein by reference). The peptide resin was shaken with a solution of NaBH$_4$ (4 eq) in 2 ml THF:EtOH (6:1) for 24 hr. Following the cleavage reaction, the resin was washed with DCM, then the cleavage solution and washes were combined and lyophilized. The lyophilized peptide was deprotected by treatment with TFA/water/thioanisole (90:5:5) for 2 hr and isolated by precipitation. HPLC purified peptide was analyzed by MS. (M+H)+ found 505.3, calc. 505.3.

EXAMPLE XIX

Synthesis of Ac-Tyr-Chg-Arg-ol.acetate

The protected peptide alcohol was prepared as described in Example XVIII. 10 mg crude material was dissolved in DCM/ACN and treated with acetic anhydride (2 mmol) in the presence of TEA (2.4 mmol) for 20 min. The solution was filtered, evaporated and the peptide was deprotected as described above. HPLC purified peptide was analyzed by MS. (M+H)+ found 547.3, calc. 547.3.

EXAMPLE XX

Synthesis of Ac-Phe(pNH$_2$)-Chg-Orn(C(NH)CH$_3$)-Leu-Pro—NH$_2$ (SEQ ID NO:26)

1 g "TENTAGEL S" NH2 resin (0.28 mmol NH$_2$/g resin; Rapp Polymer; Tubingen Germany) was functionalized with SCAL linker as described in Example X and the following amino acids were coupled: Fmoc-Pro—OH; Fmoc-Leu—OH; Fmoc-Orn(Boc)—OH and Fmoc-Chg—OH. The peptide resin Fmoc-Chg-Orn(Boc)-Leu-Pro-SCAL-TG (SEQ ID NO:27) was treated with 50% TFA in DCM (1 wash for 1 min, then 1 wash for 30 min), washed 3× with DCM, neutralized with 5% DIEA in DCM (2×30 sec.) and 2× with DCM. To the peptide resin was added a solution of 1.5 g ethyl acetimidate hydrochloride (Aldrich) in 4 ml 1:1 pyridine:DIEA and 3 ml DMF and the coupling was continued overnight at RT.

The peptide resin, Fmoc-Chg-Orn(C(NH)CH$_3$)-Leu-Pro-SCAL-TG (SEQ ID NO:28), was deprotected with 20% piperidine in DMF for 12 min, washed 4× with DMF, 4× with DCM and Fmac-Phe(pNH-BOC)—OH was coupled using DIC/HOBt coupling in DMF. Deprotection of Fmoc and acetylation with acetic anhydride:pyridine (1:1) for 20 min gave the peptide resin, Ac-Phe(pNH-BOC)-Chg-Orn(C(NH)CH$_3$)-Leu-Pro-SCAL-TG (SEQ ID NO:29). Reduction of the SCAL linker and cleavage of the peptide, followed by HPLC purification of the crude product gave the expected compound. (M+H)+ found 740.2, caac. 740.48.

EXAMPLE XXI

Synthesis of Ac-Phe(pNH$_2$)-Chg-Dap(N$^\beta$-C$_6$H$_{11}$N)-Leu-Pro—NH$_2$ (SEQ ID NO:30)

0.5 g SCAL-TG (0.32 mmol NH$_2$/g) was coupled with Fmoc-Pro—OH, Fmoc-Leu—OH, Fmoc-Dapo(Boc)—OH and Fmoc-Chg—OH. The Boc group from the side chain was removed using 50% TFA for 20 min and the peptide resin was neutralized by washing with 10% DIEA/DCM. The free amino group of the side chain was transformed to the dimethylamidinium group by treatment of the peptide resin with 0.3M PyBroP/NMI in DMF for 20 min. Fmoc group deprotection with 50% piperidine/DMF for 60 min resulted in exchange of the dimethylamidinium by the piperidinium group in the side chain of Dap. The sequence was completed by coupling Fmoc-Phe(Boc)—OH and deprotection of the Fmoc group. The peptide was acetylated and cleaved as described in Example X. HPLC purified peptide was analyzed by MS. (M+H)+ found 752.4, calc. 752.4.

EXAMPLE XXII

Synthesis of Ac-pAph-Chg-PalMe(3)—NH$_2$ (SEQ ID NO:31)

Racemic H-Phe(pCN)—OH was synthesized by the acetamidomalonate method (Wagner et al., DDR Patent No. 155,954, issued Jul. 21, 1982; reexamined Nov. 9, 1988, which is incorporated herein by reference). The racemic Ac-pAph—OH was synthesized by conversion of the cyano group by ammonolysis of the corresponding methylthioimidate (offered by reaction of the cyano group with hydrogen sulfide) and subsequent methylation by MeI.

1 g "TENTAGEL" resin (substitution=0.21 mmol NH$_2$/g resin) and Knorr linker (Bernatowicz et al., *Tetr. Lett.* 30:4645 (1989), which is incorporated herein by reference) were used for synthesis of the peptide. The dipeptide, Fmoc-Chg-Pal-Knorr-TG, was assembled as described in Example I. 3-pyridylalanine subsequently was methylated by 1 ml MeI in DCM overnight. After Fmoc deprotection, Ac-pAph—OH was coupled using the DIC/HOBt method and the peptide was worked up as described in Example I. (M+H)+ found; 550.3, calc. 550.31.

EXAMPLE XXIII

Synthesis of Ac-Tyr-Chg-pAph-Leu-Pro—NH$_2$

The pentapeptide, Ac-Tyr(But)-Chg-Phe(pCN)-Leu-Pro-Knorr-TG (SEQ ID NO:32), was assembled on 0.4 g "TENTAGEL" (substitution=0.2 mmol NH$_2$/g resin) as described in Example I. The resin was treated overnight in a closed syringe with 8 ml pyridine/triethylamine (75:25) saturated with H$_2$S. The resin-bound thioamide was methylated using 0.5 ml MeI in 8 ml acetone for 30 min at 50 °C., then washed with acetone and methanol. The methylthioimide was reacted with ammonium acetate in methanol for 3 hr at 55° C. to obtain the final compound, which was cleaved from the resin and purified as described above. (M+H)+ found 761.4, calc. 760.43.

EXAMPLE XXIV

Synthesis of Ac-Phe(pCH$_2$NH$_2$)-Chg-Arg-Leu-Pro—NH$_2$ (SEQ ID NO:33)

Ac-DL-Phe(pCN)-Chg-Arg-Leu-Pro—NH$_2$ (crude peptide) was synthesized on 1 g Rink resin (0.6 mmol NH$_2$/g resin) as described in Example I. 125 mg crude peptide was dissolved in 50 ml MeOH and 0.5 ml Raney Ni suspension (Aldrich) was added. The mixture of the peptide and catalyst was hydrogenated at 35 psi for 4 hr at RT. The catalyst was filtered and the solution was evaporated to dryness. The residue was lyophilized from 0.1 % aqueous TFA containing 30% ACN. The dried crude product was purified by HPLC and analyzed by MS. (M+H)+ found 741.4, calc. 741.7.

EXAMPLE XXV

Synthesis of Ac-Phe(pC(NOH)NH$_2$)-Chg-Arg-Leu-Pro—NH$_2$ (SEQ ID NO:35)

21.1 mg crude peptide prepared as described in Example XXIV was mixed with 60.3 mg NH$_2$OH.HCl (Aldrich) in 1.5 ml MeOH, 0.7 ml pyridine and 0.5 ml TEA. The mixture was stirred for 72 hr at RT, then the solvent and volatile materials were evaporated in a vacuum. The peptide was purified by HPLC and analyzed by MS. (M+H)+ found 770.4, calc. 770.3.

EXAMPLE XXVI

Synthesis of A1-A2-B compounds

Figure 3A:
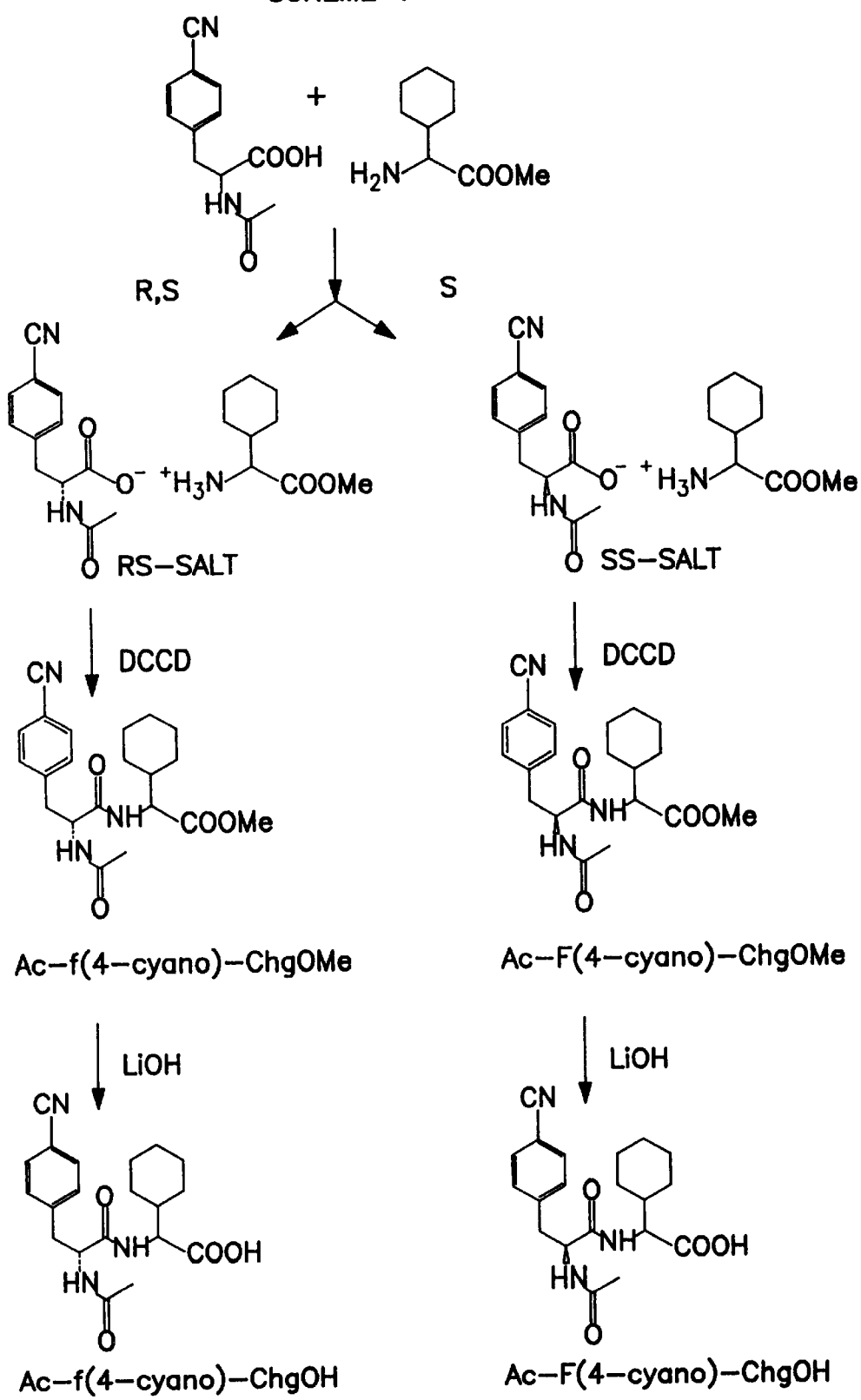
FIG. 3 shown a synthesis scheme for preparing some compounds of the invention.
Figure 3B:
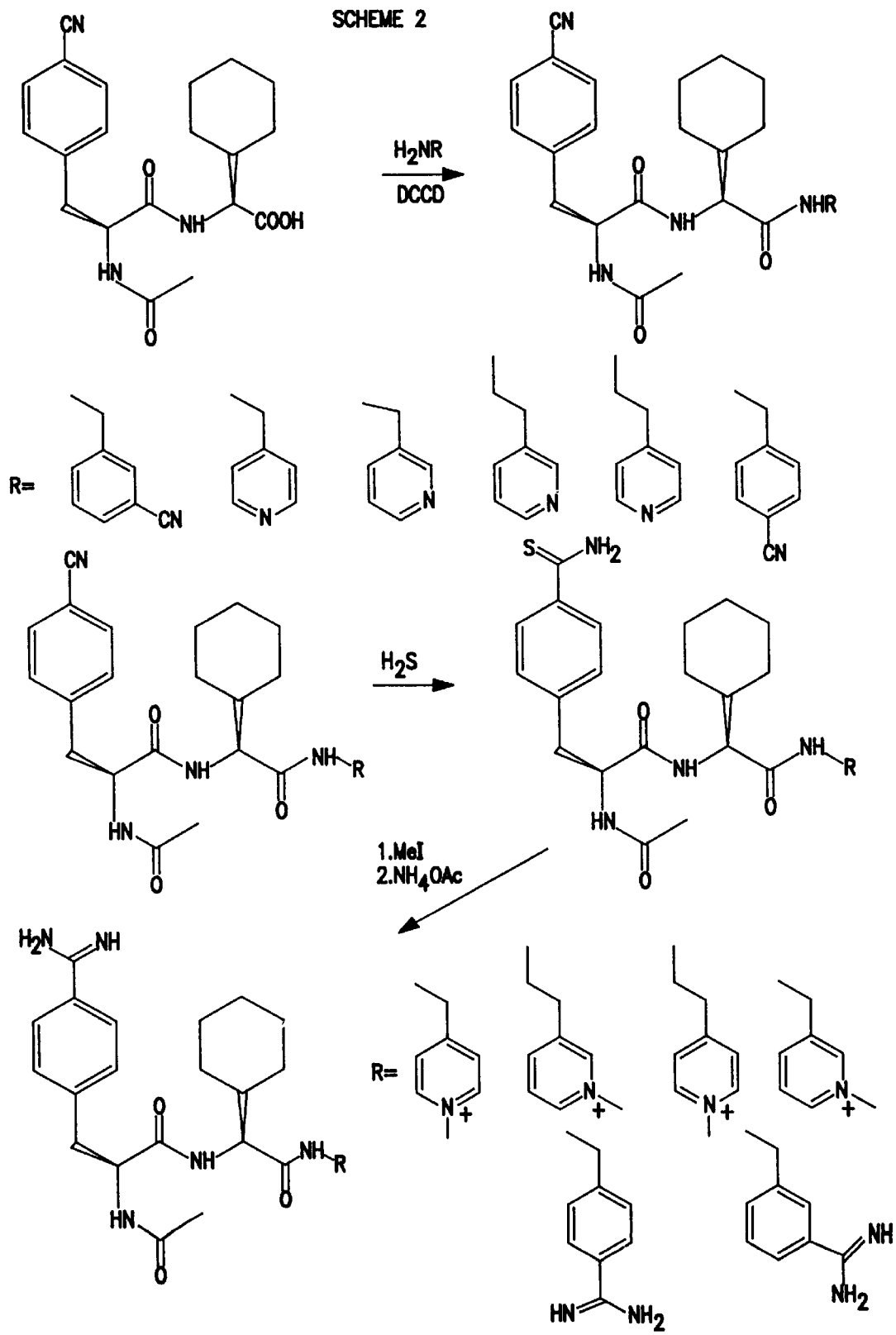

A1-A2-B compounds, i.e., A1-A2-(A3)$_m$—B compounds in which m is 0, were prepared as outlined in shown in FIG. 3. Briefly, coupling of racemic N-acetyl-4-cyanophenylalanine with L-cyclohexylglycine methyl ester, (H-Chg-OMe), yielded a mixture of two diastereomeric dipeptides, which were separated by chromatography. Racemic N-acetyl-4-cyanophenylalanine was partially resolved by forming the salt with L-cyclohexylglycine methyl ester. The less soluble D,L-salt was crystallized readily and subsequent coupling afforded the Ac-f(pCN)-Chg-OMe in substantially pure form. The "mother liquors" were enriched in the L,L-salt and coupling led to crude Ac-F(pCN)-Chg-OMe, which was further purified by chromatography over silica gel. These dipeptide esters were hydrolysed to the corresponding acids using lithium hydroxide in methanol/water at RT. Both dipeptide acids were converted to the substituted amides by conventional coupling with the appropriate amines, RNH$_2$. The amines that were not commercially available were prepared using standard chemical methods.

Conversion of cyano groups to the corresponding amidines was performed using standard chemical methods, either via the thioamide and methylthioimidate or by hydrogenation of the corresponding amidoxime (Example XXV). The latter was obtained by reacting the nitrile with hydroxylamine. The examples described below illustrate the preparation of the title compounds by these selected methods. It is recognized that compounds of the invention can be prepared using various other methods and that the procedures exemplified here were selected for convenience.

EXAMPLE XXVII

Synthesis of Ac-pAPh-Chg—NHCH$_2$-(4-methylpyridinium)

Synthesis of Ac-pAph-Chg—NHCH$_2$-(4-methylpyridinium) was accomplished by conversion of Ac-F(pCN)-Chg—NHCH$_2$-(4-pyridyl) using the methods described in Example XXII. The final compound was purified by HPLC as described in Example I. MS analysis: (M+H)+ found 493.3, calc. 493.29.

The starting material was prepared as follows:

a) Ac-(D,L)-F(pCN), 2.32 g (10 mmol) was dissolved in 75 ml ethanol by warming. L-cyclohexylglycine methyl ester (1.75 g, 10 mmol) was added and the mixture was stirred for 2 hr at RT. The precipitated crystals were filtered off and dried to yield 1.55 g D,L-salt. The filtrate was evaporated partially and diluted with ether. The separated crystals were collected and dried to leave 2.1 g L,L-salt contaminated with D,L-salt. The crude L,L-salt was combined with 20 ml DMF, 0.71 g HOBt and 1.18 g DCC. The mixture was stirred 24 hr at RT. The urea was filtered off and the filtrate was evaporated. The residue was dissolved in methylene chloride and the solution was washed with 1N HCl and saturated aqueous sodium bicarbonate. The organic layer was dried and evaporated. The residue was chromatographed over 60 g silica gel using 20% (v/v) acetone in methylene chloride for elution. Crystallization of the combined clean fractions from methylene chloride/ether/hexane gave 1.6 g Ac-F(pCN)-Chg-OMe as colorless crystals with melting point (mp) of 178°–180° C.

b) A mixture of 1.93 g(5 mmol) Ac-F(pCN)-Chg-OMe (from Example XXVII.a., above), 100 ml methanol, 10 ml water and 0.75 g lithium hydroxide hydrate was stirred under nitrogen for 24 hr Following addition of 2 ml acetic acid, the solvents were evaporated and the residue was partitioned between methylene chloride containing 20% isopropanol and 1N HCl. The organic layer was dried and evaporated and the residue was crystallized from methylene chloride/ether/hexane to leave 1.6 g of Ac-F(pCN)-Chg—OH as colorless crystals with mp 216°–218° C.

c) A mixture of 150 mg (0.4 mmol) Ac-F(pCN)-Chg—OH (above), 65 mg (0.6 mmol) 4-aminomethylpyridine, 124 mg (0.6 mmol) DCC, 60 mg (0.44 mmol) HOBt and 5 ml DMF was stirred for 20 hr at RT. The urea was removed by filtration and the filtrate was evaporated. The residue was slurried with methanol and the insoluble product was collected by filtration to leave 140 mg colorless Ac-F (pCN)-Chg—NHCH$_2$(4-pyridyl). An analytical sample was obtained by chromatography over silica gel using acetone:methylene chloride:methanol (4:5:1). The crystalline solid had mp >250° C.

EXAMPLE XXVIII

Ac-f(4-amidino)-Chg—NHCH$_2$(4-methylpyridinium)

This compound was prepared by reacting 150 mg Ac-f(pCN)-Chg—NHCH$_2$(4-pyridyl) (see above) with hydrogen sulfide, then with methyl iodide and ammonium acetate. The product was isolated by HPLC as a homogenous material MS analysis: (M+H)+ found 493.3, calc. 493.29.

The starting material was prepared as follows:

a) A mixture of 2.8 g Ac-f(pCN), (L)-cyclohexylglycine methyl ester, 940 mg HOBt, 1.57 g DCC and 30 ml of DMF was stirred for 2 days at RT. The urea was removed by filtration and the filtrate was evaporated. The residue was dissolved in methylene chloride and the solution was washed with 1N HCl and 10% aqueous sodium carbonate. The organic phase was dried and evaporated. Crystallization of the residue from methylene chloride/ether/hexane gave 2.05 g colorless Ac-f(pCN)-Chg-OMe having a mp 181°–183° C.

b) Hydrolysis of 1.93 g Ac-f(pCN)-Chg-OMe (above) with 0.75 g lithium hydroxide monohydrate in 100 ml methanol and 10 ml water was treated as described for the L,L-isomer in Example XXVII, above, crystallized from methylene chloride/ether, to produce 1.65 g Ac-f(pCN)-Chg—OH having a mp 180°–182° C.

c) A mixture of 225 mg Ac-f(pCN)-Chg—OH (above), 100 mg 4-aminomethylpyridine, 90 mg HOBt, 180 mg DCC and 6 ml DMF was stirred over a weekend at RT. The urea was filtered off and the filtrate was evaporated. The residue was stirred with methanol and the solids were removed by filtration to leave 190 mg crystalline Ac-f(pCN)-Chg—NHCH$_2$(4-pyridyl) having a mp >250° C.

EXAMPLE XXIX

Ac-pAph-Chg—NHCH$_2$CH$_2$(3-methylpyridinium)

A mixture of 125 mg of Ac-F(pCN)-Chg—NHCH$_2$CH$_2$(3-pyridyl), 2 ml DMSO, 10 ml pyridine and 5 ml triethylamine was saturated with hydrogen sulfide while cooled in ice/water. After stirring in a sealed vial overnight at RT, the solvents were evaporated and the residue was collected with acetone/ether and dried to leave 125 mg of the thioamide. This material was combined with 2 ml DMSO, 5 ml acetone and 0.75 ml methyl iodide and the mixture was stirred in a sealed vial overnight at RT. After dilution with toluene, the solvents were evaporated and the residue was stirred with ether. The ether was decanted, replaced by fresh ether and stirring was continued until the resinous material solidified, then the remaining ether was filtered off and the residue dried.

The resulting residue was dissolved in 20 ml methanol and treated with 0.3 ml acetic acid and 0.4 g ammonium acetate. The mixture was heated to 55°–60° C. for 2.5 hr, then solvents were evaporated. The residue was dissolved in water/ACN/TFA and lyophilized. The crude product was purified by HPLC. MS analysis: (M+H)$^+$ found 507.3, calc. 507.31.

The starting material was obtained as follows. A mixture of 150 mg (0.4 mmol) Ac-F(pCN)-Chg—OH, 120 mg (0.6 nmol)2-(3-pyridyl)ethylamine dihydrochloride, 125 mg DCC, 60 mg HOBt, 0.5 ml diisopropylethylamine and 10 ml DMF was stirred for 24 hr at RT. After evaporation of the solvent, the residue was stirred with methanol and the insoluble product was collected by filtration and washed with methanol and ether to leave 110 mg of colorless crystals. Thr filtrate was evaporated and the residue was dissolved in methylene chloride/isopropanol. This solution was washed with 10% aqueous sodium carbonate, dried and evaporated. The residue was chromatographed over 14 g silica gel using methylene chloride:acetone:methanol (5:4:1) to yield 40 mg Ac-F(pCN)-Chg—NHCH$_2$CH$_2$(3-pyridyl) having a mp 265°–268° C.

b)2-(3-pyridyl)ethylamine dihydrochloride was prepared as follows. A mixture of 1.3 g 3-pyridylacetonitrile, approximately 3 g Raney nickel and 30 ml methanol containing 10% ammonia by volume was hydrogenated at 35 psi for 20 hr using a Parr hydrogenator. The catalyst was filtered off over celite and the filtrate was evaporated. The residue was dissolved in methylene chloride, dried with magnesium sulfate, filtered and evaporated. The product was converted to the dihydrochloride using hydrogen chloride in dioxane. Crystallization from methanol/ether gave 1.4 g colorless crystals having a mp 145°–148° C.

EXAMPLE XXX

Ac-pAph-Chg—NHCH$_2$NH$_2$(4-methylpyridinium)

This compound was prepared using methods as described above by reacting Ac-F(pCN)-Chg—NHCH$_2$CH$_2$(4-pyridyl) with hydrogen sulfide followed by methylation with methyl iodide and reaction with ammonium acetate. The crude product was purified by HPLC. MS analysis: (M+H)$^+$ found 507.3, calc. 507.31.

The starting material was obtained by coupling of Ac-F(pCN)-Chg—OH with 2-(4-pyridyl)ethylamine dihydrochloride as described in Example XXIX, above.

2-(4-pyridyl)ethylamine dihydrochloride prepared as described for 2—(3-pyridyl)ethylamine dihydrochloride (above) by hydrogenation of pyridyl-4-acetonitrile over Raney nickel in the presence of ammonia. The dihydrochloride had a mp 220C°.

EXAMPLE XXXI

Ac-pAph-Chg—NHCH$_2$(4-amidinophenyl)

This compound was prepared using similar methods as described above by treating Ac-F(pCN)-Chg—NHCH$_2$(4-cyanophenyl) with hydrogen sulfide in DMSO, pyridine and triethylamine. The bis-thioamide obtained was methylated with methyl iodide in DMSO/acetone, then reacted with ammonium acetate as described above. The crude product was purified by HPLC. MS analysis: (M+H)$^+$ found 520.3, calc. 520.30.

The starting material was obtained as follows. A mixture of 75 mg (0.2 mmol of Ac-F(pCN)-Chg—OH, 50 mg (0.3 mmol) (4-cyanophenyl)methylamine hydrochloride, 62 mg DCC, 30 mg HOBt, 0.2 ml DIEA and 2 ml DMF was stirred for 24 hr at RT. After filtration, the solvent was evaporated and the residue was dissolved in methylene chloride containing 20 % of isopropanol. The solution was washed with 1N HCl and 10% aqueous sodium carbonate, then dried and evaporated. The residue was stirred with a small amount methanol/water and the separated solids were collected and dried to leave 80 mg Ac-F(pCN)-Chg—NHCH$_2$(4-cyanophenyl).

(4-Cyanophenyl)methylamine hydrochloride was prepared as follows. A mixture of 2 g (10 mmol) α-bromo-p-tolunitrile, 2 g (10.8 mmol) potassium phthalimide and 30 ml DMF was heated to reflux for 1 min. After cooling, the mixture was acidified with acetic acid and diluted with water to crystallize the product. The crystals were filtered, washed with water and dried to leave 2.24 g colorless N-(4-cyanophenyl)methylphthalimide having a mp 182°–184° C.

1.5 g N-(4-cyanophenyl)methylphthalimide was suspended in 50 ml boiling methanol and treated with 1 ml hydrazine hydrate. A clear solution resulted after 5 min. The methanol was evaporated and the residue was treated with 2N HCl. The suspension was heated to boiling and then cooled on ice. The solids were filtered off and the filtrate was evaporated. The residue was dissolved in water. The solution was heated to boiling again, cooled and filtered. The filtrate was made alkaline with sodium hydroxide and extracted with methylene chloride containing isopropanol. The organic phase was dried and evaporated and the residue was converted to the hydrochloride salt, crystallized from isopropanol/ether and yielded 0.43 g colorless crystals having a mp >260° C.

(3-Cyanophenyl)methylamine hydrochloride was prepared by reacting α-bromo-m-tolunitrile with potassium phthalimide to yield N-(3-cyanophenyl)methylphthalimide having a mp 147°–148° C. Reaction of this material with hydrazine hydrate and conversion to the hydrochloride as above gave (3-cyanophenyl)methylamine having a mp 223°–226° C.

EXAMPLE XXXII

Ac-pAph-Chg—NHCH$_2$(3-amidinophenyl)

This compound was prepared using methods as described above. Ac-F(pCN)-Chg—NHCH$_2$(3-cyanophenyl) was treated with hydrogen sulfide in DMSO, pyridine and triethylamine. The bis-thioamide obtained was methylated with methyl iodide in DMSO/acetone, then reacted with ammonium acetate as described above. The crude product was purified by HPLC. MS analysis: (M+S)$^+$ found 520.3, calc. 520.30.

The starting material was obtained as follows. A mixture of 300 mg (0.8 mmol) Ac-F(pCN)-Chg—OH, 200 mg (1.2 mmol) (3-cyanophenyl)methylamine hydrochloride, 250 mg DCC, 120 mg HOBt, 0.8 ml DIEA and 10 ml DMF was stirred for 24 hr at RT. After filtration, the solvent was evaporated and the residue was dissolved in a large volume of methylene chloride containing 20% isopropanol. The solution was washed with 1N HCl and 10% aqueous sodium carbonate, dried and evaporated. The residue was stirred with isopropanol/ether and the separated solids were collected and dried to leave 400 mg Ac-F(pCN)-Chg—NHCH$_2$ (3-cyanophenyl).

EXAMPLE XXXIII

Ac-pAph-Chg—NHCH(Me)(4-methylpyridinium)

A mixture of diastereomers of the title compound was prepared by reacting a mixture of two diastereomeric Ac-F(pCN)-Chg—NHCH(Me) (4-pyridyl) with hydrogen sulfide, then with MeI and ammonium acetate. The diastereomers were separated by HPLC. MS analysis: (M+H)$^+$ found 507.3, calc. 507.31.

The starting material was prepared as follows. A mixture of 150 mg (0.4 mmol) Ac-F(pCN)-Chg—OH, 120 mg (0.6 mmol) racemic 1-(4-pyridyl) ethylamine dihydrochloride, 125 mg DCC, 60 mg HOBt, 0.5 ml DIEA and 10 ml of DMF was stirred for 24 hr at RT. After filtration, the solvent was evaporated and the residue was dissolved in a large volume of methylene chloride containing 20% isopropanol. The solution was washed with 10% aqueous sodium carbonate, dried and evaporated. The residue was stirred with isopropanol/ether and the separated solids were collected and dried to leave 125 mg Ac-F(pCN)-Chg—NHCH(Me) (4-pyridyl) as a mixture of two diastereomers.

Racemic 1-(4-pyridyl)ethylamine dihydrochloride was prepared as follows. A mixture of 1 g 4-acetylpyridine-N-oxide, 2 g Raney nickel and 30 ml methanol containing 20% ammonia (v/v) was hydrogenated for 24 hr at 30 psi. The catalyst was removed by filtration over celite and the filtrate was evaporated. The residue was dissolved in methylene chloride, filtered and evaporated. The residue was dissolved in isopropanol and treated with hydrogen chloride in ether. The precipitated crystals were collected and dried to produce 0.9 g material having a mp 198°–200° C.

EXAMPLE XXXIV

Synthesis of DIPA(m) pAph-Chg-Arg-Leu-Pro—NH$_2$ (SEQ ID NO:36)

a. Synthesis of N,N-Diisopropyl amide of (p-cyanobenzyl) malonic acid(DIPA(m)Phe(pCN))—OH The synthesis of 2-(p-cyanobenzyl)malonic acid was achieved by a modified procedure (see Pinori et al, U.S. Pat. No. 5,061,911 (October, 1991), which is incorporated herein by reference). To a solution of 3.8 g 2,2-dimethyl-1,3-dioxane-4,6-dione (Meldrum's acid; Aldrich) and 1.12 g NaCNBH$_3$ (Aldrich) in 25 ml DMF was added 2.3 g p-cyanobenzaldehyde (Aldrich) and the mixture was stirred 2 hr at RT. To the reaction mixture was added 400 ml water and the solution was cooled in an ice bath and the pH was adjusted to 3.8–4 by dropwise addition of 20% HCl aqueous solution. The white precipitate was collected in a centered glass Buchner funnel and washed with cold water. The collected precipitate was dried in vacuo over CaCl$_2$ for 24 hr. The NMR of the collected solid in CDCl$_3$ indicated the compound 2,2-dimethyl-5—(p-cyano)benzyl-1,3-dioxane-4,6-dione (DCBD), which has a mp 135°–142° C. and R$_f$0.45 (CHCl$_3$:MeOH:acetic acid; 95:4:1).

To 1.5 ml diisopropylamine in 45 ml DCM was added 3 ml N,O-Bis(trimethylsilyl)acetamide (BSA) and the solution was refluxed in a reaction flask equipped with a magnetic stirrer and a condenser guarded with a CaCl$_2$ tube for 7 hr. After cooling the solution to RT, 0.8 g DCBD was added and the reaction mixture refluxed for 3 hr (until completion of conversion to the product as indicated by TLC). After cooling the reaction mixture, 5–8 ml 20% HCl aqueous solution was carefully added. After separation of the layers, the organic layer was washed with water, dried (MgSO$_4$) and evaporated to dryness to give a clean product that was used in the next step without further purification. The identification of the compounds was achieved by NMR in CDCL$_3$ and MS.

b. Synthesis of DIPA(m)pAph-Chg-Arg-Leu-Pro—NH$_2$

Peptide resin DIPA(m)Phe(pCN)-Chg-Arg(PMC)-Leu-Pro-Rink (SEQ ID NO:37) was synthesized by the method described in Example I. The resulting peptide resin was treated with hydroxylamine hydrochloride as described in Example XXV to give DIPA(m)Phe(pc(NOH)NH$_2$)-Chg-Arg(PMC)-Leu-Pro-Rink (SEQ ID NO:38). After cleavage of the peptide from the resin and lyophilization, the crude product (120 mg) was dissolved in 80 ml MeOH and 10 ml saturated solution of NH, in MeOH. To the reaction mixture was added 0.25 ml. Raney nickel suspension (Aldrich) and the mixture hydrogenated at 45 psi for 24 hr. The catalyst was filtered and the solvent evaporated to dryness and the residue lyophilized from 1:1 solution of 0.1% TFA aqueous solution and ACN. The crude peptide was purified by HPLC and the compound identified by MS. (M+H)$^+$ found 824.2, calc. 824.5.

EXAMPLE XXXV

Compounds with multiple substitutions that were synthesized and found potent inhibitors of factor Xa:

| No. | Compound | Calc. (Found) |
| --- | --- | --- |
| 1. | Ac-(2-CF$_3$Bzl)-Y-I-R-L-P-NH$_2$ (SEQ ID NO.:39) | 860.5 (860.3) |
| 2. | Ac-(CH$_3$CH$_2$CH$_2$CH(CH$_3$)CH$_2$)-Y-I-R-L-P-NH$_2$ (SEQ ID NO.:40) | 786.5 (786.5) |
| 3. | CH$_3$OCO-Y-I-R-L-P-NH$_2$ (SEQ ID NO.:41) | 742.4 (742.4) |
| 4. | Ac-Y-Chg-R-NH$_2$ | 518.2 (518.2) |
| 5. | Nal(2)-Cha-R-D(O-Allyl)-NH$_2$ (SEQ ID NO.:42) | 679.4 (679.4) |
| 6. | y-Tle-R-Nle-P-NH$_2$ | 660.4 (660.4) |
| 7. | Phe(pF)-I-R-L-P-NH (SEQ ID NO.:43) | 662.3 (662.3) |
| 8. | Ac-(D)Tic(OH)-I-R-L-P-NH$_2$ (SEQ ID NO.:44) | 714.4 (714.4) |
| 9. | Ac-Phe(pCN)-I-R-L-P-NH$_2$ (SEQ ID NO.:45) | 711.4 (711.4) |

-continued

| No. | Compound | Calc. (Found) |
|---|---|---|
| 10. | Ac-Phe(pCONH$_2$)-Chg-R-L-P-NH$_2$ (SEQ ID NO.:46) | 755.4 (755.4) |
| 11. | y-Chg-R-NH$_2$ | 476.2 (476.2) |
| 12. | Ac-W-Chg-R-L-P-NH$_2$ (SEQ ID NO.:47) | 751.3 (751.3) |
| 13. | Ac-Y-I-R-NH—CH(CH$_3$)—(CH$_2$)$_2$—CH$_3$ | 562.3 (562.3) |
| 14. | Ac-Y-Pgl-R-L-P-NH$_2$ (SEQ ID NO.:48) | 722.2 (722.2) |
| 15. | Ac-Y-Chg-R-Ina-NH$_2$ (SEQ ID NO.:49) | 629.4 (629.4) |
| 16. | Ac-Tza-Chg-R-NH$_2$ | 509.3 (509.3) |
| 17. | Ac-Y-Chg-R-Pip-NH$_2$ (SEQ ID NO.:288) | 629.4 (629.4) |
| 18. | Ac-Phe(pNH$_2$)-Chg-R-NH$_2$ | 517.2 (517.2) |
| 19. | Ac-(Bzl)G-(Chx)Gly-(3-guanidinopropyl)G-NH$_2$ | 502.3 (502.3) |
| 20. | Ac-Y-Chg-R-ol.acetate | 547.3 (547.3) |
| 21. | Ac-Y-Chg-R-OCH$_3$ | 533.3 (533.3) |
| 22. | Ac-Y-Chg-R-OH | 519.3 (519.3) |
| 23. | Bz-Y-Chg-R-NH$_2$ | 532.2 (532.2) |

EXAMPLE XXXVI

Combinations of chemical chances that individually may not have improved activity can improve activity Inhibition of factor Xa activity was measured. However, any relevant measure of biological activity such as the effect of a YIR peptide of the invention on coagulation, in vivo potency, in viva half-life, oral bioavailability, oral potency or half-life can be determined as a measure of the activity of a peptide of the invention.

Many specific changes are depicted. As an example, two changes were combined to demonstrate that a further improvement of activity was obtained by combining changes, even where the original single changes did not significantly improve activity. Single chemical changes produced Ac-Y-I-R-L-P, which had a Ki=0.49 $\mu$M and (iBu)Y-I-R-L-P, which had a Ki=2.6 $\mu$M, compared to the parent compound, Y-I-R-L-P (SEQ ID NO:50)(Ki=5.3 $\mu$M). Combining these two changes produced Ac-(iBu)Y-I-R-L-P—NH$_2$, which had a Ki=0.04 $\mu$M. Thus, these results demonstrate that a peptide of the invention having a combination of two chemical changes can have substantially increased factor Xa inhibitory activity as compared to the corresponding single change analogs, even where one parent compound such as (iBu)Y-I-R-L-P—NH$_2$ did not have a significantly improved activity compared to the parent Y-I-R-L-P—NH$_2$.

Table 3 exemplifies specific chemical modifications that resulted in compounds having Ki values between 100 $\mu$M and 1 pM for factor Xa inhibition.

TABLE 3

Factor Xa Inhibitions having a Ki < 100 $\mu$M

| Structure | MS* | AA* |
|---|---|---|
| (2,2-DiMe-Propyl)Y-I-R-L-P-NH$_2$ (SEQ. ID. NO.:51) | OK | OK |
| (2-CF$_3$-Bzl)Y-I-R-L-P-NH$_2$ (SEQ. ID. NO.:52) | OK | OK |
| (2-Et-nBu)Y-I-R-L-P-NH$_2$ (SEQ. ID. NO.:53) | OK | OK |
| (2-Me-Bzl)Y-I-R-L-P-NH$_2$ (SEQ. ID. NO.:54) | OK | OK |
| (2-Me-nBu)Y-I-R-L-P-NH$_2$ (SEQ. ID. NO.:55) | OK | OK |
| (2-Me-nPentyl)Y-I-R-L-P-NH$_2$ (SEQ. ID. NO.:56) | OK | OK |
| (3,3-DiMe-nBu)Y-I-R-L-P-NH$_2$ (SEQ. ID. NO.:57) | OK | OK |
| 3-phenoxyproprionic-Y-Chg-R-NH$_2$ | | |
| 5-Bzim-CO-Chg-R-L-P-NH$_2$ (SEQ. ID. NO.:58) | OK | OK |
| 5-Bzim-CO-F(pNH$_2$)-Chg-R-L-P-NH$_2$ (SEQ. ID. NO.:59) | OK | OK |
| Y(3,5-Br)-I-R-L-P-NH$_2$ (SEQ. ID. NO.:60) | OK | OK |
| Y(3,5-I)-I-R-L-P-NH$_2$ (SEQ. ID. NO.:61) | OK | OK |
| (Chx-CH$_2$)Y-I-R-L-P-NH$_2$ (SEQ. ID. NO.:62) | OK | OK |

TABLE 3-continued

Factor Xa Inhibitions having a Ki < 100 $\mu$M

| Structure | MS* | AA* |
|---|---|---|
| (iBu)Y-I-R-OH | OK | OK |
| (iBu)Y-I-R-L-A-NH$_2$ (SEQ. ID. (NO.:63) | OK | OK |
| (iBu)Y-I-R-L-P-NH$_2$ (SEQ. ID. NO.:64) | OK | OK |
| (Me)y-I-R-L-A-NH$_2$ | | |
| (Me)Y-I-R-L-A-NH$_2$ (SEQ. ID. NO.:65) | OK | OK |
| (Me)y-I-R-L-P-NH$_2$ | | |
| (Me)Y-I-R-L-P-NH$_2$ (SEQ. ID. NO.:66) | OK | OK |
| 5-Hic-Chg-R-NH$_2$ | OK | OK |
| Ac-(1,2,3,6-4H-Bzl)Y(SO$_3$H)-I-R-L-P-NH$_2$ (SEQ. ID. NO.:67) | OK | OK |
| Ac-(1,2,3,6-4H-Bzl)Y-I-R-L-P-NH$_2$ (SEQ. ID. NO.:68) | OK | OK |
| Ac-(2,3-DiMe-nPentyl)Y(SO$_2$H)-I-R-L-P-NH$_2$ (SEQ. ID. NO.:69) | OK | OK |
| Ac-(2,3-DiMe-nPentyl)Y-I-R-L-P-NH$_2$ (SEQ. ID. NO.:70) | OK | OK |
| Ac-(2-CF$_3$-Bzl)Y(SO$_3$H)-I-R-L-P-NH$_2$ (SEQ. ID. NO.:71) | OK | OK |
| Ac-(2-CF$_3$-Bzl)Y-I-R-L-P-NH$_2$ (SEQ. ID. NO.:72) | OK | OK |
| Ac-(2Et-nBu)Y-I-R-L-P-NH$_2$ (SEQ. ID. NO.:73) | OK | OK |
| Ac-(2-Me-Bzl)Y(SO$_3$H)-I-R-L-P-NH$_2$ (SEQ. ID. NO.:74) | OK | OK |
| Ac-(2-Me-Bzl)Y-I-R-L-P-NH$_2$ (SEQ. ID. NO.:75) | OK | OK |
| Ac-(2-Me-nBu)Y(SO$_3$H)-I-R-L-P-NH$_2$ (SEQ. ID. NO.:76) | OK | OK |
| Ac-(2-Me-nBu)Y-I-R-L-P-NH$_2$ (SEQ. ID. NO.:77) | OK | OK |
| Ac-(2-Me-nPentyl)Y(SO$_3$H)-I-R-L-P-NH$_2$ (SEQ. ID. NO.:78) | OK | OK |
| Ac-(2-Me-nPentyl)Y-I-R-L-P-NH$_2$ (SEQ. ID. NO.:79) | OK | OK |
| Ac-(3,3-DiMe-nBu)Y(SO$_3$H)-I-R-L-P-NH$_2$ (SEQ. ID. NO.:80) | OK | OK |
| Ac-(3,3-DiMe-nBu)Y-I-R-L-P-NH$_2$ (SEQ. ID. NO.:81) | OK | OK |
| Ac-3,3-DiMe-nPentyl)Y(SO$_3$H)-I-R-L-P-NH$_2$ (SEQ. ID. NO.:82) | OK | OK |
| Ac-(3,5,5-Me-3-nHexyl)Y-I-R-NH$_2$ | OK | OK |
| Ac-(3,5,5-Me-3-nHexyl)Y-L-R-L-P-NH$_2$ (SEQ. ID. NO.:83) | OK | OK |
| Ac-(4-pyridyl-CH$_2$-)Y-I-R-NH$_2$ | OK | OK |
| Ac-(4-MeO-Bzl)Y-I-R-NH$_2$ | OK | OK |
| Ac-(Bzl)Y-I-R-NH$_2$ | OK | OK |
| Ac-(Chx-CH$_2$)Y-I-R-L-P-NH$_2$ (SEQ. ID. NO.:84) | OK | OK |
| Ac-(Cyclopropyl-CH$_2$)Y(SO$_3$H)-I-R-L-P-NH$_2$ (SEQ. ID. NO.:85) | OK | OK |
| Ac-(Cyclopropyl-CH$_2$)Y-I-R-L-P-NH$_2$ (SEQ. ID. NO.:86) | OK | OK |
| Ac-(Et-CH=C(CH$_3$)—CH$_2$)Y(SO$_3$H)-I-R-L-P-NH$_2$ (SEQ. ID. NO.:87) | OK | OK |
| Ac-(Et-CH=C(CH$_3$)—CH$_2$)Y-I-R-L-P-NH$_2$ (SEQ. ID. NO.:88) | OK | OK |
| Ac-(iBu)F(pNH$_2$)-Chg-R-NH$_2$ | | |
| Ac-(iBu)F(pNH$_2$)-Chg-R-L-P-NH$_2$ (SEQ. ID. NO.:89) | OK | OK |
| Ac-(iBu)Nal(2)-Chg-R-L-P-NH$_2$ (SEQ. ID. NO.:90) | OK | OK |
| Ac-(iBu)Y-Chg-R-NH$_2$ | OK | OK |
| Ac-(iBu)Y-Chg-R-L-P-NH$_2$ (SEQ. ID. NO.:91) | OK | OK |
| Ac-(iBu)Y-I-Dab(N$^\gamma$-C$_3$H$_7$)-L-P-NH$_2$ (SEQ. ID. NO.:92) | OK | OK |
| Ac-(iBu)Y-I-Orn(N$^6$-C$_3$H$_7$N)-L-P-NH$_2$ | | |
| Ac-(iBu)Y-I-R-NH$_2$ | OK | OK |
| Ac-(iBu)Y-I-R-L-P-NH$_2$ | OK | OK |
| Ac-(Me)Y-Chg-R-L-P-NH$_2$ | OK | OK |
| Ac-(Me)Y-I-R-L-A-NH$_2$ | OK | OK |
| Ac-(Me)Y-I-R-L-P-NH$_2$ | OK | OK |
| Ac-(nBu)Y-I-R-NH$_2$ | OK | OK |
| Ac-(trans)-CH$_3$—CH=C(CH$_3$)—CH$_2$)Y-I-R-L-P-NH$_2$ | OK | OK |
| Ac-Tyr(3,5-NO$_2$)-I-R-L-P-NH$_2$ | OK | OK |
| Ac-(Bzl)G-(Chx)Gly-(3-GuanidoPropyl)G-NH$_2$ | | |
| Ac-βAla-Y-I-R-G-NH$_2$ (SEQ. ID. NO.:100) | OK | OK |
| Ac-E-Y-I-R-L-K-NH$_2$** (SEQ. ID. NO.:101) | OK | OK |
| Ac-E-Y-I-R-L-P-K-NH$_2$ (SEQ. ID. NO.:102) | OK | OK |
| Ac-F(pCONH$_2$)-Chg-R-L-P-NH$_2$ (SEQ. ID. NO.:103) | OK | OK |
| Ac-F(pCONH$_2$)-I-R-L-P-NH$_2$ (SEQ. ID. NO.:104) | OK | OK |
| Ac-F(pF)-I-R-L-P-NH$_2$ (SEQ. ID. NO.:105) | OK | OK |
| Ac-f(pF)-I-R-L-P-NH$_2$ | | |
| Ac-F(pCN)-I-R-L-P-NH$_2$ (SEQ. ID. NO.:106) | OK | OK |
| Ac-F(pNH$_2$)-Chg-R-NH$_2$ | | |
| Ac-F(pNH$_2$)-Chg-R-L-P-NH$_2$ (SEQ. ID. NO.:107) | OK | OK |
| Ac-F(pNH$_2$)-I-R-L-P-NH$_2$ (SEQ. ID. NO.:108) | OK | OK |
| Ac-F(pNH$_2$)-Chg-R-(Bzl)G-G-OH (SEQ. ID. NO.:109) | OK | OK |
| Ac-F(pNH$_2$)-Chg-R-(Chx)G-G-OH (SEQ. ID. NO.:110) | OK | OK |
| Ac-F(pNH$_2$)-Chg-R-(CH$_3$CH$_2$CH$_2$(CH$_3$))G-G-OH (SEQ. ID. NO.:111) | OK | OK |
| Ac-G-G-Y-I-R-G-NH$_2$ (SEQ. ID. NO.:112) | OK | OK |

TABLE 3-continued

Factor Xa Inhibitions having a Ki < 100 μM

| Structure | MS* | AA* |
|---|---|---|
| Ac-G-Y-Nle-R-L-NH₂ (SEQ. ID. NO.:113) | OK | OK |
| Ac-G-y-Nle-R-L-NH₂ | OK | OK |
| Ac-G-Y-I-R-G-NH₂ (SEQ. ID. NO.:114) | OK | OK |
| Ac-G-Y-I-R-L-NH₂ (SEQ. ID. NO.:115) | OK | OK |
| Ac-Nal(1)-I-R-L-P-NH₂ (SEQ. ID. NO.:116) | OK | OK |
| Ac-Nal(2)-Cha-R-D(O-Allyl)-NH₂ (SEQ. ID. NO.:117) | OK | OK |
| Ac-Nal(2)-Cha-R-L-NH₂ (SEQ. ID. NO.:118) | OK | OK |
| Ac-Nal(2)-Chg-R-NH₂ | OK | OK |
| Ac-Nal(2)-Chg-R-L-P-NH₂ (SEQ. ID. NO.:119) | OK | OK |
| Ac-Nal(2)-I-R-L-P-NH₂ (SEQ. ID. NO.:120) | OK | OK |
| Ac-Pgl(OH)-I-R-L-NH₂ (SEQ. ID. NO.:121) | OK | OK |
| Ac-pAph-Chg-R-L-P-NH₂ (SEQ. ID. NO.:122) | OK | OK |
| Ac-pAph-I-R-L-P-NH₂ (SEQ. ID. NO.:123) | OK | OK |
| Ac-Phe(pGua)-I-R-L-P-NH₂ (SEQ. ID. NO.:124) | OK | OK |
| Ac-S-Y-I-R-L-P-NH₂ (SEQ. ID. NO.:125) | OK | OK |
| Ac-W-Chg-R-L-P-NH₂ (SEQ. ID. NO.:126) | OK | OK |
| Ac-W-L-R-L-A-NH₂ (SEQ. ID. NO.:127) | OK | OK |
| Ac-Y(Me)-I-R-L-A-NH₂ | OK | OK |
| Ac-Y(Me)-I-R-L-P-NH₂ | OK | OK |
| Ac-Y-(allo-I)-R-L-P-NH₂ (SEQ. ID. NO.:128) | OK | OK |
| Ac-Y-Cha-R-L-P-NH₂ (SEQ. ID. NO.:129) | OK | OK |
| Ac-Y-Chg-R-NH₂ | OK | OK |
| Ac-Y-Chg-R-NH-CH₂CH₂—N(CH₃)₄ | OK | OK |
| Ac-Y-Chg-R-NH-Bzl-4-OMe | OK | OK |
| Ac-Y-Chg-R-NH—CH₂-Chx | OK | OK |
| Ac-Y-Chg-R-NH—CH₂CH₂—N—(CH₃)₂ | OK | OK |
| Ac-Y-Chg-R-NH—CH₂CH₂—O—CH3 | OK | OK |
| Ac-Y-Chg-R-NH—CH₂CH₂—COOH | OK | OK |
| Ac-Y-Chg-R-NH-Chx | OK | OK |
| Ac-Y-Chg-R-NH—CH₂(2-(1-Et)pyrrolidinyl | OK | OK |
| Ac-Y-Chg-R-NH—CH₂(2-(6-EtO)benzylthiazolyl) | OK | OK |
| Ac-Y-Chg-R-L-P-NH₂ (SEQ. ID. NO.:130) | OK | OK |
| Ac-Y-Chg-R(NO₂)-{Ψ(CH₂NH)}-L-NH2 (SEQ. ID. NO.:131) | OK | OK |
| Ac-Y-Nva-R-NH₂ | OK | OK |
| Ac-Y-Pen(Me)-R-L-P-NH₂ (SEQ. ID. NO.:132) | OK | OK |
| Ac-Y-Pgl-R-L-P-NH₂ (SEQ. ID. NO.:133) | OK | OK |
| Ac-Y-{Ψ(CH₂N(Ac))}-I-R-L-P-NH₂ (SEQ. ID. NO.:134) | OK | ok |
| Ac-Y-{Ψ(CH₂NH)}-I-R-L-P-NH₂ (SEQ. ID. NO.:135) | OK | OK |
| Ac-Y-I-R-{Ψ(COCH₂)}-G-P-NH₂ (SEQ. ID. NO.:136) | OK | OK |
| Ac-Y-I-Dab(Nᵞ-C₃H₇N)-L-A-NH₂ (SEQ. ID. NO.:137) | OK | OK |
| Ac-Y-I-hR-L-A-NH₂ (SEQ. ID. NO.:138) | OK | OK |
| Ac-Y-I-nR-L-A-NH₂ (SEQ. ID. NO.:139) | OK | OK |
| Ac-Y-I-PalMe(3)-NH₂ | OK | OK |
| Ac-Y-I-PalMe(3)-L-NH₂ (SEQ. ID. NO.:140) | OK | OK |
| Ac-Y-I-{Ψ(CH₂NH)}-R-L-P-NH₂ (SEQ. ID. NO.:141) | OK | OK |
| Ac-y-I-R-NH₂ | OK | OK |
| Ac-Y-I-R-NH₂ | OK | OK |
| Ac-Y-I-R-N(Me)O—CH₃ | OK | OK |
| Ac-Y-I-R-NH—CH₂-4-Pyridyl | OK | OK |
| Ac-Y-I-R-NH—CH₂CH₂—N(CH₃)₂ | OK | OK |
| Ac-Y-I-R-NH-4-morpholinyl | OK | OK |
| Ac-Y-I-R-NH—OCH3 | OK | OK |
| Ac-Y-I-R-Nle-Hyp (SEQ. ID. NO.:142) | OK | OK |
| Ac-Y-I-R-Nle-Δ²P (SEQ. ID. NO.:143) | OK | OK |
| Ac-Y-I-R-Piperidyl | OK | OK |
| Ac-Y-I-R-I (SEQ. ID. NO.:144) | OK | OK |
| Ac-Y-I-R-I-P (SEQ. ID. NO.:145) | OK | OK |
| Ac-Y-I-R-L (SEQ. ID. NO.:146) | OK | OK |
| Ac-y-I-R-L-A | OK | OK |
| Ac-Y-I-R-L-A (SEQ. ID. NO.:147) | OK | OK |
| Ac-Y-I-R-L-A-A-F-T-NH₂ (SEQ. ID. NO.:148) | OK | OK |
| Ac-y-I-R-L-P-NH₂ | OK | OK |
| Ac-Y-I-R-L-P-NH₂ (SEQ. ID. NO.:149) | OK | OK |
| Ac-Y-I-R-L-P-Dab(Ac-Y-I-R-L-P(G-A)₃)-OH | OK | OK |
| Ac-Y-I-R-L-P-Dab(Ac-Y-I-R-L-P(G-A)₆)-OH | OK | OK |
| Ac-Y-I-R-L-P-Dab(Ac-Y-I-R-L-P)-OH | OK | OK |
| Ac-Y-I-R-P-NH₂ (SEQ. ID. NO.:150) | OK | OK |
| Ac-Y-K-R-L-E-NH₂ (SEQ. ID. NO.:151) | OK | OK |
| Ac-Y-N-R-L-NH₂ (SEQ. ID. NO.:152) | OK | OK |
| Ac-Y-N-R-L-P-NH₂ (SEQ. ID. NO.:153) | OK | OK |
| Ac-Y-T(Me)-R-L-P-NH₂ (SEQ. ID. NO.:154) | OK | OK |
| βAla-Y-I-R-G (SEQ. ID. NO.:155) | OK | OK |
| βAla-Y-I-R-G-NH₂ (SEQ. ID. NO.:156) | OK | OK |
| Caff-I-R-NH₂ | | |
| Cbz-I-R-L-NH₂ | OK | OK |
| Cbz-Y-I-R-NH₂ | OK | OK |
| CClF₂—CO-Y-I-R-L-P-NH₂ (SEQ. ID. NO.:157) | OK | OK |
| CF₂H—CO-Y-I-R-L-P-NH₂ (SEQ. ID. NO.:158) | OK | OK |
| CF₃—CF₂CO-Y-I-R-L-P-NH₂ (SEQ. ID. NO.:159) | OK | OK |
| CH₃—CHCl—CO-Y-I-R-L-P-NH₂ (SEQ. ID. NO.:160) | OK | OK |
| CH₃—O—CO-Y-I-R-L-P-NH₂ (SEQ. ID. NO.:161) | OK | OK |
| CH₃—SO₂-Y-I-R-L-P-NH₂ (SEQ. ID. NO.:162) | OK | OK |
| CH₃CH₂—O—CO-Y-I-R-L-P-NH₂ (SEQ. ID. NO.:163) | OK | OK |
| Cl₂CHCO-Y-I-R-L-P-NH₂ (SEQ. ID. NO.:164) | OK | OK |
| ClCH₂CO-Y-I-R-NH₂ | OK | OK |
| C-Y-I-R-L-C-NH₂ (SEQ. ID. NO.:165) | OK | OK |
| D-Tic-I-R-L-A-A-F-T-NH₂ (SEQ. ID. NO.:166) | OK | OK |
| Et(Et)Y-I-R-L-P-NH₂ (SEQ. ID. NO.:167) | OK | OK |
| E-Y-I-R-K-NH₂ (SEQ. ID. NO.:168) | OK | OK |
| E-Y-I-R-L-K-NH₂ (SEQ. ID. NO.:169) | OK | OK |
| E-Y-I-R-L-P-K-NH₂ (SEQ. ID. NO.:170) | OK | OK |
| F(pCl)-I-R-I-Sar-NH₂ (SEQ. ID. NO.:171) | OK | OK |
| F(pF)-I-R-L-P-NH₂ (SEQ. ID. NO.:172) | OK | OK |
| f(pF)-I-R-L-P-NH₂ | OK | OK |
| F(pNH₂)-I-R-L-A-NH₂ (SEQ. ID. NO.:173) | OK | OK |
| F(pNO₂)-I-R-L-A-NH₂ (SEQ. ID. NO.:174) | OK | OK |
| f-I-R-F-P-NH₂ | OK | OK |
| f-I-R-L-P-NH₂ | OK | OK |
| F-I-R-L-NH₂ (SEQ. ID. NO.:175) | OK | OK |
| F-I-R-L-P-H-Y-G-NH₂ (SEQ. ID. NO.:176) | OK | OK |
| F-I-R-L-Y-V-W-N-NH₂ (SEQ. ID. NO.:177) | OK | OK |
| For-y-I-R-L-P-NH₂ | OK | OK |
| For-T-I-R-L-P-NH₂ (SEQ. ID. NO.:178) | OK | OK |
| G-G-Y-I-R-G-NH₂ (SEQ. ID. NO.:179) | OK | OK |
| G-Y-I-R-D-NH₂ (SEQ. ID. NO.:180) | OK | OK |
| G-Y-I-R-F-NH₂ (SEQ. ID. NO.:181) | OK | OK |
| G-Y-I-R-G-NH₂ (SEQ. ID. NO.:182) | OK | OK |
| G-Y-I-R-G (SEQ. ID. NO.:183) | OK | OK |
| G-Y-I-R-H-NH₂ (SEQ. ID. NO.:184) | OK | OK |
| G-Y-I-R-I-NH₂ (SEQ. ID. NO.:185) | OK | OK |
| G-Y-I-R-K-NH₂ (SEQ. ID. NO.:186) | OK | OK |
| G-Y-I-R-L-NH₂ (SEQ. ID. NO.:187) | OK | OK |
| G-Y-I-R-L-P-NH₂ (SEQ. ID. NO.:188) | OK | OK |
| G--I-R-L-P-A-M-NH₂ (SEQ. ID. NO.:189) | OK | OK |
| G-Y-I-R-L-P-P-V-NH₂ (SEQ. ID. NO.:190) | OK | OK |
| G-Y-I-R-L-P-Q-T-NH₂ (SEQ. ID. NO.:191) | OK | OK |
| G-Y-I-R-L-P-S-Q-NH₂ (SEQ. ID. NO.:192) | OK | OK |
| G-Y-I-R-S-NH₂ (SEQ. ID. NO.:193) | OK | OK |
| G-Y-I-R-T-NH₂ (SEQ. ID. NO.:194) | OK | OK |
| G-Y-I-R-V-NH₂ (SEQ. ID. NO.:195) | OK | OK |
| G-Y-I-R-W-NH₂ (SEQ. ID. NO.:196) | OK | OK |
| G-Y-I-R-Y-NH₂ (SEQ. ID. NO.:197) | OK | OK |
| (pOH)C₆H₄—CH₂CH(OH)—CO-I-R-L-Sar-NH₂ (SEQ. ID. NO.:198) | OK | OK |
| (pOH)C₆H₄—CH₂CH₂CO-I-R-L-A-NH₂ (SEQ. ID. NO.:199) | OK | OK |
| (pOH)C₆H₄—CH₂CH₂CO-I-R-L-P-NH₂ (SEQ. ID. NO.:200) | OK | OK |
| (pOH)C₆H₄—CH₂CHOH—CO-I-R-L-P-NH₂ (SEQ. ID. NO.:201) | OK | OK |
| (pOH)C₆H₄—OCH(CH₃)CO-I-R-L-P-NH₂ (SEQ. ID. NO.:202) | OK | OK |
| (pOH)C₆H₄—OCH₂CO-I-R-L-P-NH₂ (SEQ. ID. NO.:203) | OK | OK |
| I-H-L-W-Y-I-R-L-P-NH₂ (SEQ. ID. NO.:204) | OK | OK |
| I-H-L-W-y-I-R-L-P-NH₂ | OK | OK |
| I-Q-L-G-Y-I-R-L-P-NH₂ (SEQ. ID. NO.:205) | OK | OK |
| 4-MeO—C₆H₄—CO-I-R-L-A-NH₂ (SEQ. ID. NO.:206) | OK | OK |
| N-morpholinyl-CO-F-I-R-L-P-NH₂ (SEQ. ID. NO.:207) | OK | OK |
| Nal(2)-Cha-R-D(O-Allyl)-NH₂ (SEQ. ID. NO.:208) | OK | OK |
| Nal(2)-Cha-R-D(O-Allyl)-Sar-NH₂ (SEQ. ID. NO.:209) | OK | OK |
| Nal(2)-Chg-R-L-P-NH₂ (SEQ. ID. NO.:210) | OK | OK |
| Nal(2)-I-R-C(Me)-P-NH₂ (SEQ. ID. NO.:211) | OK | OK |
| N-G-Y-I-R-L-I-H-NH₂ (SEQ. ID. NO.:212) | OK | OK |
| pal-C(SBut)-R-L-P-NH₂ | OK | OK |
| pal-I-R-C(SBut)-Hyp-NH₂ | OK | OK |
| pal-I-R-C(SBut)-P-NH₂ | OK | OK |
| Pgl(OH)-I-R-L-NH₂ (SEQ. ID. NO.:213) | OK | OK |
| Ph-C(NOCH₂Ph)—CO-I-R-NH₂ | OK | OK |
| Ph-CH=CH—CO-I-R-L-A-NH₂ (SEQ. ID. NO.:214) | OK | OK |

TABLE 3-continued

Factor Xa Inhibitions having a Ki < 100 μM

| Structure | MS* | AA* |
|---|---|---|
| Ph-CH$_2$CH$_2$CH$_2$—CO-I-R-L-A-NH$_2$ (SEQ. ID. NO.:215) | OK | OK |
| Ph-CH$_2$CH$_2$CO-I-R-L-A-NH$_2$ (SEQ. ID. NO.:216) | OK | OK |
| Pth-Y-I-R-L-P-NH$_2$ (SEQ. ID. NO.:217) | OK | OK |
| S-Y-I-R-L-P-NH$_2$ (SEQ. ID. NO.:218) | OK | OK |
| Tfa-(iBu)F(pNH2)-Chg-R-NH$_2$ | OK | OK |
| Tfa-(iBu)F(pNH$_2$)-Chg-R-L-P-NH$_2$ (SEQ. ID. NO.:219) | OK | OK |
| Tfa-(iBu)Nal(2)-Chg-R-L-P-NH$_2$ (SEQ. ID. NO.:220) | OK | OK |
| Tfa-(iBu)Y-Chg-R-NH$_2$ | OK | OK |
| Tfa-(iBu)Y-Chg-R-L-P-NH$_2$ (SEQ. ID. NO.:221) | OK | OK |
| Tfa-(iBu)Y-I-Dab(N$^\gamma$-C$_3$H$_7$N)-L-P-NH$_2$ (SEQ. ID. NO.:222) | OK | OK |
| Tfa-(iBu)Y-I-Orn(N$^6$—C$_3$H$_7$N)-L-P-NH$_2$ (SEQ. ID. NO.:223) | OK | OK |
| Tfa-(iBu)Y-I-PalMe(3)-NH$_3$ | OK | OK |
| Tfa-(iBu)Y-I-R-NH$_2$ | OK | OK |
| Tfa-(iBu)Y-I-R-OH | OK | OK |
| Tfa-(iBu)Y-I-R-G-NH$_2$ (SEQ. ID. NO.:224) | OK | OK |
| Tfa-(iBu)Y-I-R-L-P-NH$_2$ (SEQ. ID. NO.:225) | OK | OK |
| Tfa-(Me)Y-I-R-L-A-NH$_2$ (SEQ. ID. NO.:226) | OK | OK |
| Tfa-Y(Me)I-R-L-P-NH$_2$ (SEQ. ID. NO.:227) | OK | OK |
| Tfa-Y-Chg-R-NH$_2$ | OK | OK |
| Tfa-Y-Chg-R-L-P-NH$_2$ (SEQ. ID. NO.:228) | OK | OK |
| Tfa-y-I-R-L-P-NH$_2$ | OK | OK |
| Tfa-I-R-L-P-NH$_2$ (SEQ. ID. NO.:229) | OK | OK |
| T-F-G-Y-I-R-K-A-NH$_2$ (SEQ. ID. NO.:230) | OK | OK |
| Tos-Y-I-R-NH$_2$ | OK | OK |
| Tos-G-I-R-V-Sar-NH$_2$ (SEQ. ID. NO.:231) | OK | OK |
| Tyr(Me)-I-R-L-A-NH$_2$ (SEQ. ID. NO.:232) | OK | OK |
| W-F-R-E-M-G-G-G-G-NH$_2$ (SEQ. ID. NO.:233) | OK | OK |
| W-I-R-E-K-NH$_2$ (SEQ. ID. NO.:234) | OK | OK |
| W-I-R-N-P-NH$_2$ (SEQ. ID. NO.:235) | OK | OK |
| W-I-R-T-P-NH$_2$ (SEQ. ID. NO.:236) | OK | OK |
| w-L-R-L-A-NH$_2$ | OK | OK |
| W-L-R-L-A-NH$_2$ (SEQ. ID. NO.:237) | OK | OK |
| W-L-R-L-A-G-G-G-G-G-NH$_2$ (SEQ. ID. NO.:238) | OK | OK |
| W-L-R-V-A-NH$_2$ (SEQ. ID. NO.:239) | OK | OK |
| w-L-R-V-A-NH$_2$ | OK | OK |
| W-L-R-V-A-G-G-G-G-NH$_2$ (SEQ. ID. NO.:240) | OK | OK |
| y(Me)-I-R-L-P-NH$_2$ | OK | OK |
| y-Chg-R-NH$_2$ | OK | OK |
| y-Chg-R-L-NH$_2$ | OK | OK |
| y-Chg-R-L-P-NH$_2$ | OK | OK |
| y-Tle-R-Nle-P-NH$_2$ | OK | OK |
| y-Tle-R-Nle-$\Delta^2$P-NH$_2$ | OK | OK |
| Y-I-(nR)-L-A-NH$_2$ | OK | OK |
| y-I-R(COCH2)-G-P-NH$_2$ | OK | OK |
| y-I-R-NH$_2$ | OK | OK |
| Y-I-R-NH$_2$ | OK | OK |
| Y-I-R-E-F-S-D-Y-NH$_2$ (SEQ. ID. NO.:241) | OK | OK |
| Y-I-R-G-A-NH$_2$ (SEQ. ID. NO.:242) | OK | OK |
| Y-I-R-I-NH$_2$ (SEQ. ID. NO.:243) | OK | OK |
| Y-I-R-I-Y-NH$_2$ (SEQ. ID. NO.:244) | OK | OK |
| Y-I-R-I-Y-E-R-E-NH$_2$ (SEQ. ID. NO.:245) | OK | OK |
| Y-I-R-L-NH$_2$ (SEQ. ID. NO.:246) | OK | OK |
| y-I-R-L-A-NH$_2$ | OK | OK |
| Y-I-R-L-a-NH$_2$ | OK | OK |
| Y-I-R-L-A-NH$_2$ (SEQ. ID. NO.:247) | OK | OK |
| Y-I-R-L-A-A-NH$_2$ (SEQ. ID. NO.:248) | OK | OK |
| Y-I-R-L-A-A-F-NH$_2$ (SEQ. ID. NO.:249) | OK | OK |
| Y-I-R-L-A-A-F-T-NH$_2$ (SEQ. ID. NO.:250) | OK | OK |
| Y-I-R-L-M-E-M-T-NH$_2$ (SEQ. ID. NO.:251) | OK | OK |
| y-I-R-L-P-NH$_2$ | OK | OK |
| Y-I-R-L-P-NH$_2$ (SEQ. ID. NO.:252) | OK | OK |
| Y-I-R-L-P-G-L-L-NH$_2$ (SEQ. ID. NO.:253) | OK | OK |
| Y-I-R-L-T-K-M-W-NH$_2$ (SEQ. ID. NO.:254) | OK | OK |
| Y-I-R-V-A-Q-L-Y-NH$_2$ (SEQ. ID. NO.:255) | OK | OK |
| Y-I-R-V-M-N-H-R-NH$_2$ (SEQ. ID. NO.:256) | OK | OK |
| Y-I-R-Y-R-N-P-I-NH$_2$ (SEQ. ID. NO.:257) | OK | OK |
| Y-R-Y-P-R-D-R-N-NH$_2$ (SEQ. ID. NO.:258) | OK | OK |
| Y-L-R-F-P-NH$_2$ (SEQ. ID. NO.:259) | OK | OK |

*MS, mass spectrometry; AA, amino acid analysis.
**underlining indicates cyclized portion of peptide.

EXAMPLE XXXVII

In vitro inhibition of selected purified coagulation enzymes and other serine proteases The ability of a compound of the invention to inhibit factor Xa, thrombin, plasmin, elastase and trypsin was assessed by determining the concentration of YIR peptide that inhibits enzyme activity by 50% (IC$_{50}$). Purified enzymes were used in chromogenic assays. To determine the inhibition constant, the IC$_{50}$ value was corrected for competition with substrate using the formula:

$$Ki = IC_{50} \times (1/\{1 + ((\text{substrate concentration})/\text{substrate Km})\})$$

(Chen and Prusoff, *Biochem. Pharmacol.* 22:3099–3018 (1973), which is incorporated herein by reference).

a. Factor Xa assay

TBS-P buffer (50 mM Tris-Cl, pH 7.8, 200 mM NaCl, 0.05% (w/v) PEG-8000, 0.02% (w/v) NaN$_3$) was used for this assay. The IC$_{50}$ was determined by combining in appropriate wells of a Costar half-area microtiter plate 25 μl human factor Xa (Enzyme Research Laboratories, Inc.; South Bend IN) in TBS-P; 40 μl 10% (v/v) DMSO in TBS-P (uninhibited control) or various concentrations of a peptide to be tested diluted in 10% (v/v) DMSO in TBS-P; and substrate S-2765 (Nα-benzyloxycarbonyl-D-Arg-Gly-L-Arg-p-nitroanilide; Kabi Pharmacia, Inc.; Franklin Ohio) in TBS-P.

The assays were performed by pre-incubating the peptide inhibitor plus enzyme for 10 min, then the assay was initiated by adding substrate to obtain a final volume of 100 μl. The initial velocity of chromogenic substrate hydrolysis was measured by the change in absorbance at 405 nM using a Bio-tek Instruments kinetic plate reader (Ceres UV900HDi) at 25° C. during the linear portion of the time course (usually 1–5 min after addition of substrate). The concentration of inhibitor that caused a 50% decrease in the rate of substrate hydrolysis was predicted by linear regression after plotting the relative rates of hydrolysis (compared to the uninhibited control) versus the log of the peptide concentration. The enzyme concentration was 0.5 nM and substrate concentration was 140 μM.

b. Thrombin assay

TBS-P buffer was used for this assay. The IC$_{50}$ was determined as described in Example XXXVII.a., except that the substrate was S-2366 (L-PyroGlu-L-Pro-L-Arg-p-nitroanilide; Kabi) and the enzyme was human thrombin (Enzyme Research Laboratories, Inc.; South Bend Ind.). The enzyme concentration was 1 nM and substrate concentration was 175 μM.

c. Plasmin assay

TBS-P buffer was used for this assay. The IC$_{50}$ was determined as described in Example XXXVII.a., except that the substrate was S-2251 ((D)-Val-L-Leu-L-Lys-p-nitroanilide; Kabi) and the enzyme was human plasmin (Kabi). The enzyme concentration was 5 nM and the substrate concentration was 300 uM.

d. Trypsin assay

TBS-P buffer containing 10 mM CaCl2 was used for this assay. The IC$_{50}$ determination was determined as described in Example XXXVII.a., except that the substrate was BAPNA (Benzoyl-L-Arg-p-nitroanilide; Sigma Chemical Co.; St. Louis, Mo.) and the enzyme was bovine pancreatic trypsin (Type XIII, TPCK treated; Sigma). The enzyme concentration was 50 nM and the substrate concentration was 300 μM.

e. Elastase assay

Tris-Cl, pH 7.4, 300 mM NaCl, 2% (v/v) N-methyl-pyrrolidone, 0.01% (w/v) NaN3 buffer was used for this assay. The $IC_{50}$ was determined as described in Example XXXVII.a., except that the substrate was succinyl-Ala-Ala-Ala-p-nitroanilide (Calbiochem-Nova Biochem Corp.; San Diego, Calif.) and the enzyme was human neutrophil elastase (Athens Research and Technology, Inc.; Athens, Ga.). The enzyme concentration was 75 nM and the substrate concentration was 600 $\mu$M.

The Ki values for selected test compounds compared to the control compound "TENSTOP" (N-alpha-tosyl-Gly-p-amidinophenylalanine methyl ester; American Diagnostica, Inc.; Greenwich, Conn.), which is a reversible factor Xa inhibitor (Sturzebecher et al., *Thromb. Res.* 54:245–252 (1989); Hauptmann et al., *Thromb. Haem.* 63:220–223 (1990), each of which is incorporated herein by reference) are shown in Table 2, above. The results demonstrate that the YIR peptides of the invention can inhibit factor Xa activity but do not substantially inhibit the activity of various other serine proteases, including thrombin and plasmin, which are involved in the process of blood coagulation and fibrinolysis.

EXAMPLE XXXVIII

Assays for determining inhibition of coagulation

The compounds of the invention were assessed for their ability to inhibit factor Xa activity. Effectiveness of various compounds was assessed by the in vitro prothrombin time (PT) assay using pooled human donor plasma. An ex vivo assay also was used in which plasma was collected at various times after intravenous (iv) administration of a compound to rats and to rabbits or intraduodenal administration to rats and analyzed using the PT assay to determine plasma half-life. The PT assay was initiated with a thromboplastin dilution selected to obtain an extended and highly reproducible coagulation endpoint, referred to as the "dilute PT assay" as described below. Effectiveness of various compounds also was determined using an in vivo rat arteriovenous shunt model of thrombosis.

a. In Vitro Dilute Prothrombin Time Assay

100 $\mu$l prewarmed (37° C.) pooled human platelet poor plasma (PPP) was added to a fibrometer cup (Baxter Diagnostics., Inc.; McGaw Park Ill. 50 $\mu$l of various concentrations of a test compound in TBS-BSA with calcium (50 mM Tris-Cl, 100 mM NaCl, 0.1% (w/v) bovine serum albumin, 20 mm $CaCl_2$) was added. In control experiments, TBS-BSA with calcium but without test compound was added for measurement of uninhibited coagulation time. 150 $\mu$l diluted prewarmed rabbit thromboplastin (Baxter) with calcium was added to the fibrometer cup and the fibrometer timer is started. A rabbit thromboplastin dilution curve was obtained prior to testing the compound and is used to choose a thromboplastin dilution that allows approximately 30 sec PT time for uninhibited controls. The experimental concentration giving 50% inhibition of coagulation ($EC_{50}$) with test compound (see Table 4, below) was calculated from the dilution curve times.

Alternatively, the dilute prothrombin time assay was conducted using the "research" mode on an Instrumentation Laboratories (IL) ACL3000-plus automated coagulation instrument (IL; Milan, Italy). Thromboplastin was diluted until a clotting time of 30–35 seconds was achieved. This clotting time was taken as 100% activity. A standard curve for calibration was established by serial 2-fold dilution of the diluted thromboplastin reagent (rabbit brain IL-brand thromboplastin). During the assay, a 50 $\mu$l sample (plasma separated by centrifugation) was mixed with 100 $\mu$l thromboplastin reagent and nephelometric readings were taken over 169 sec. Coagulation time was determined from the maximal rate of change of light scatter calculated by the instrument. Inhibition is expressed as percent activity as determined by comparison with the calibration curve.

b. Ex Vivo Dilute Prothrombin Time Assay

Test compound was administered iv either through the tail vein (rat) or ear vein (rabbit) following an approved protocol. One ml blood samples were removed at timed intervals after administration of a test compound from a cannulated carotid artery (rat) or auricular artery (rabbit). After centrifugation to obtain PPP, the plasma was immediately stored on ice or frozen.

For dilute prothrombin time determination, the plasma was prewarmed and assayed as described above. Percent inhibition was calculated from a thromboplastin dilution curve, which was run with each series of samples, and used to determine the time at which approximately 50% of the initial anticoagulant activity remains in the plasma (T½). The results of this experiment demonstrate that the YIR peptides of the invention can inhibit blood coagulation in in vitro and after administration in vivo (see Table 4).

TABLE 4

Activities and half-lives of selected inhibitors

| Structure | $EC_{50}$ Pooled Human in vitro | $T_{1/2}$ Rat ex vivo | $T_{1/2}$ Rabbit ex vivo |
|---|---|---|---|
| AC-Y-Chg-R-NH$_2$ | 2.5 $\mu$M | 5 min | 5 min |
| AC-Y-Chg-R-L-P-NH$_2$ | 225 nM | 5 min | 5 min |
| Ac-Nal(2)-Chg-R-L-P-NH$_2$ | 140 nM | 6 min | 5 min |
| Tfa-(iBu)Y-Chg-R-L-P-NH$_2$ | 300 nM | 15 min | 10 min |

Various compounds also were examined for anticoagulant activity using the ex vivo dilute prothrombin time assay following iv bolus administration of various doses in rats. The compounds listed in Table 5 demonstrated at least 30% inhibition 10 min after administration of ≦2 mg/kg of the indicated compound. These results demonstrate that various representative YIR peptides of the invention have substantial anticoagulant activity. The structures of all of the compounds listed in Table 5 were confirmed by MS and AA.

TABLE 5

1. Ac-pAph-Chg-PalMe(3)-NH—CH$_2$-Chx
2. Ac-pAph-Chg-PalMe(3)-NH-2CMT
3. Ac-pAph-Chg-PalMe(3)-NH-Chx
4. Ac-F(pNH$_2$)-Chg-Dab(N$^\gamma$-C$_3$NH$_7$)L-P-NH$_2$ (SEQ. ID. NO.:263)
5. Bz-F(pNH$_2$)-Chg-R-L-P-NH$_2$ (SEQ. ID. NO.:264)
6. Tos-F(pNH$_2$)-Chg-R-L-P-NH$_2$ (SEQ. ID. NO.:265)
7. Ac-Y(3-I)-Chg-R-L-P-NH$_2$(SEQ. ID. NO.:266)
8. Ac-pAph-Chg-AMP(4)
9. y-Chg-R-L-NH$_2$
10. Ac-F(pNH$_2$)-Chg-R-ol
11. Cyclopentyl-CO-pAph-Chg-PalMe(3)-NH$_2$
12. 3-Iqc-pAph-Chg-PalMe(3)-NH$_2$
13. Bzf-pAph-Chg-PalMe(3)-NH$_2$
14. 3-Iqc-F(pNH$_2$)-Chg-R-L-P-NH$_2$ (SEQ. ID. NO.:267)
15. Ac-F(pNH$_2$)-Chg-R-Thiazolyl
16. 2-Furoyl-pAph-Chg-PalMe(3)-NH$_2$
17. 5-Me-thienyl-CO-pAph-Chg-PalMe(3)-NH$_2$
18. Ac-Nal(2)-Chg-R-Thiazolyl
19. 2-Bzf-f(pNH$_2$)-Chg-R-L-P-NH$_2$
20. Ac-pAph-Chg-Dab(N$^\gamma$-C$_3$NH$_7$)-L-P-NH$_2$ (SEQ. ID. NO.:268)
21. Ac-Orn-(Nal(2)-Chg-PalMe(3)-Sar-E-NH$_2$ (SEQ. ID. NO.:269)

TABLE 5-continued

22. Ac-Phe(3-I,4-NH$_2$)-Chg-R-L-P-NH$_2$ (SEQ. ID. NO.:270)
23. Ac-(iBu)pAph-Chg-R-L-P-NH$_2$ (SEQ. ID. NO.:271)
24. Ac-pAph-Chg-R-Gla-P-NH$_2$ (SEQ. ID. NO.:272)
25. Ac-pAph-Chg-R-Pen(CH$_2$COOH)-P-NH$_2$ (SEQ. ID. NO.:273)
26. Ac-pAph-Chg-R-L-P-NH$_2$ (SEQ. ID. NO.:274)
27. Ac-F(pNH$_2$)-Chg-R-(Me)L-P-NH$_2$ (SEQ. ID. NO.:275)
28. Ac-F(pNH$_2$)-Chg-R-OEt
29. Ac-F(pNH$_2$)-Chg-Orn(N$^6$-C$_3$H$_7$N)-L-P-NH$_2$ (SEQ. ID. NO.:276)
30. Ac-F(pNH$_2$)-Chg-R-L-P-NH$_2$ (SEQ. ID. NO.:277)
31. Ac-Nal(2)-Chg-R-L-P-NH$_2$ (SEQ. ID. NO.:278)
32. Ac-pAph-Chg-Dab(N$^\gamma$-C$_3$H$_7$N)
33. Ac-pAph-Chg-PalMe(3)-NH$_2$
34. Ac-pAph-Chg-PalMe(3)-L-P-NH$_2$ (SEQ. ID. NO.:279)
35. Ac-pAph-Chg-R-NH$_2$
36. Ac-pAph-Chg-R-OH
37. Ac-Y-Chg-R-NH-Nip-NH$_2$
38. Ac-<u>K-Nal(2)-Chg-R-Hyp-E</u>-NH$_2$ (SEQ. ID. NO.:280)
39. DIPA-pAph-Chg-R-L-P-NH$_2$ (SEQ. ID. NO.:281)
40. DIPA-mF(pNH$_2$)-Chg-R-L-P-NH$_2$ (SEQ. ID. NO.:289)
41. Isn-F(pNH$_2$)-Chg-R-L-P-NH$_2$ (SEQ. ID. NO.:282)
42. Pza-F(pNH$_2$)-Chg-R-L-P-NH$_2$ (SEQ. ID. NO.:283)
43. Tfa-(iBu)F(pNH$_2$)-Chg-R-L-P-NH$_2$ (SEQ. ID. NO.:284)
44. Tfa-(iBu)Y-Chg-R-L-P-NH$_2$ (SEQ. ID. NO.:285)
45. Tfa-(iBu)Y-I-Orn(N$^6$-C$_3$H$_7$N)-L-P-NH$_2$ (SEQ. ID. NO.:286)

*underlining indicates cyclic portion of compound.

In some experiments, the test compounds were administered to rats using an intraduodenal dosing protocol. Male Sprague-Dawley rats weighing approximately 300 g were anesthetized with a combination of ketamine/xylazine, subcutaneously, following an approved protocol. The right carotid artery was cannulated for blood sampling. A laparotomy was performed and duodenum was cannulated with a ball-tip needle and tied into place to ensure that the suture was distal to the point of insertion. An additional tie was placed proximal to the insertion point to prevent leakage of gastric contents. The effectiveness of the suture in preventing a compound from reaching the site of insertion was tested by pressure testing at the conclusion of each experiment. The point of insertion was approximately 4 cm from the duodenal-gastric junction. Compounds were administered in 1 ml normal saline. A 0.7 ml blood sample was drawn prior to administration of the test compound and at 15, 30, 60, 90 and 120 min after administration. Plasma was separated by centrifugation and assayed for inhibition of coagulation using the dilute prothrombin time assay.

The following compounds showed at least 30% inhibition in the dilute prothrombin time assay following intraduodenal administration of ≦50 mg/kg compound: Ac-pAph-Chg-PalMe(3)—NH—CH$_2$-Chx; Ac-pAph-Chg-PalMe(3)—NH—Chx; Bzf-pAph-Chg-PalMe(3)—NH$_2$; Ac-F(pNH$_2$)-Chg—R-L-P—NH$_2$; Ac-pAph-Chg-PalMe(3)-L-P—NH$_2$; Ac-pAph-Chg-PalMe(3)—NH$_2$; Ac-Aph-Chg-AMP(4); Cyclopentyl-CO-pAph-Chg-PalMe(3)—NH$_2$; 3-Iqc-pAph-Chg-PalMe(3)—NH$_2$; 2-Furoyl-pAph-Chg-PalMe(3)—NH$_2$; 5-Me-thienyl-CO-pAph-Chg-PalMe(3 —NH2, Ac-Y(3-I)-Chg-R-L-P—NH$_2$, Ac-F(pNH$_2$)-Chg-R-ol and Ac-pAph-Chg-PalMe(3)-ol.

c. Rat Arteriovenous Shunt Model of Thrombosis

The anti-thrombotic efficacy of various compounds of the invention was assessed using rat extracorporeal arteriovenous (AV) shunt. The AV shunt circuit consisted of a 20 cm length of polyethylene (PE) 60 tubing inserted into the right carotid artery, a 6 cm length of PE 160 tubing containing a 6.5 cm length of mercerized cotton thread (5 cm exposed to blood flow), and a second length of PE 60 tubing (20 cm) completing the circuit into the left jugular vein. The entire circuit was filled with normal saline prior to insertion.

Test compounds were administered by continuous infusion into the tail vein using a syringe pump and butterfly catheter (infusion volume 1.02 ml/hr). A compound was administered for 30 min, then the shunt was opened and blood was allowed to flow for a period of 15 min (total of 45 min infusion). At the end of the 15 min period, the shunt was clamped and the thread was carefully removed and weighed on an analytical balance. Percent inhibition of thrombus formation was calculated using the thrombus weight obtained from control rats, which were infused with saline.

The following compounds inhibited thrombus growth by at least about 30% following an infusion of ≦33 μg/kg/min: Ac-pAph-Chg-PalMe(3)—NH—CH$_2$-Chx; Ac-pAph-Chg-PalMe(3)—NH-Chx; Bzf-pAph-Chg-PalMe(3)—NH$_2$; Ac-pAph-Chg-PalMe(3)-L-P—NH$_2$; Ac-pAph-Chg-PalMe(3)—NH$_2$; Ac-pAph-Chg-AMP(4); Cyciopentyl-CO-pAph-Chg-PalMe(3)—NH$_2$; 3-Iqc-pAph-Chg-PalMe(3)—NH$_2$; 2-Furoyl-pAph-Chg-PalMe(3)—NH$_2$; 5-Me-thienyl-CO-pAph-Chg-PalMe(3)—NH$_2$, Ac-pAph-Chg-PalMe(3)-ol and Tos-F(pNH$_2$)-Chg-R-L-P—NH$_2$.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

We claim:

1. A compound that specifically inhibits the activity of factor Xa, having the general formula A1-A2-(A3)$_m$-B, wherein m is 0 or 1;

wherein A1 is R$_1$—R$_2$—R$_3$; A2 is R$_4$—R$_5$—R$_6$; A3 is R$_7$—R$_8$—R$_9$;

wherein R$_1$ is selected from the group consisting of:

i) 1 to 20 amino acids;

ii)
$$R'_1-\overset{\overset{\displaystyle O}{\|}}{C}-$$

and
iii)

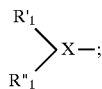

wherein X is selected from the group consisting of N, CH and NC=O, and
wherein R'₁ and R"₁ independently are selected from the group consisting of H, alkyl, acyl, aryl, arylalkyl and an amino-protecting group, and
wherein R₁ can be substituted by a substituent;

R₂ is —CR₉₉R₁₀₀—, wherein R₉₉ and R₁₀₀ independently are selected from the group consisting of an H; alkyl, arylalkyl, heteroarylalkyl and heteroaryl, and wherein R₉₉ and R₁₀₀ independently can be substituted with a substituent;

R₃ is selected from the group consisting of —C(O)—, —CH₂—, —CHR₉₉—C(O)— and —C(O)—NR₃₅—CH₂—C(O)—, wherein R₃₅ is the CHR₅₅ group of the bridging group —C(O)—CR₅₅—;

R₄ is selected from the group consisting of —CH₂— and —NR₅₀—, wherein R₅₀ is selected from the group consisting of H, alkyl, arylalkyl and heterocyclic;

R₅ is —CR₂₀₁R₂₀₂—, wherein R₂₀₁ and R₂₀₂ independently are selected from the group consisting of H, alkyl, aryl and arylalkyl, and wherein R₂₀₁ and R₂₀₂ independently can be substituted with a substituent;

R₆ is selected from the group consisting of —C(O)—, —CH₂— and —CHR₉₉—C(O)—;

R₇ is selected from the group consisting of —CH₂— and —NR₅₁—, wherein R₅₁ is H, alkyl, arylalkyl, heteroalkyl and heteroarylalkyl, and any of these moieties substituted by a substituent selected from the group consisting of Q and —(CH₂)ₙ—Q, wherein n is 1 to 5 and wherein Q is selected from the group consisting of an amino, amidino, imidazole and guanidino group, which can be substituted with a substituent, and a mono-, di-, tri- or tetra-alkylammonium of a pharmaceutically acceptable salt, isoureide or isothioureide thereof;

R₈ is —CR₂₁₀R₂₁₁—, wherein R₂₁₀ and R₂₁₁ independently are selected from the group consisting of H, alkyl, alkylaryl and heterocyclic, and any of these moieties substituted by a substituent selected from the group consisting of Q and —(CH₂)ₙ—Q, wherein n is 1 to 5 and wherein Q is selected from the group consisting of amino, amidino, imidazole and guanidino group, which can be substituted with a substituent, and a mono-, di-, tri- or tetra-alkylammonium of a pharmaceutically acceptable salt, isoureide or isothioureide thereof;

R₉ is selected from the group consisting of —C(O)—, —CH₂— and —CHR₉₉—C(O)—; and wherein, when m is 1, B is selected from the group consisting of 1 to 20 amino acids, —NHR₅₂, —NR₆₀R₆₁, —OR₇₀ and —CHR₆₀R₆₁,
wherein R₅₂ is selected from the group consisting of H, alkyl, arylalkyl, heteroarylalkyl and heteroaryl;
wherein R₆₀ and R₆₁ independently are selected from the group consisting of H, alkyl, arylalkyl, aryl, heteroarylalkyl and heteroaryl, and
wherein R₇₀ is selected from the group consisting of H, acyl, alkyl, arylalkyl and heteroarylalkyl, and wherein when m is 0, B is selected from the group consisting of 1 to 20 amino acids, —OR₇₀, —NHR₅₂ and —NR₆₀R₆₁, which is joined to R₆ by an amide bond or an ester bond;

wherein B can be substituted with a substituent, provided that when R₃ is —CH₂— or —CHR₉₉—C(O)—, R₄ is NR₅₀;
when R₄ is —CH₂—, R₃ is —C(O)— or —CHR₉₉—C(O)—;
when R₄ is —CH₂—, R₃ is —C(O)— or —CHR₉₉—C(O)—;
when R₆ is —CH₂—, R₇ is —NHR₅₁—;
when R₇ is CH₂, R₆ is —C(O)— or —CHR₉₉—C(O)—;
when R₄ is —NR₅₀— and R₁ is

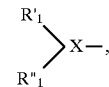

R₅₀ and R'₁ are taken together to form a bridging group having the formula: —C(O)—CHR₅₅—,
wherein CHR₅₅ represents R₅₀ and the carbonyl group represents R'₁, and
R"₁ and R₅₅ independently are H, C₁ to C₆ alkyl or arylalkyl; and
when R₃ is —C(O)—NR₃₅—CH₂—C(O)—, then R₄ is —NR₅₀—, R₁ is

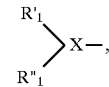

R₃₅ and R'₁ are taken together to form a bridging group having the formula —C(O)CHR₅₅—,
wherein C(O) represents R'₁ and CHR₅₅ represents R₃₅;
R"₁ and R₅₅ independently are H or a C₁ to C₆ alkyl.

2. The compound of claim 1, wherein
R₄ is —NR₅₀—,
R₁ is

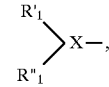

R₅₀ and R'₁ are taken together to form a bridging group of the formula —C(O)—CHR₅₅,
wherein R₅₅ is H;
R₁ is H or methyl;
R₉₉ and R₁₀₀ independently are selected from the group consisting of H, arylalkyl, alkyl and heteroalkyl or 1 to 3 carbon atoms,
and wherein R₉₉ and R₁₀₀ can be further linked to a moiety selected from the group consisting of phenyl, thienyl, thiazolyl, pyridyl, naphthyl, thionaphthyl, indolyl or saturated alkyl, alkoxy, monoalkylamino, dialkylamino, tetraalkylammonium, arylalkylamino, aminoalkylaryl, carboxy, halo, hydroxy, amino, amido, amidino, guanidino, triazolyl and sulfonyl,
and R₃ is selected from the group consisting of —C(O)— and —C(O)—NR₃₅—CH₂—C(O)—.

3. The compound of claim 1, further comprising a bridge formed between two moieties selected from the group consisting of $R_{10}$ and $R_1$, $R_9$ and $R_1$, $R_8$ and $R_1$, $R_5$ and $R_1$, $R_5$ and $R_2$, $R_5$ and $R_8$, and $R_5$ and $R_9$, wherein said bridge structure consists of the structure —$CR_{400}R_{410}$ (X—Y)—$R_{500}R_{510}C$—; wherein $R_{400}$, $R_{410}$, $R_{500}$ and $R_{510}$ are selected from the group consisting of H, alkyl, cycloalkyl, arylalkyl and aryl, and X and Y independently are selected from the group consisting of carbon, nitrogen, oxygen, sulfur, —CO—NH—, —$CH_2$—O—$CH_2$, and functional equivalents thereof;

and wherein $R_{400}$, $R_{410}$, $R_{500}$, $R_{510}$ can be substituted with a moiety selected from the group consisting of an alkyl group and a heteroatom.

4. The compound of claim 1, wherein R'1 and R"1 independently are substituted by a substituent selected from the group consisting of a $C_1$–$C_6$ alkyl, —$OCH_2$—, —$SCH_2$—, >N—$CH_2$—, >N—C(O)—, —CO— and NY—CO—NZ, wherein Y and Z independently are selected from the group consisting of H, $C_1$–$C_8$ alkyl, $C_5$–$C_{12}$ arylalkyl and heteroarylalkyl.

5. The compound of claim 1, wherein $R_2$ is substituted by a substituent selected from the group consisting of phenyl, thienyl, thiazolyl, pyridyl, naphthyl, thionaphthyl, indolyl, alkyl, alkoxy, monoalkylamine, dialkylamine, tetraalkylammonium, arylalkylamino, aminoalkylaryl and carboxy.

6. The compound of claim 5, wherein $R_2$ is substituted with 1 to 5 substituents selected from the group consisting of alkyl, alkoxy, monoalkylamino, dialkylamino, tetraalkylammonium, arylalkylamino, aminoalkylaryl, carboxy, halogens, hydroxy, amino, amido, amidino, guanidino, triazolyl and sulfonyl.

7. The compound of claim 1, wherein $R_{100}$ is H and $R_{99}$ is selected from the group consisting of:

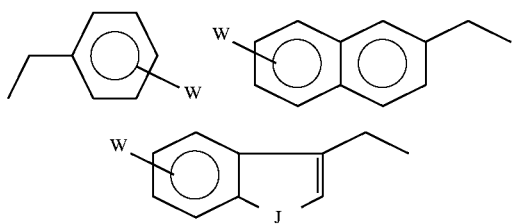

wherein W is selected from the group consisting of H, amino, lower alkyl, optionally substituted by an amine, amide, hydroxyl, carboxyl and amidino;

and J is selected from the group consisting of oxygen, sulfur, NH and NR, wherein R is selected from the group consisting of $C_1$–$C_6$ alkyl, $C_5$–$C_{12}$ arylalkyl, $C_1$–$C_6$ alkanoyl and $C_5$–$C_{12}$ aryloyl.

8. The compound of claim 1, wherein $R_{50}$ is substituted by a substituent selected from the group consisting of an N-, O- and S-containing moiety.

9. The compound of claim 1, wherein $R_{50}$ is selected from the group consisting of H, alkyl, arylalkyl and heteroarylalkyl.

10. The compound of claim 1, wherein $R_{201}$ and $R_{202}$ further is substituted by a substituent selected from the group consisting of an N-, O- and S-containing moiety.

11. The compound of claim 1, wherein $R_{202}$ is H and $R_{201}$ is selected from the group consisting of

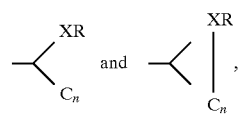

wherein X is C, N or S, and wherein R is selected from the group consisting of H and an alkyl, which can be substituted by a heteroatom; and n is 1 to 5.

12. The compound of claim 1, wherein $R_{51}$ is substituted by a substituent selected from the group consisting of a N-, O- and S-containing moiety.

13. The compound in claim 1, wherein $R_{210}$ or $R_{211}$ is substituted with a substituent selected from the group consisting of Q and $(CH_2)_n$—Q, wherein n is 1 to 5.

14. The compound of claim 1, wherein $R_{52}$ is substituted by a substituent selected from the group consisting of a N-, O- and S-containing moiety.

15. The compound of claim 1, wherein $R_{60}$ and $R_{61}$ independently are substituted by an alkyl.

16. The compound of claim 1, wherein $R_{70}$ is substituted by an alkyl.

17. The compound of claim 1, wherein:

$R_1$ is

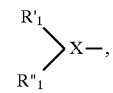

$R'_1$ is selected from the group consisting of H, —CO—$R_a$, —$SO_2$—$R_a$, an amino-protecting group, 1 to 6 amino acids, which can be substituted, wherein the N-terminus of said 1 to 6 amino acids is substituted with a substituent selected from the group consisting of H, —CO—$R_a$, —$SO_2$—$R_a$ and an amino-protecting group; and wherein $R_a$ is selected from the group consisting of alkyl, aryl and heteroalkyl;

$R"_1$ is selected from the group consisting of H, acyl and alkyl;

X is N;

$R_2$ is —$CHR_{99}$—, wherein $R_{99}$ is selected from the group consisting of alkyl, aryl, arylalkyl, heteroalkyl and heteroaryl, which can be substituted with a substituent selected from the group consisting of 1 to 6 fluoro, chloro, bromo, iodo, amino, nitro, amidino, amido, carboxy, ester, ether and hydroxy groups;

$R_3$ is —C(O)—;

$R_4$ is —NH—;

$R_5$ is —$CHR_{201}$—, wherein $R_{201}$ is an alkyl;

$R_6$ is —C(O)—;

$R_7$ is —NH—;

$R_8$ is —$CHR_{210}$—, wherein $R_{210}$ is a heteroalkyl having at least one formal positive charge, wherein the heteroatom is N;

$R_9$ is —C(O)—; and

B is selected from the group consisting of —$OR_b$ and —N—$R_cR_d$, wherein $R_b$ is selected from the group consisting of H, alkyl and a carboxy-protecting group, $R_c$ is selected from the group consisting of H and alkyl, and $R_d$ is selected from the group consisting of alkyl, heteroalkyl and 1 to 20 amino acids, which can be substituted with a substituent, wherein the C-terminus of said compound can be modified with a carboxy-protecting group, a primary amide group or part of a cyclic peptide as the secondary or tertiary amide group formed with amino group of $R_1$.

18. The compound of claim 17, wherein A1 is selected from the group consisting of Tyr, F(pNH$_2$) mAph, pAph and Nal(2).

19. The compound of claim 17, which contains an amino-protecting group.

20. The compound of claim 17, wherein A2 is selected from the group consisting of Ile and Chg.

21. The compound of claim 17, wherein A3 is selected from the group consisting of Arg, PalMe(3), Dab(N$^\gamma$—C$_3$H$_7$N), Dap(N$^\beta$—C$_3$H$_7$N) and Orn(N$^\delta$—C$_3$H$_7$N).

22. The compound of claim 17, wherein
A1 is selected from the group consisting of Tyr, F(pNH$_2$), mAph, pAph and Nal(2), which contain 0 or 1 amino-protecting groups;
A2 is selected from the group consisting of Ile and Chg;
A3 is selected from the group consisting of Arg, PalMe (3), Dab(N$^\gamma$—C$_3$H$_7$N), Dap(N$^\beta$—C$_3$H$_7$N) and Orn (N$^\delta$—C$_3$H$_7$N); and
B is selected from the group consisting of —H, —OH, —NH$_2$, one to five amino acids or functional equivalents thereof and a carboxy-protecting group.

23. The compound of claim 22, which is selected from the group consisting of:
Ac-pAph-Chg-PalMe(3)—NH—CH$_2$-Chx;
Ac-pAph-Chg-PalMe(3)—NH-2CMT;
Ac-pAph-Chg-PalMe(3)—Nh-Chx;
Ac-F(pNH2)-Chg-Dab(N$^\gamma$—C$_3$NH$_7$)-L-P—NH$_2$ (SEQ ID NO: 263);
Bz-F(pNH$_2$)-Chg-R-L-P—NH$_2$ (SEQ ID NO: 264);
Tos-F(pNH$_2$)-Chg-R-L-P—NH$_2$ (SEQ ID NO: 265);
Ac-Y(3-I)-Chg-R-L-P—NH$_2$ (SEQ ID NO: 266);
y-Chg-R-L—NH$_2$;
Ac-F (pNH$_2$)-Chg-R-ol;
Cyclopentyl-CO-pAph-Chg-PalMe(3)—NH$_2$;
3-Iqc-pAph-Chg-PalMe(3)—NH$_2$;
Bzf-pAph-Chg-PalMe(3)—NH$_2$;
3-Iqc-F(pNH$_2$)-Chg-R-L-P—NH$_2$ (SEQ ID NO: 267);
Ac-F(pNH$_2$)-Chg-R—NH-2-thiazolyl;
2-Furoyl-pAph-Chg-PalMe(3)—NH$_2$;
5-Me-2-thienyl-CO-pAph-Chg-PalMe(3)—NH$_2$;
Ac-Nal(2)-Chg-R—NH-2-thiazolyl;
2-Bzf-f(pNH$_2$)-Chg-R-L-P—NH$_2$;
Ac-pAph-Chg-Dab(N$^\gamma$—C$_3$NH$_7$)-L-P—NH$_2$ (SEQ ID NO: 268);
Ac-(iBu)pAph-Chg-R-L-P—NH$_2$ (SEQ ID NO: 271);
Ac-pAph-Chg-R-Gla-P—NH$_2$ (SEQ ID NO: 272);
Ac-pAph-Chg-R-Pen(CH$_2$COOH)-P—NH$_2$ (SEQ ID NO: 273);
Ac-pAph-Chg-R-L-P—NH$_2$ (SEQ ID NO: 274);
Ac-F(pNH$_2$)-Chg-R-(Me)L-P—NH$_2$ (SEQ ID NO: 275);
Ac-F(pNH$_2$)-Chg-R-OEt;
Ac-F(pNH$_2$)-Chg-Orn (N$^\delta$—C$_3$H$_7$N)-L-P—NH$_2$ (SEQ ID NO: 276);
Ac-F(pNH$_2$)-Chg-R-L-P—NH$_2$ (SEQ ID NO: 277);
Ac-Nal(2)-Chg-R-L-P—NH$_2$ (SEQ ID NO: 278);
Ac-pAph-Chg-Dab(N$^\gamma$—C$_3$H$_7$N)—NH$_2$;
Ac-pAph-Chg-PalMe(3)—NH$_2$;
Ac-pAph-Chg-PalMe(3)-L-P—NH$_2$ (SEQ ID NO: 279);
Ac-pAph-Chg-R—NH$_2$;
Ac-pAph-Chg-R—OH;
Ac-pAph-Chg-R-ol;
DIPA-(m)pAph-Chg-R-L-P—NH$_2$ (SEQ ID NO: 36);
DIPA-(m)F(pNH$_2$)-Chg-R-L-P—NH$_2$ (SEQ ID NO: 289);
Isn-F(pNH$_2$)-Chg-R-L-P—NH$_2$ (SEQ ID NO: 282);
Pza-F(pNH$_2$)-Chg-R-L-P—NH$_2$ (SEQ ID NO: 283);
Tfa-(iBu)Y-Chg-R-L-P—NH$_2$ (SEQ ID NO: 285); and
Tfa-(iBu)Y-I-Orn(N$^\delta$—C$_3$H$_7$N)-L-P—NH$_2$ (SEQ ID NO: 286).

24. The compound of claim 22, selected from the group consisting of:
Ac-pAph-Chg-PalMe (3)—NH—CH$_2$-Chx;
Ac-pAph-Chg-PalMe(3)—NH-Chx;
Bzf-pAph-Chg-PalMe(3)—NH$_2$;
Ac-pAph-Chg-PalMe(3)-L-P—NH$_2$ (SEQ ID NO: 279);
Ac-pAph-Chg-PalMe(3)—NH$_2$;
Cyclopentyl-CO-pAph-Chg-PalMe(3)—NH$_2$;
3-Iqc-pAph-Chg-PalMe(3)—NH$_2$;
2-Furoyl-pAph-Chg-PalMe(3)—NH$_2$;
5-Me-thienyl-CO-pAph-Chg-PalMe(3)—NH$_2$; and
Ac-pAph-Chg-PalMe(3)-ol.

25. The compound of claim 1, wherein m is 0.

26. The compound of claim 25, wherein B is a heteroarylalkyl.

27. The compound of claim 26, wherein said heteroarylalkyl is selected from the group consisting of:
(4-(N-methylpyridinium) )methyl;
2-(3-(N-methylpyridinium) )eth-1-yl;
1-(4-(N-methylpyridinium) )eth-1-yl;
(p-amidino)benzyl;
2-(4-(N-methylpyridinium) )prop-2-yl; and
2-(4-(N-methylpyridinium) )eth-1-yl.

28. The compound of claim 26, which is selected from the group consisting of:
Ac-pAph-Chg-AMP(4) and
Ac-pAph-Chg-AEMP(4).

29. A non-naturally occurring compound which specifically -inhibits factor Xa activity, having the structure $X_1$-YIR-$X_2$,
wherein $X_1$ is selected from the group consisting of H, acyl, alkyl, acylalkyl, arylalkyl and 1 to 20 YIR is the amino acid sequence tyrosine-isoleucine-arginine or a functional equivalent thereof, and
$X_2$ is selected from the group consisting of a modified C-terminal group, one or more carboxy-protecting groups and 1 to 20 amino acids,
wherein said compound can be substituted with a substituent.

30. The compound of claim 29, wherein $X_1$ is selected from the group consisting of H, 1 amino acid and 2 amino acids and $X_2$ is selected from the group consisting of a modified C-terminal group, one or more carboxy-protecting groups and 1 to 17 amino acids.

31. The compound of claim 29, wherein said compound is linear.

32. The compound of claim 29, wherein said compound is cyclic.

33. The compound of claim 32, wherein the cyclization is through a bridge outside the YIR motif.

34. The compound of claim 33, wherein the cyclization includes a bridge with the Ile residue present within the YIR motif.

35. The compound of claim 29 selected from the group consisting of:
Ac-Tyr-Ile-Arg-Leu-Ala—NH$_2$ (SEQ ID NO: 2),
Ac-Tyr-Ile-Arg-Leu-Pro—NH$_2$ (SEQ ID NO: 3),
Ac-(iBu)Tyr-Ile-Arg-Leu-Pro—NH$_2$ (SEQ ID NO: 4),
Ac-Tyr-Ile-Arg-N(CH$_3$)O(CH$_3$),
Ac-Tyr-{Ψ(CH$_2$NH)}-Ile-Arg-Leu-Pro—NH$_2$ (SEQ ID NO: 5),
Ac-Tyr-Ile-Arg—NH—CH$_2$(4-Pyridyl),
Ac-Tyr-Ile-{Ψ(CH$_2$NH)}-Arg-Leu-Pro—NH$_2$ (SEQ ID NO: 6),
Ac-Tyr-Chg-Arg(NO$_2$)-{Ψ(CH$_2$NH)}-Leu—NH$_2$ (SEQ ID NO: 7),
Ac-Tyr-Ile-Arg-{Ψ(COCH$_2$)}-Gly-Pro—NH$_2$ (SEQ ID NO: 8),
Ac-Tyr-Ile-Dab(N$^\gamma$—C$_3$H$_7$N)-Leu-Ala—NH$_2$ (SEQ ID NO: 9),
Ac-Tyr-Ile-PalMe(3)—NH$_2$,
Tyr-Ile-Arg—NH$_2$,
D-Tyr-Ile-Arg-Leu-Pro—NH$_2$,
Ac-(Bzl)Gly-(Chx)Gly-(3-guanidopropyl)Gly—NH$_2$,
Cyclo(Gly-Tyr-Ile-Arg-Gly) (SEQ ID NO: 10),
Tfa-(iBu)Tyr-Chg-Arg-Leu-Pro—NH$_2$ (SEQ ID NO: 11),
Ac-pAph-Chg-Arg-Leu-Pro—NH$_2$ (SEQ ID NO: 12),
Ac-Nal(2)-Chg-Arg-Leu-Pro—NH$_2$ (SEQ ID NO: 13),
Ac-pAph-Chg-PalMe—NH$_2$,
and pharmaceutically acceptable salts, amides, esters, alcohols and aldehydes thereof.

36. The method of specifically inhibiting the activity of factor Xa, comprising contacting the factor Xa with the compound of claim 1.

37. The method of claim 36, wherein
R$_1$ is

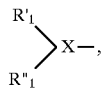

R'$_1$ is selected from the group consisting of H, —CO—R$_a$, —SO$_2$—R$_a$, an amino-protecting group, 1 to 6 amino acids, which can be substituted, wherein the N-terminus of said 1 to 6 amino acids is substituted with a substituent selected from the group consisting of H, —C(O)—R$_a$, —SO$_2$—R$_a$ and an amino-protecting group; and
wherein R$_a$ is selected from the group consisting of alkyl, aryl and heteroalkyl;
R"$_1$ is selected from the group consisting of H, acyl and alkyl;
X is N;
R$_2$ is —CHR$_{99}$—, wherein R$_{99}$ is selected from the group consisting of alkyl, aryl, arylalkyl, heteroalkyl and heteroaryl, which can be substituted with a substituent selected from the group consisting of 1 to 6 fluoro, chloro, bromo, iodo, amino, nitro, amidino, amido, carboxy, ester, ether and hydroxy groups;
R$_3$ is —C(O)—;
R$_4$ is —NH—;
R$_5$ is —CHR$_{201}$—, wherein R$_{201}$ is an alkyl;
R$_6$ is —C(O)—;
R$_7$ is —NH—;
R$_8$ is —CHR$_{210}$—, wherein R$_{210}$ is a heteroalkyl having at least one formal positive charge, wherein the heteroatom is 1 to 6 nitrogen atoms;
R$_9$ is —C(O)—; and
B is selected from the group consisting of —OR$_b$ and —N—R$_c$R$_d$,
wherein R$_b$ is selected from the group consisting of H, alkyl and a carboxy-protecting group,
R$_c$ is selected from the group consisting of H and alkyl, and
R$_d$ is selected from the group consisting of alkyl, heteroalkyl and 1 to 20 amino acids, which can be substituted with a substituent,
wherein the C-terminus of said compound can be modified with a carboxy-protecting group, a primary amide group or part of a cyclic peptide as the secondary or tertiary amide group formed with amino group of R$_1$ or by reduction to the alcohol.

38. The method of claim 37, wherein
A1 is selected from the group consisting of Tyr, F(pNH$_2$), mAph, pAph and Nal(2), which contain 0 or 1 amino-protecting groups;
A2 is selected from the group consisting of Ile and Chg;
A3 is selected from the group consisting of Arg, PalMe(3), Dab(N$^\gamma$—C$_3$H$_7$N), Dap(N$^\beta$—C$_3$H$_7$N) and Orn(N$^\delta$—C$_3$H$_7$N); and
B is selected from the group consisting of —H, —OH, —NH$_2$, one to five amino acids or functional equivalents thereof and a C-terminus protecting group.

39. The method of claim 38, wherein said compound is selected from the group consisting of:
Ac-pAph-Chg-PalMe(3)—NH—CH$_2$-Chx;
Ac-pAph-Chg-PalMe(3)—NH-Chx;
Bzf-pAph-Chg-PalMe(3)—NH$_2$;
Ac-pAph-Chg-PalMe(3)-L-P—NH$_2$ (SEQ ID NO: 15);
Ac-pAph-Chg-PalMe(3)—NH$_2$;
Cyclopentyl-CO-pAph-Chg-PalMe(3)—NH$_2$;
3-Iqc-pAph-Chg-PalMe(3)—NH$_2$;
2-Furoyl-pAph-Chg-PalMe(3)—NH$_2$;
5-Me-2-thienyl-CO-pAph-Chg-PalMe(3)—NH$_2$; and
Ac-pAph-Chg-PalMe(3)-ol.

40. The method of claim 38, wherein said compound is selected from the group consisting of:
Ac-Y-I-R-L-A—NH$_2$ (SEQ ID NO: 290),
Ac-Y-I-R-L-P—NH$_2$ (SEQ ID NO: 149),
Ac-(iBu)Y-I-R-L-P—NH$_2$ (SEQ ID NO: 94),
Ac-Y-I-R-N(CH$_3$)O(CH$_3$),
Ac-Y-{Ψ(CH$_2$NH)}-I-R-L-P—NH$_2$ (SEQ ID NO: 135),
Ac-Y-I-R—NH—CH$_2$(4-Pyridyl),
Ac-Y-I-{Ψ(CH$_2$NH)}-R-L-P—NH$_2$ (SEQ ID NO: 141),
Ac-Y-Chg-R(NO$_2$)-{Ψ(CH$_2$NH)}-L—NH$_2$ (SEQ ID NO: 131),
Ac-Y-I-R-{Ψ(COCH$_2$)}-G-P—NH$_2$ (SEQ ID NO: 136),
Ac-Y-I-Dab(N$^\gamma$—C$_3$H$_7$N)-L-A—NH$_2$ (SEQ ID NO: 137),
Ac-Y-I-PalMe(3)—NH$_2$,
Y-I-R—NH$_2$,
y-I-R-L-P—NH$_2$,
Ac-(Bzl)Gly-(Chx)Gly-(3-guanidopropyl)Gly—NH$_2$,
Cyclo(G-Y-I-R-G) (SEQ ID NO: 183), Tfa-(iBu)Y-Chg-R-L-P—NH$_2$ (SEQ ID NO: 221),
Ac-pAph-Chg-R-L-P—NH$_2$ (SEQ ID NO: 122),
Ac-Nal(2)-Chg-R-L-P—NH$_2$ (SEQ ID NO: 119),
and pharmaceutically acceptable salts, amides, esters, alcohols and aldehydes thereof, wherein Y-I-R is the amino acid sequence tyrosine-isoleucine-arginine.

41. A method of inhibiting blood clotting in an individual, comprising administering the compound of claim 1 to the individual.

42. A method of diagnosing the level of factor Xa in a sample, comprising contacting the sample with the compound of claim 1 and detecting the amount of binding.

43. A method of diagnosing the level of active factor Xa in a sample, comprising contacting a sample with the compound of claim 1 and detecting the amount of factor Xa enzymatic activity.

* * * * *